United States Patent
Kwon et al.

(10) Patent No.: US 10,391,067 B2
(45) Date of Patent: Aug. 27, 2019

(54) PREVENTION AND TREATMENT OF NEURODEGENERATIVE DISEASES THROUGH AUTOPHAGY ACTIVITY MEDIATED BY A SYNTHETIC LIGAND OR ARGINYLATED BIP BINDING TO THE P62 ZZ DOMAIN

(71) Applicants: Seoul National University R&DB Foundation, Seoul (KR); Korea Research Institute of Bioscience and Biotechnology, Daejeon (KR)

(72) Inventors: Yong Tae Kwon, Seoul (KR); Bo Yeon Kim, Daejeon (KR); Hyunjoo Cha, Daejeon (KR); Young Dong Yoo, Gyeonggi-do (KR); Ji-eun Yu, Daejeon (KR)

(73) Assignee: AUTOTAC BIO, Seoul (KR)

(*) Notice: Subject to any disclaimer, the term of this patent is extended or adjusted under 35 U.S.C. 154(b) by 0 days.

(21) Appl. No.: 15/753,026

(22) PCT Filed: Jul. 15, 2016

(86) PCT No.: PCT/KR2016/007745
§ 371 (c)(1),
(2) Date: Feb. 15, 2018

(87) PCT Pub. No.: WO2017/030292
PCT Pub. Date: Feb. 23, 2017

(65) Prior Publication Data
US 2018/0243244 A1 Aug. 30, 2018

(30) Foreign Application Priority Data
Aug. 18, 2015 (KR) .......................... 10-2015-0116015

(51) Int. Cl.
| | | |
|---|---|---|
| A61K 31/138 | (2006.01) | |
| A61K 38/05 | (2006.01) | |
| A61K 38/10 | (2006.01) | |
| A61K 38/16 | (2006.01) | |
| A61K 31/122 | (2006.01) | |
| A61K 31/13 | (2006.01) | |
| A61P 25/28 | (2006.01) | |

(52) U.S. Cl.
CPC .......... *A61K 31/138* (2013.01); *A61K 31/122* (2013.01); *A61K 31/13* (2013.01);
(Continued)

(58) Field of Classification Search
CPC .............................. A61K 31/138; A61P 25/28
(Continued)

(56) References Cited

U.S. PATENT DOCUMENTS

| | | | |
|---|---|---|---|
| 8,187,802 B2 | 5/2012 | White et al. ...................... 435/4 |
| 2015/0175607 A1 | 6/2015 | Xie et al. ........................... 475/8 |

FOREIGN PATENT DOCUMENTS

| | | | |
|---|---|---|---|
| CZ | 131157 | * | 2/1969 |
| JP | 2014-113124 | | 6/2014 |

(Continued)

OTHER PUBLICATIONS

Translation CZ131157MT partial machine translation (Year: 2018).*
Translation CZ13157CZA partial human translation (Year: 2018).*
Ablad et al. Acta Pharm. Suecica, (1970), vol. 7, pp. 551-558 (Year: 1970).*
Cha-Molstad et al. "Amino-terminal arginylation targets endoplasmic reticulum chaperone BiP for autophagy through p62 binding" Nature Cell Biology Jul. 2015 vol. 17(7):917-929, Methods and supplementary information attached DOI: 10.1038/ncb3177.
International Search Report dated Sep. 12, 2016 in PCT/KR2016/007745.
Cha-Molstad et al. "p62/SQSTM1 /Sequestosome-1 is an N-recognin of the N-end rule pathway which modulates autophagosome biogenesis" Nature Communications 2017 8:1-17.
(Continued)

*Primary Examiner* — Melenie L Gordon
*Assistant Examiner* — Taina D Matos Negron
(74) *Attorney, Agent, or Firm* — Licata & Tyrrell P.C.

(57) ABSTRACT

The pharmacokinetics and key technologies of the present invention are summarized in FIG. 1. Particularly, malignant misfolded proteins such as mutant huntingtin and alpha-synuclein are coagulated and grow into oligomeric coagulum (①, ②), fibrillar coagulum (③) and eventually inclusion body (④). Young neurons produce a large amount of Nt-Arg through N-terminal arginylation (⑤) of vesicle chaperones such as BiP secreted into the cytoplasm, and then arginylated BiP (R-BiP) is secreted binds to the misfolded proteins (⑥). As a ligand, the Nt-Arg of R-BiP binds to the p62 ZZ domain (⑦), and the normally inactivated closed form of p62 is changed to an open form, leading to structural activation (⑧). As a result, PB1 and LC3-binding domains are exposed. The PB1 domain induces oligomerization (⑨), leading to the concentration as a p62 body (⑩) that is a coagulum capable of being degraded by autophagy. Then, p62 binds to LC3, which is protruding from the autopagosomal membranes, leading to the completion of autophagy targeting (⑪) and lysosomal proteolysis. Since autophagy proteolysis including steps (⑤)-(⑪) is strong in young neurons, cytotoxic protein coagulums (①)-⑤) do not accumulate. However in aged neurons, autophagy proteolysis including steps ⑤-⑪ is weakened, and protein coagulums (①-⑤) accumulate and become cytotoxic. In this invention, p62 is intentionally activated (⑫, ⑬) by using low mass ligands of the p62 ZZ domain to effectively remove huntingtin and alpha-synuclein protein coagulums. Particularly, in step ⑫, p62 ligated with a ligand accelerates the oligomerization of p62-R-BiP-misfolded protein (⑨) and the formation of autophagy coagulum (⑩). In step (⑬), the ligand-p62 conjugate acts as an autophagy activator (⑭) to induce the synthesis of LC3 and the conversion of LC3-I into LC3-II in order to accelerate the formation of autophagosomes (⑮).

2 Claims, 45 Drawing Sheets

Specification includes a Sequence Listing.

(52) U.S. Cl.
CPC .............. *A61K 38/05* (2013.01); *A61K 38/10* (2013.01); *A61K 38/16* (2013.01); *A61P 25/28* (2018.01); *Y02A 50/401* (2018.01)

(58) Field of Classification Search
USPC ........................................................ 514/646
See application file for complete search history.

(56) References Cited

FOREIGN PATENT DOCUMENTS

| KR | 10-2015-0039894 | 4/2015 |
|----|-----------------|--------|
| KR | 10-2015-0080706 | 7/2015 |

OTHER PUBLICATIONS

Ciechanover, A. and Kwon, Y.T. "Degradation of misfolded proteins in neurodegenerative diseases: therapeutic targets and strategies" Experimental & Molecular Medicine 2015 47:1-16.

Harris, H. and Rubinsztein, D. C. "Control of autophagy as a therapy for neurodegenerative disease" Nature Reviews Neurology 2012 8:108-117.

Nixon, R. "The role of autophagy in neurodegenerative diseases" Nature Medicine 2013 19:983-997.

Wooten et al. "Signaling, polyubiquitination, trafficking, and inclusions: sequestosome 1 /p62's role in neurodegenerative disease" Journal of Biomedicine and Biotechnology 2006 1-12.

\* cited by examiner

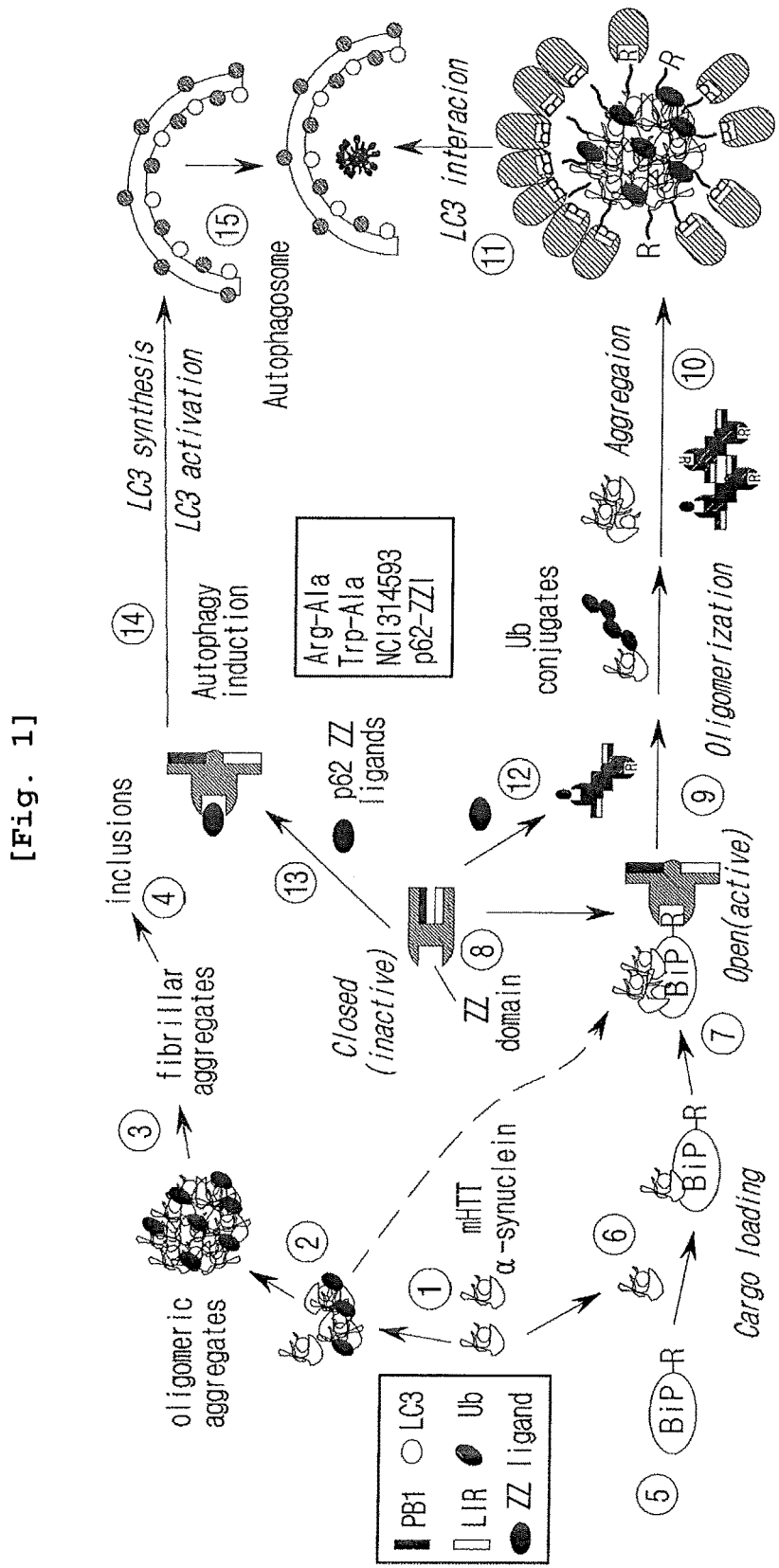
[Fig. 1]

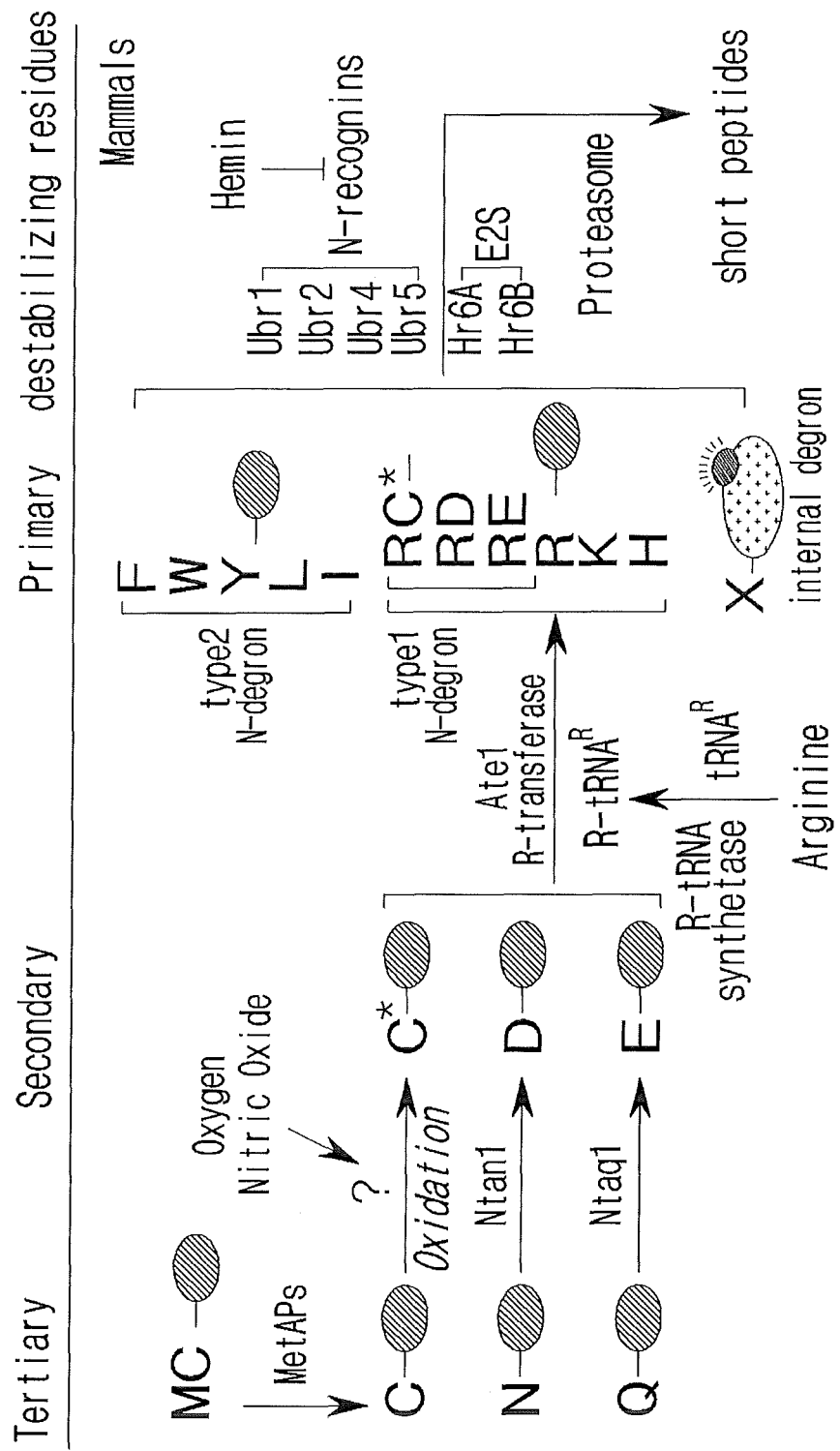
[Fig. 2]

[Fig. 3a]

| UBR Proteins | Size (kDa) | Specificity to N-terminus | Conserved domains |
|---|---|---|---|
| UBR1 | 200 | type 1,2 | UBR box N-domain — RING — UAIN |
| UBR2 | 200 | type 1,2 | UBR box N-domain — RING — UAIN |
| UBR3 | 213 | ? | UBR box — RING — UAIN |
| UBR4 | 570 | type 1,2 | UBR box — CRD — HECT |
| UBR5 | 300 | type 1 | UBR box — UBR box |
| UBR6 | 90 | ? | F-box — UBR box |
| UBR7 | 50 | ? | UBR box PHD |

[Fig. 3b]

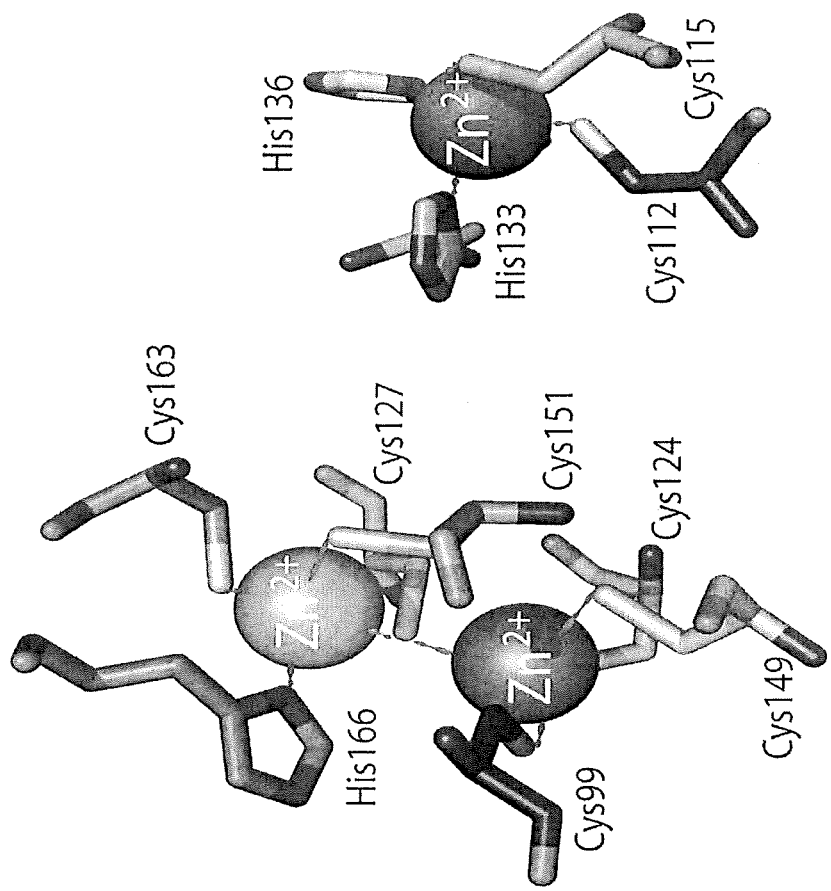
[Fig. 3c]

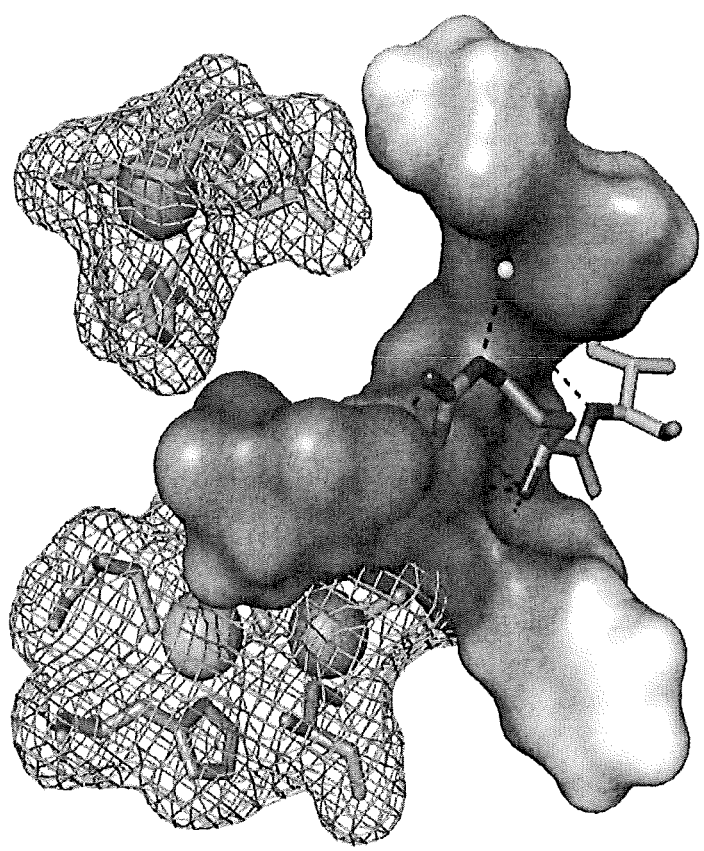
[Fig. 3d]

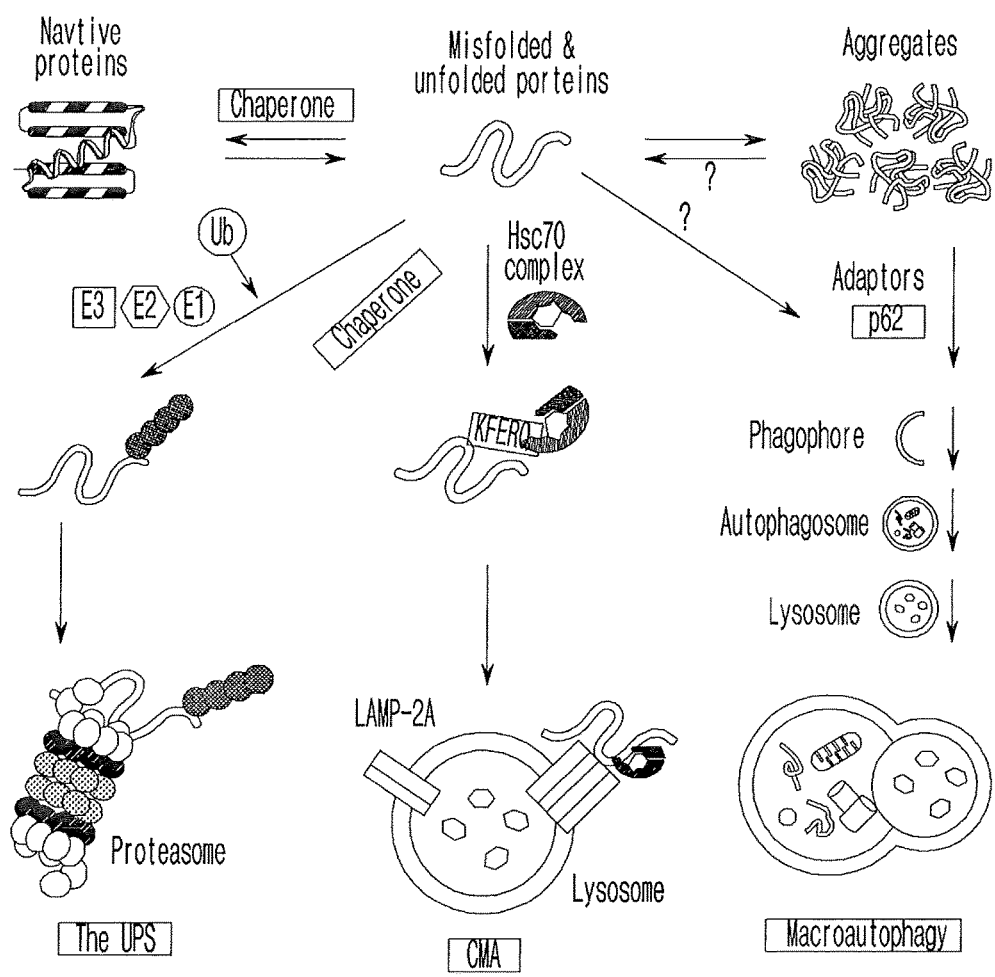
[Fig. 4]

[Fig. 5a]
Rat testis protein
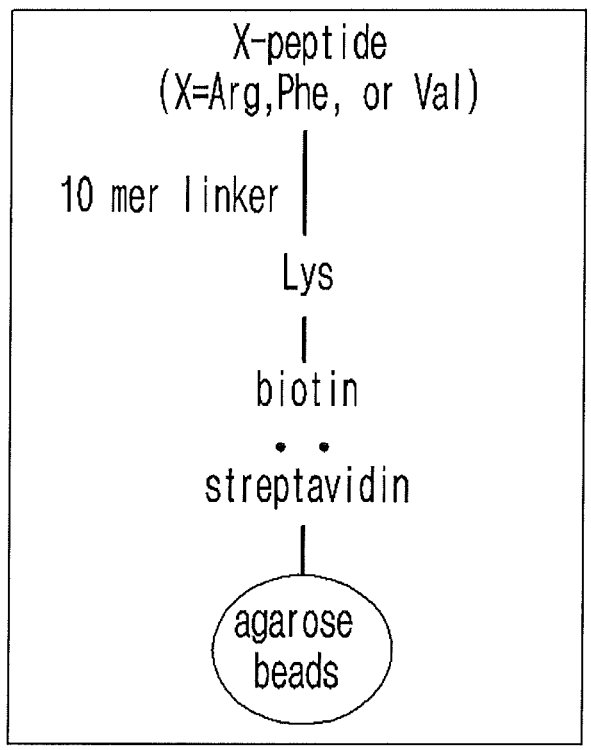
Incubation
Wash
Elute
iTRAQ-MS/MS analysis

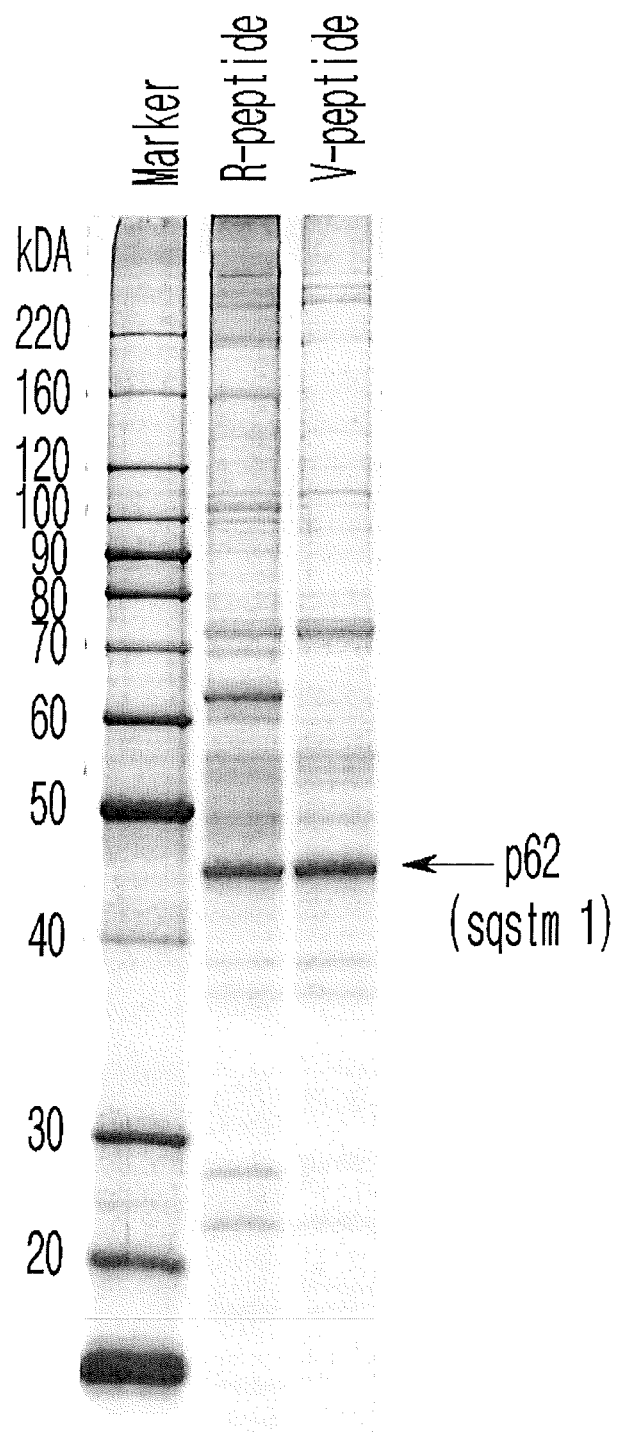
[Fig. 5b]

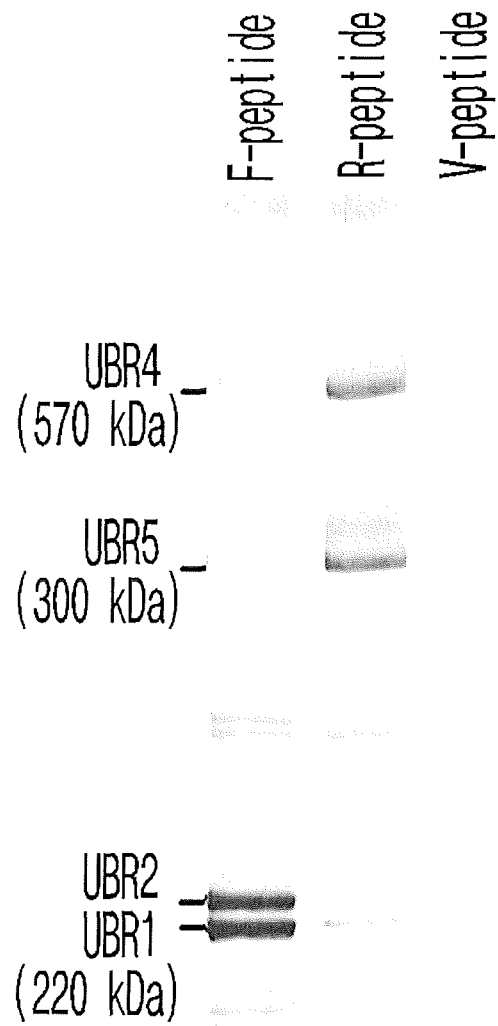
[Fig. 5c]

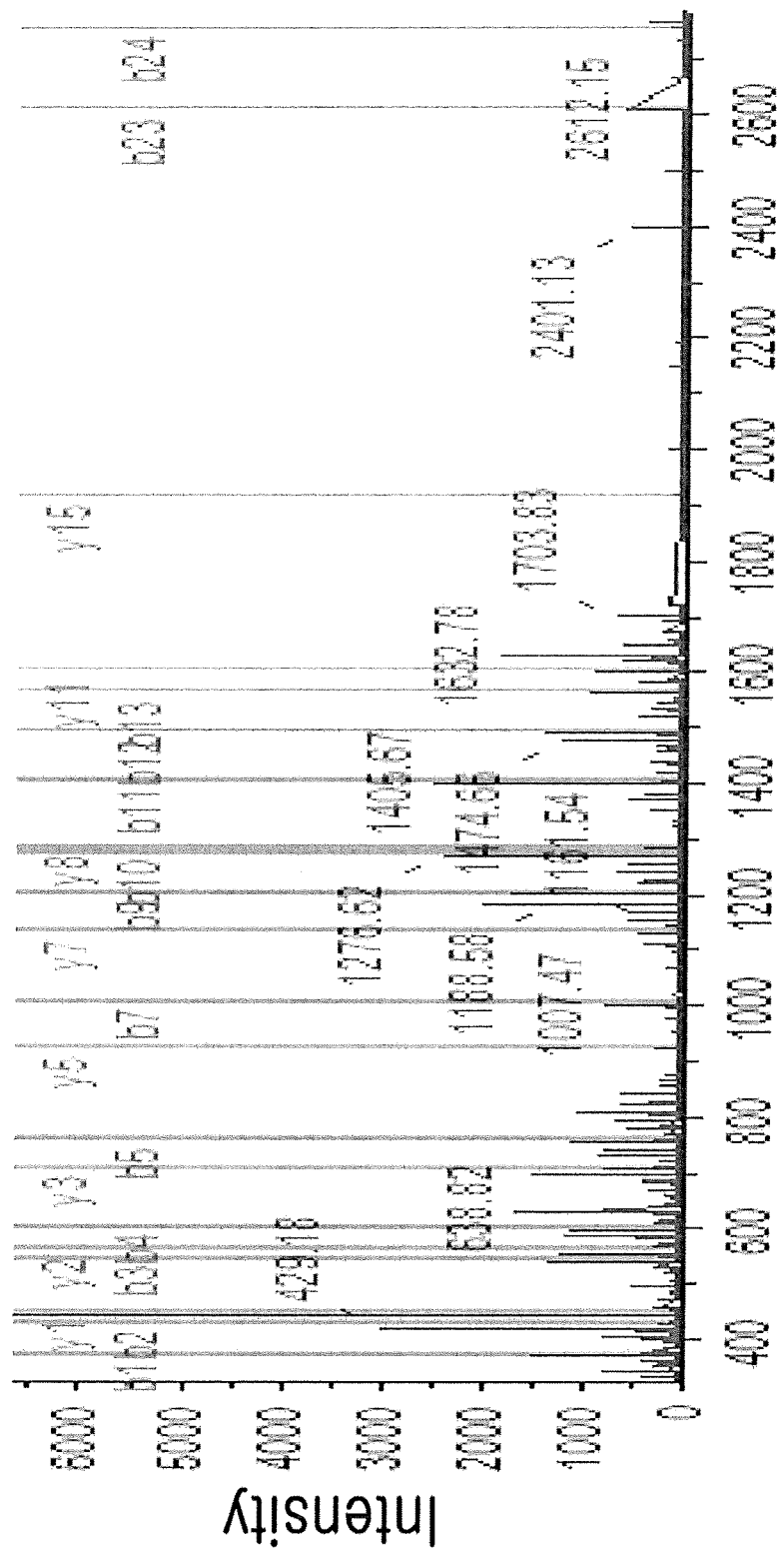

[Fig. 5e]
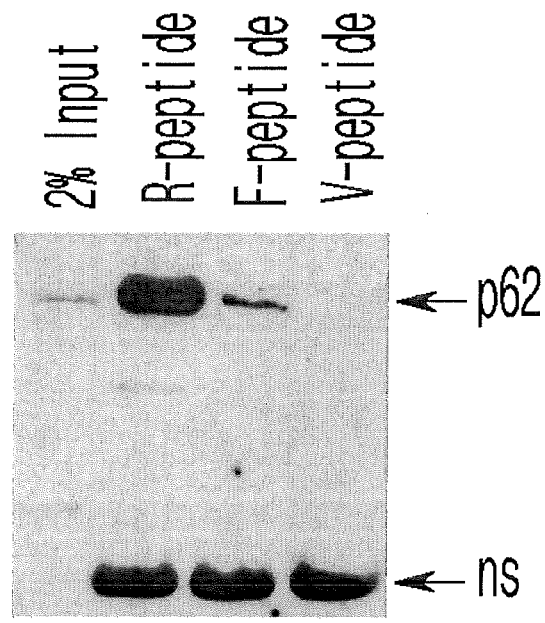
[Fig. 5f]

[Fig. 5g]
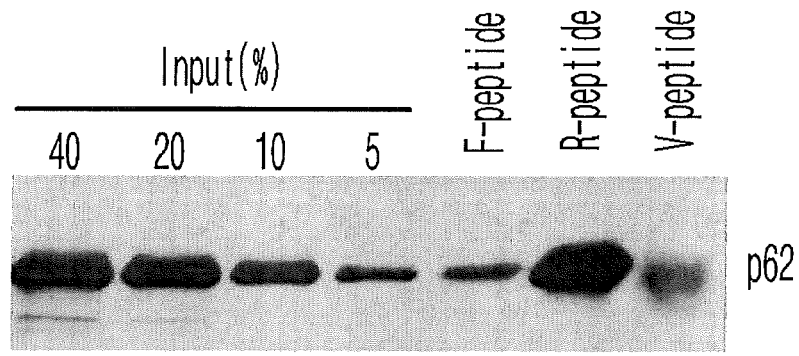
[Fig. 5h]
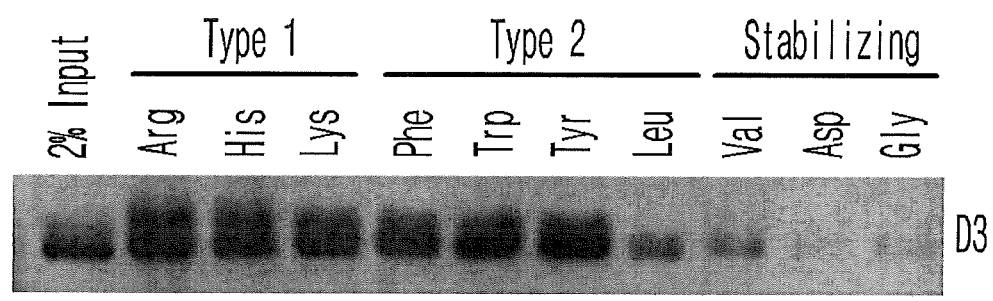
[Fig. 5i]
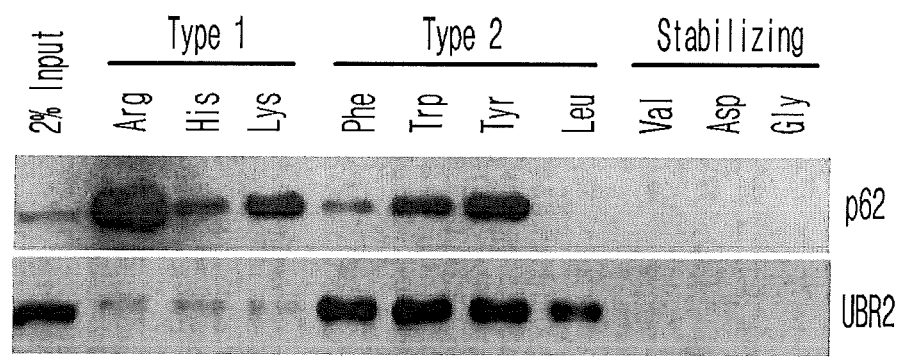

[Fig. 6a]
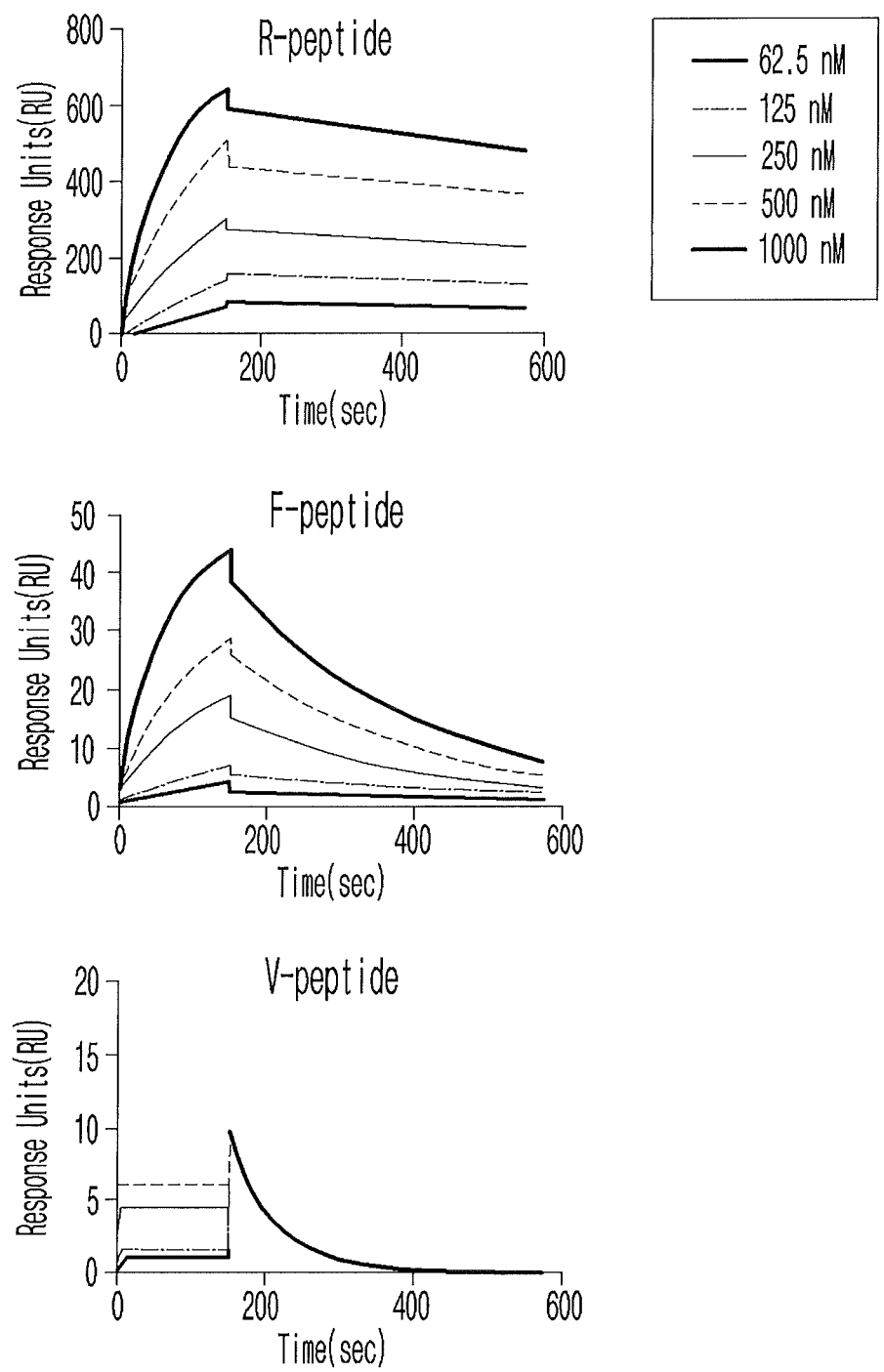

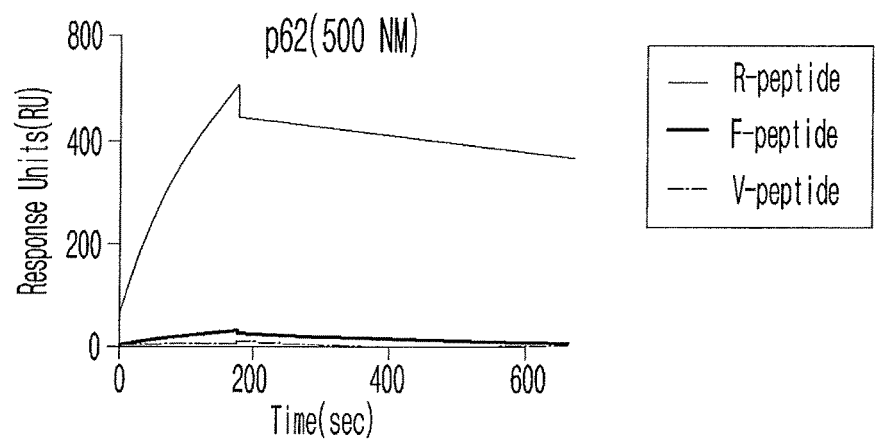
[Fig. 6b]
[Fig. 6c]
| X-peptide | ka(1/Ms) x $10^2$ | ka(1/s) x $10^{-3}$ | KD(M) x $10^{-8}$ |
|---|---|---|---|
| R-peptide | 122.7 | 0.5 | 4.4 |
| F-peptide | 5.5 | 1.9 | 343.8 |
| V-peptide | ND | ND | ND |

[Fig. 7a]
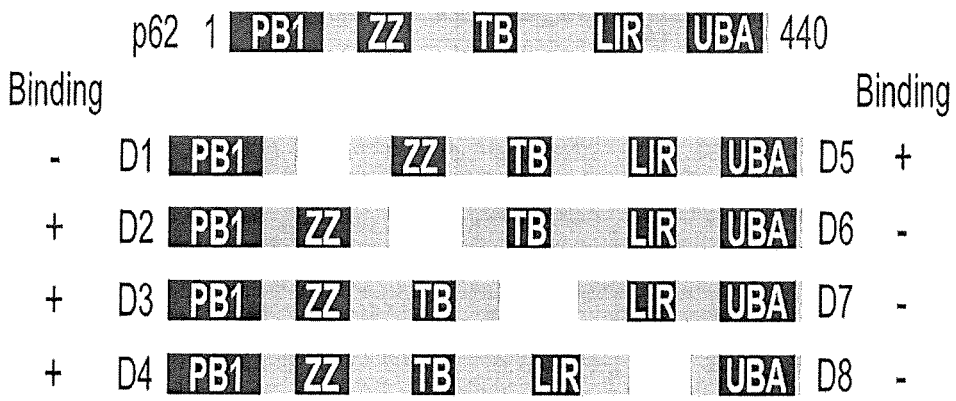
[Fig. 7b]
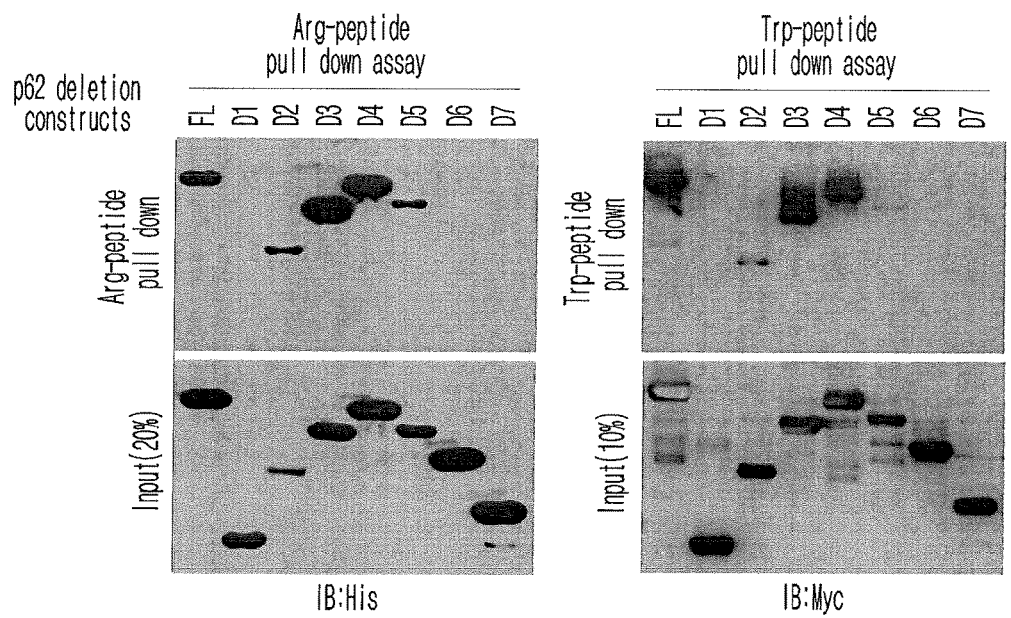

[Fig. 7c]

Binding

- \+ p62D3  `PB1` `ZZ` `TB` 310
- \+ CD-1  `PB1` `ZZ` `TB` 272
- \+ CD-2  `PB1` `ZZ` `T` 233
- \+ CD-3  `PB1` `ZZ` 194
- \+ CD-4  `PB1` `ZZ` 184
- \+ CD-5  `PB1` `ZZ` 175
- \+ CD-6  `PB1` `ZZ` 165
- − CD-7  `PB1` `ZZ` 156
- − CD-8  `PB1` `Z` 146
- − CD-9  `PB1` 132

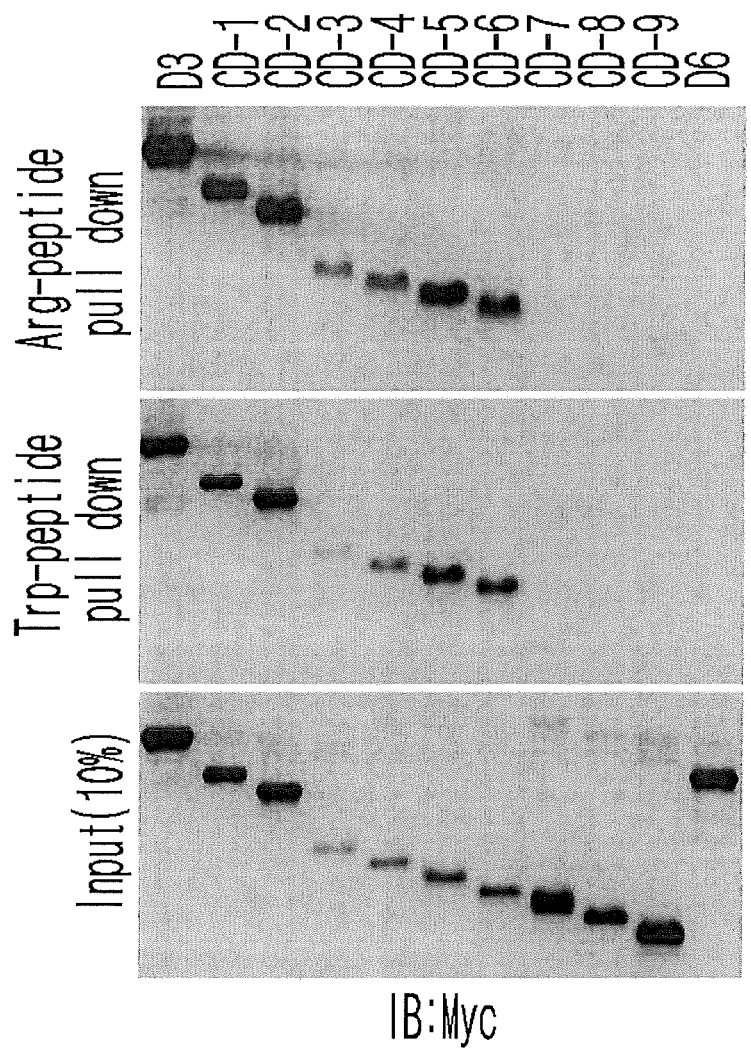

[Fig. 7e]

Binding

+ p62FL 1 PB1  ZZ  TB  LIR  UBA

+ ND-1 40 PB1  ZZ  TB  LIR  UBA

+ ND-2  79  ZZ  TB  LIR  UBA

+ ND-3  117  ZZ  TB  LIR  UBA

- ND-4  131 ZZ  TB  LIR  UBA

- ND-5  145 Z  TB  LIR  UBA

- ND-6  155  TB  LIR  UBA

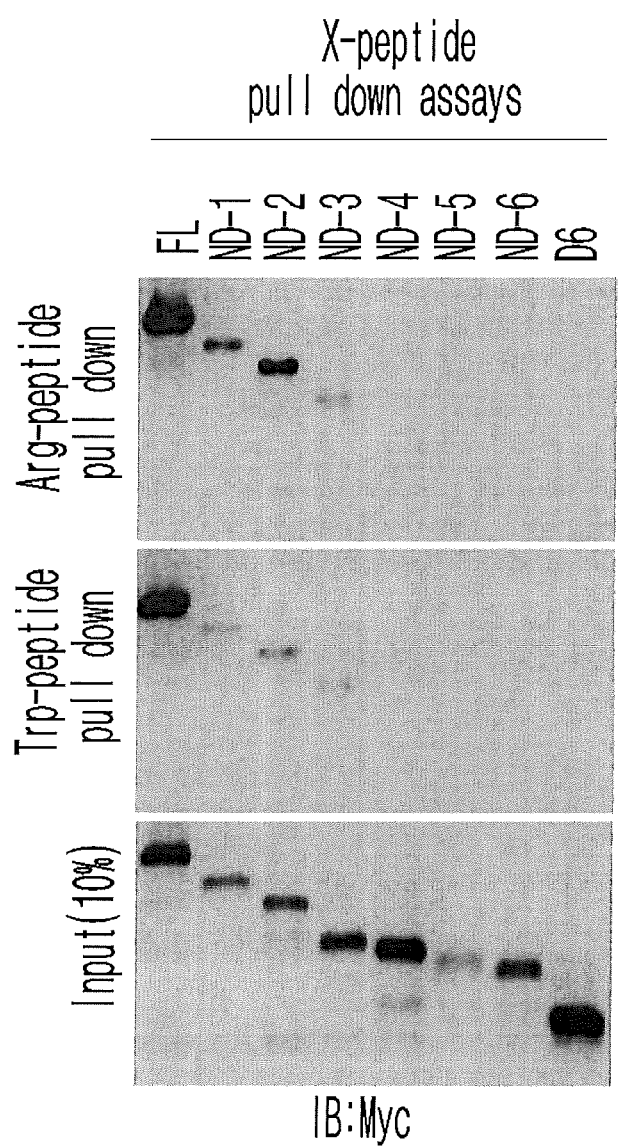
[Fig. 7f]

[Fig. 7g]
1-82   128-163   225-251   321-342   387-436
p62_FL  1 [PB1] [ZZ] [TB] [LIR] [UBA] 440
p62_ZZΔ 1 [PB1] [TB] [LIR] [UBA] 440
[Fig. 7h]
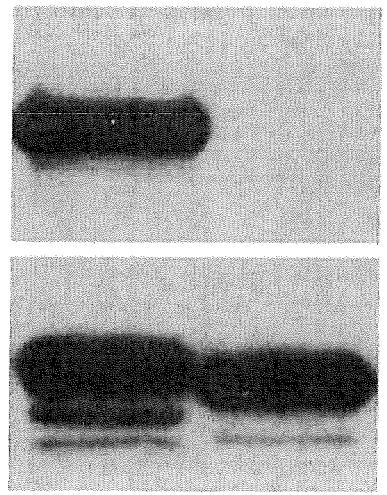

[Fig. 7i]
p62_ZZ (WT)    83 [ ZZ 128-163 ] 175
p62_ZZ (D129A) 83 [ ZZ ] 175
                    |
                  D129A
[Fig. 7j]
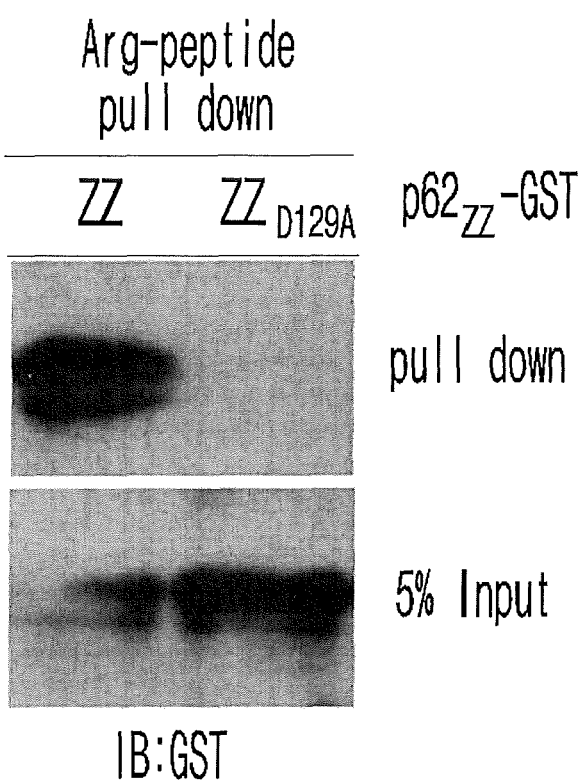
Arg-peptide pull down
ZZ | ZZ_D129A    p62_ZZ-GST
pull down
5% Input
IB:GST

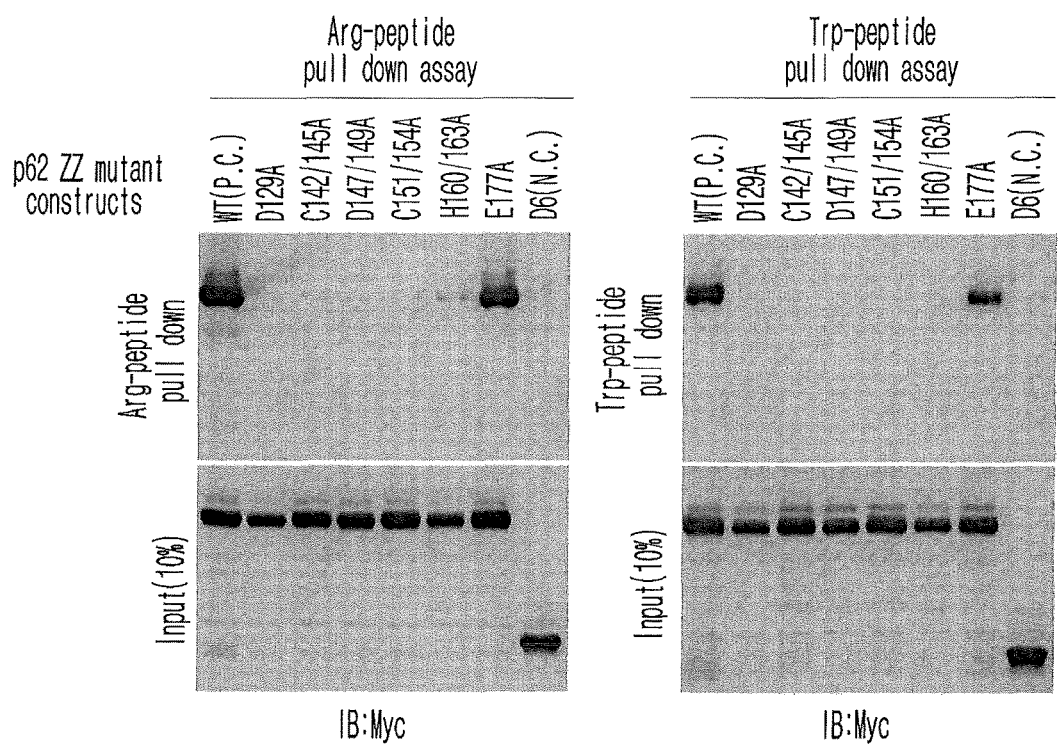

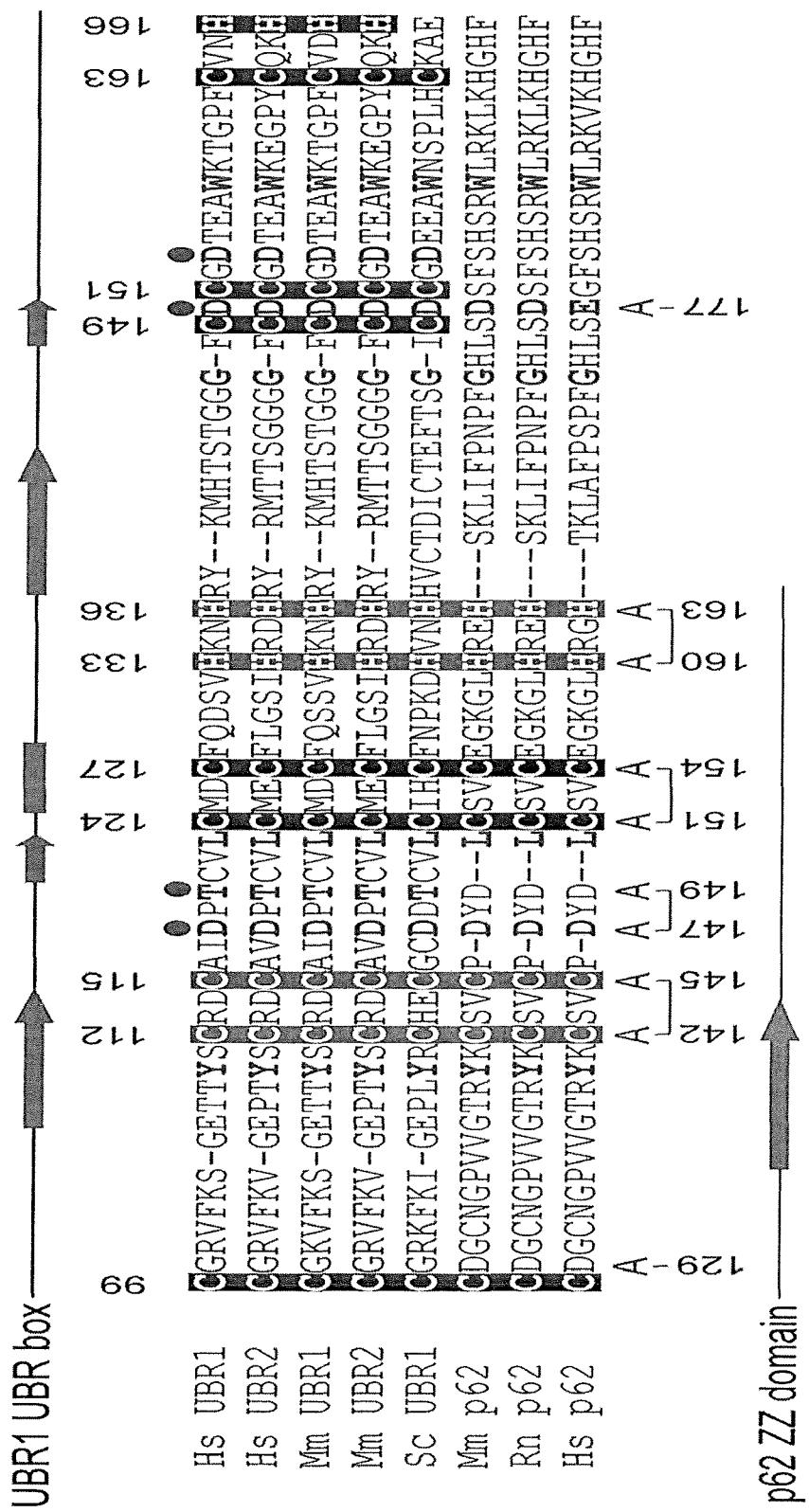
[Fig. 71]

[Fig. 8a]
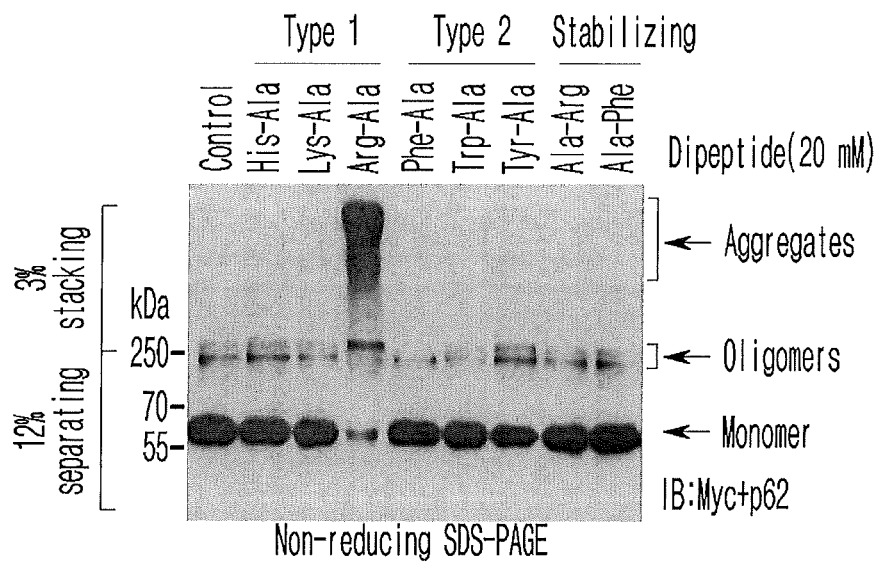
[Fig. 8b]
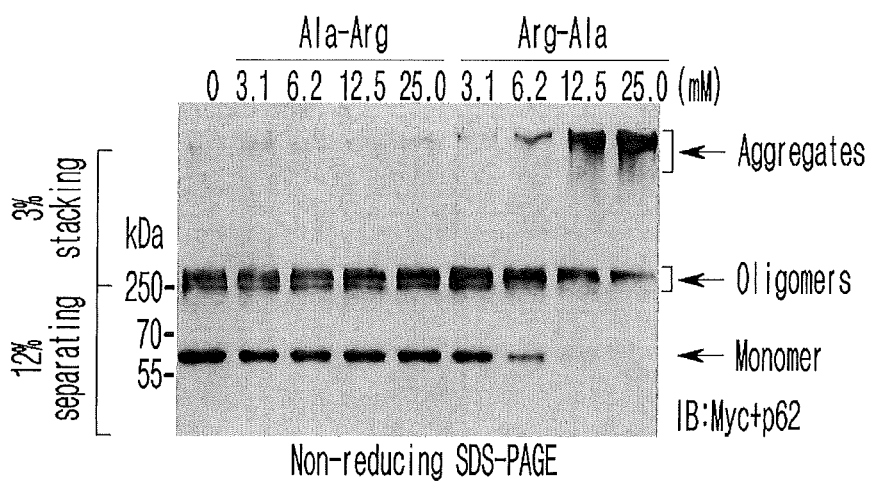

[Fig. 8c]
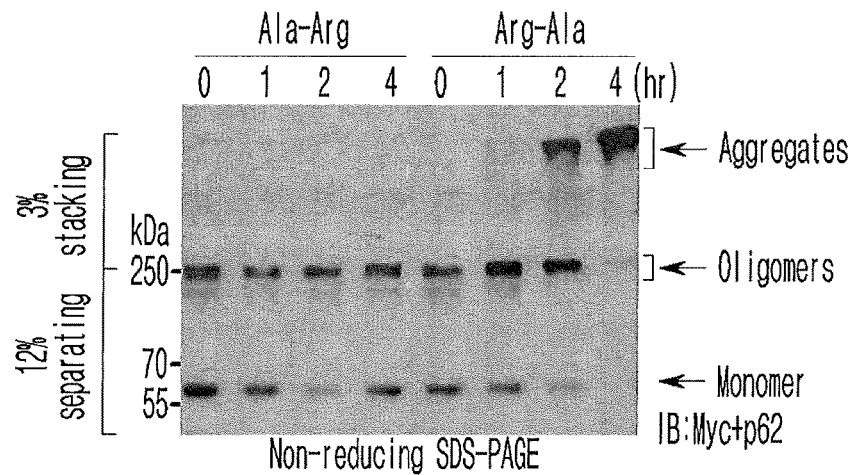
[Fig. 8d]
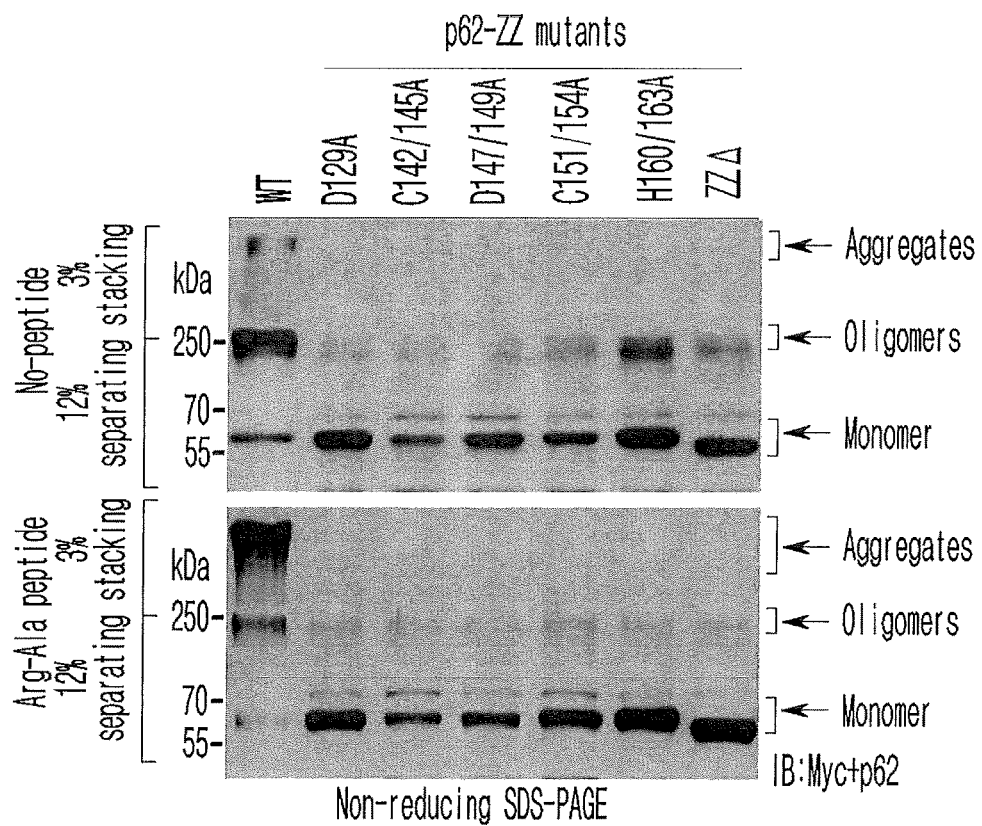

[Fig. 8e]
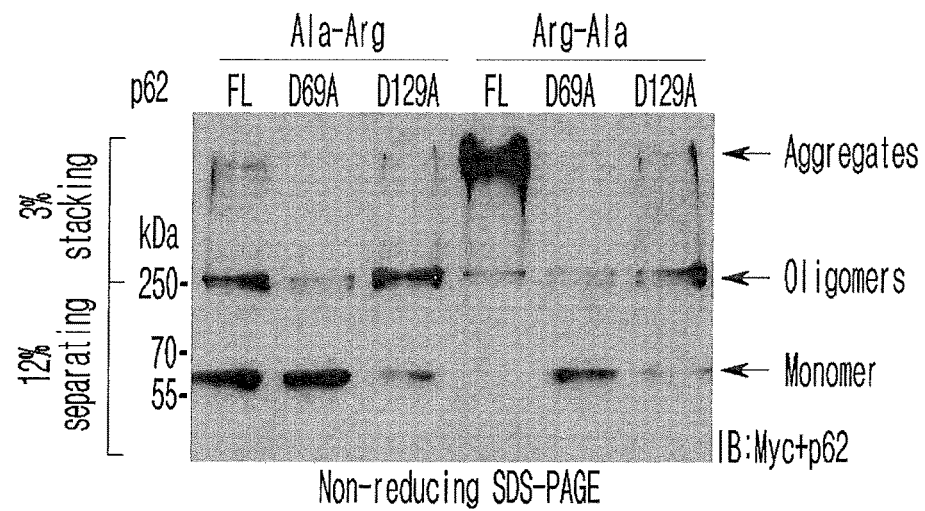
[Fig. 8f]
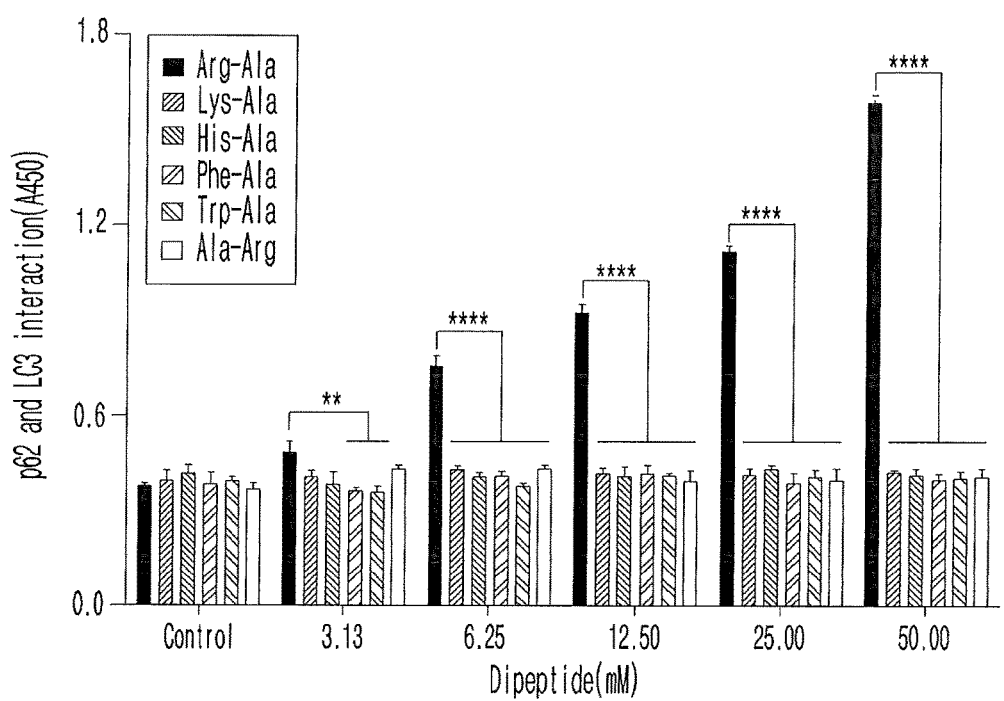

[Fig. 8g]
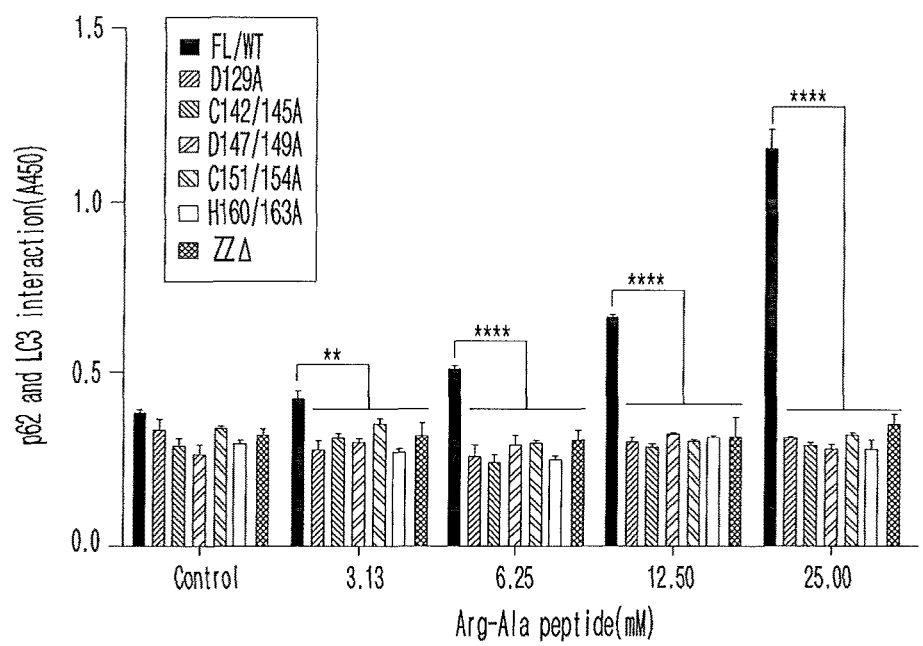
[Fig. 8h]
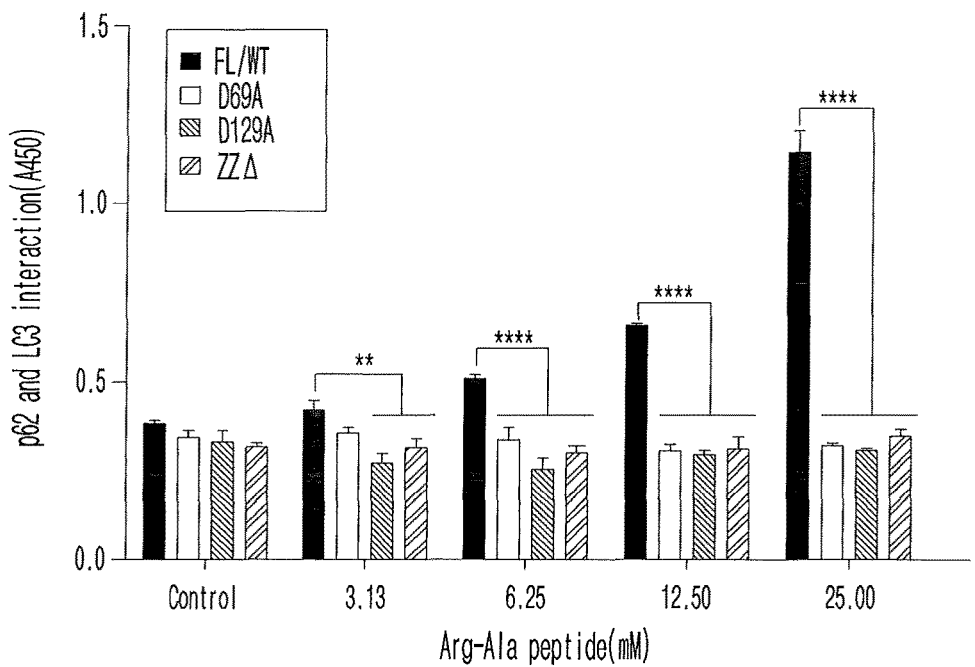

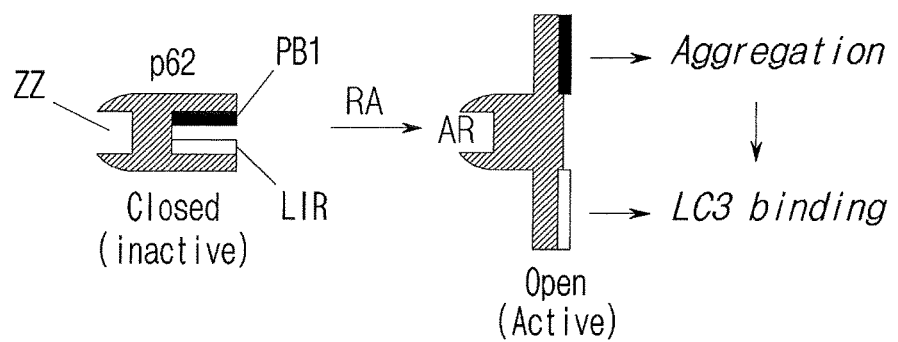
[Fig. 8i]

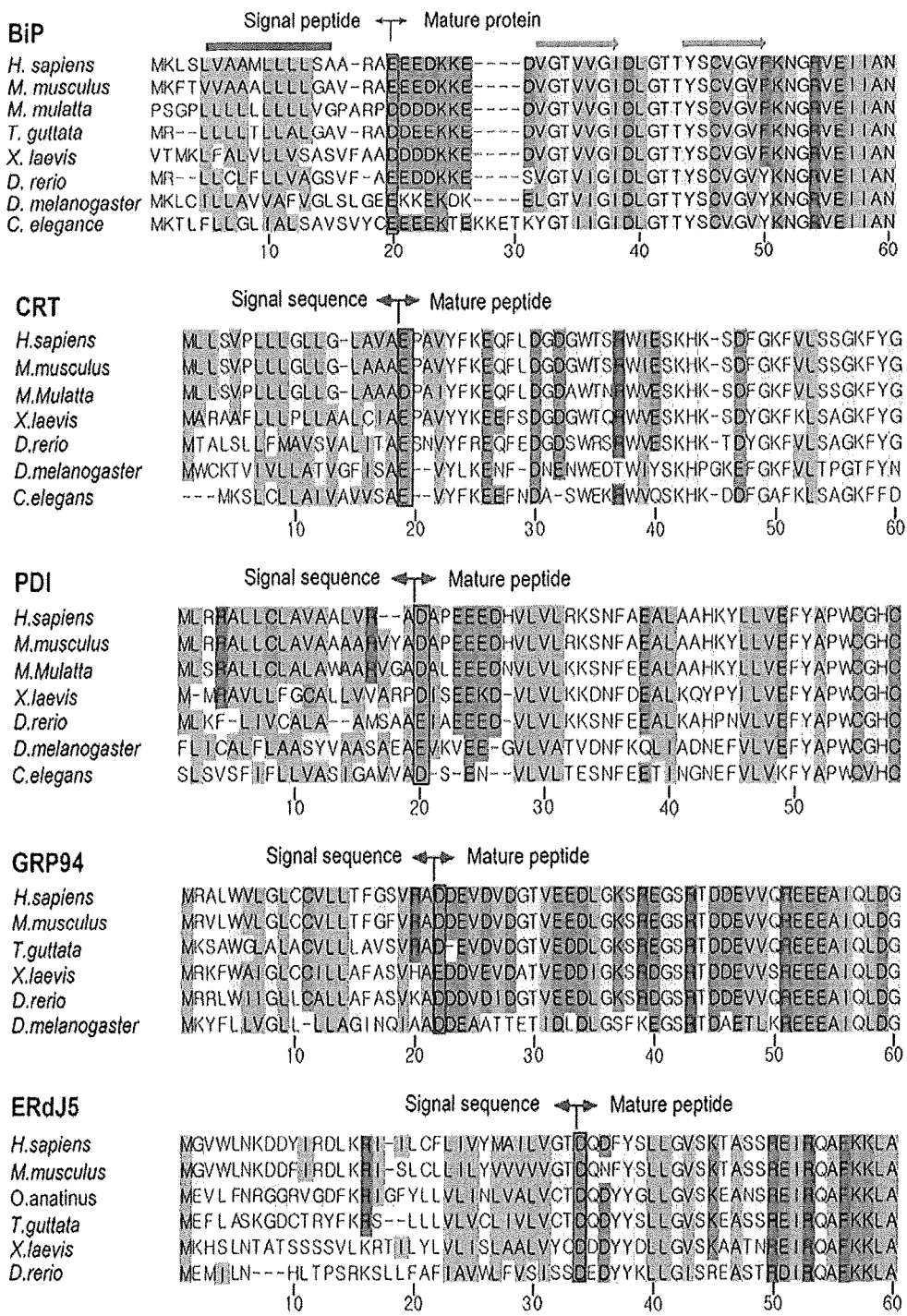
[Fig. 9]

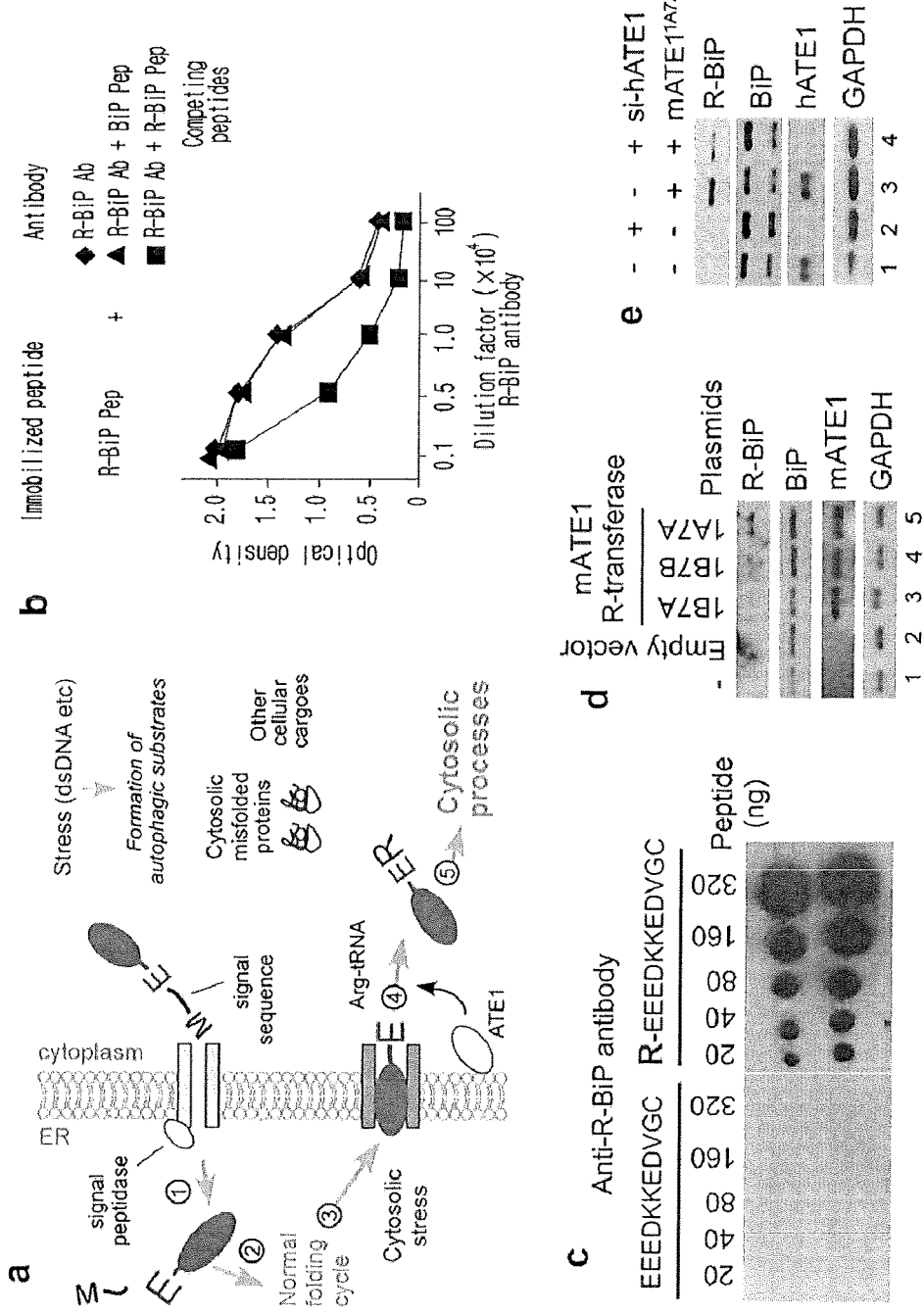

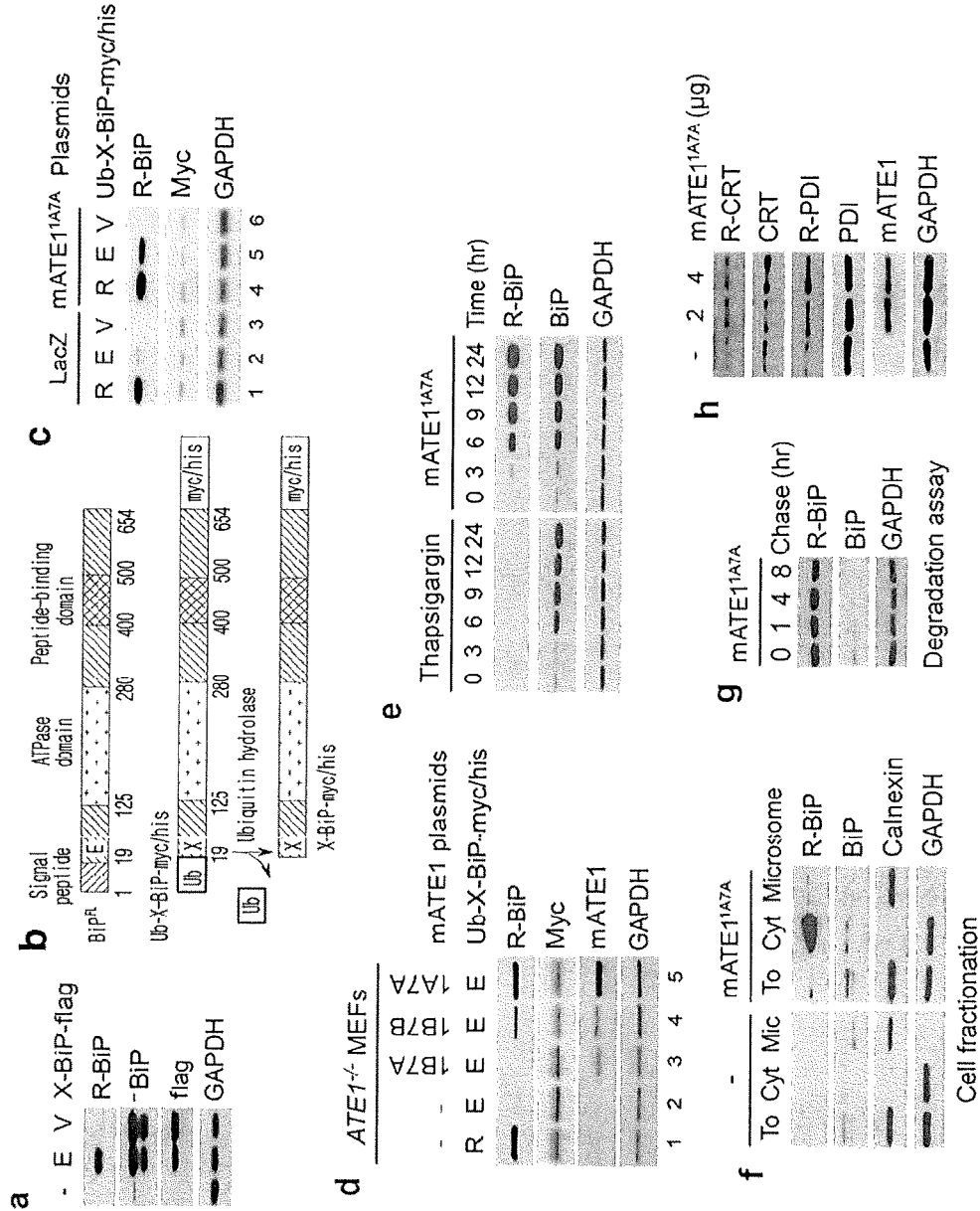
[Fig. 11]

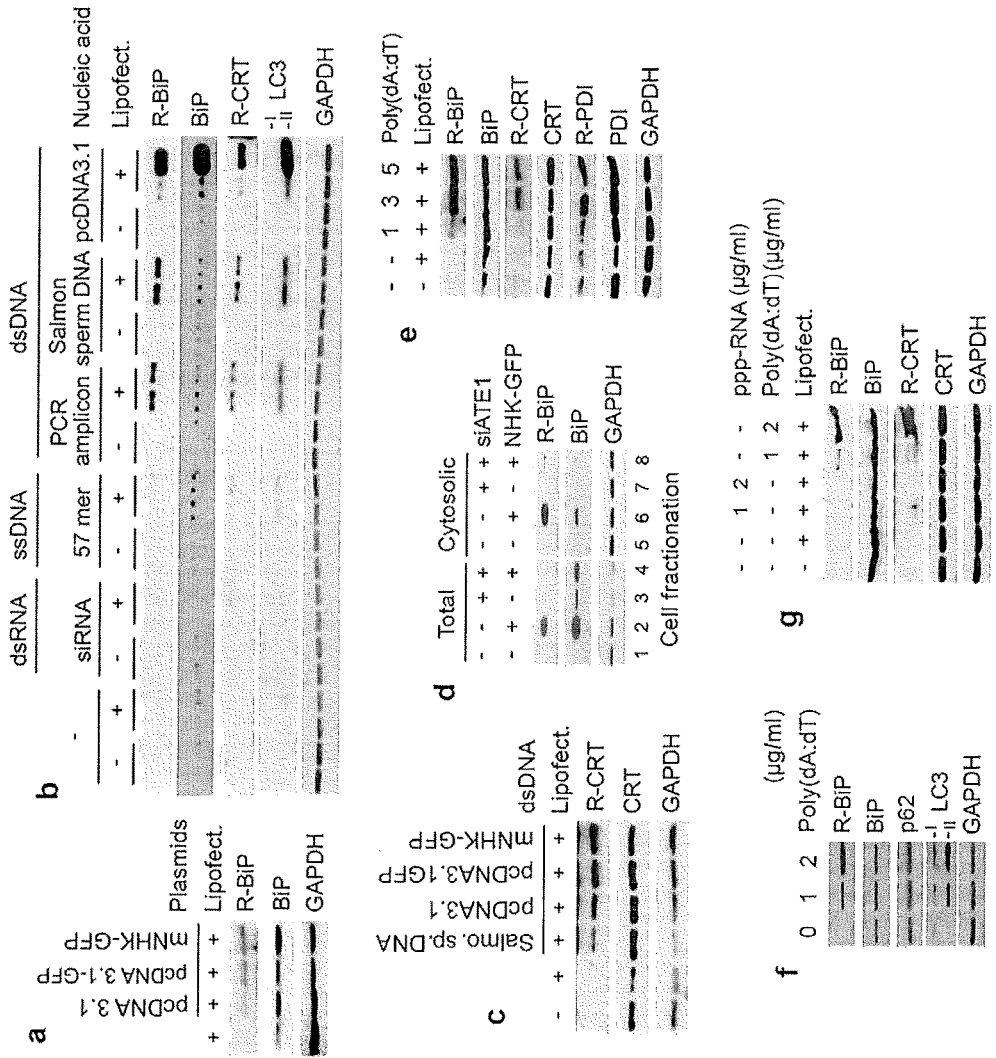
[Fig. 12]

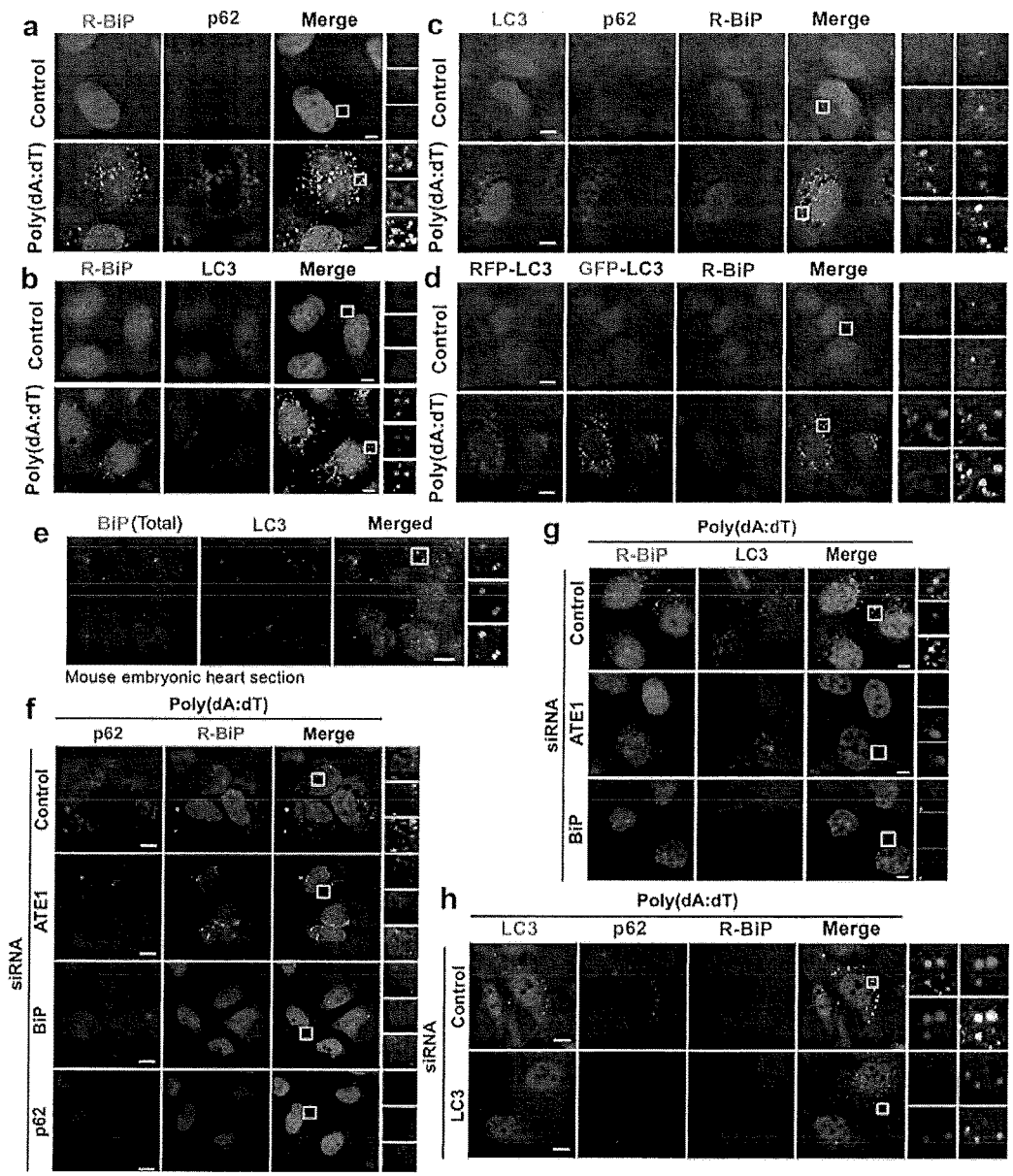
[Fig. 13]

[Fig. 14]
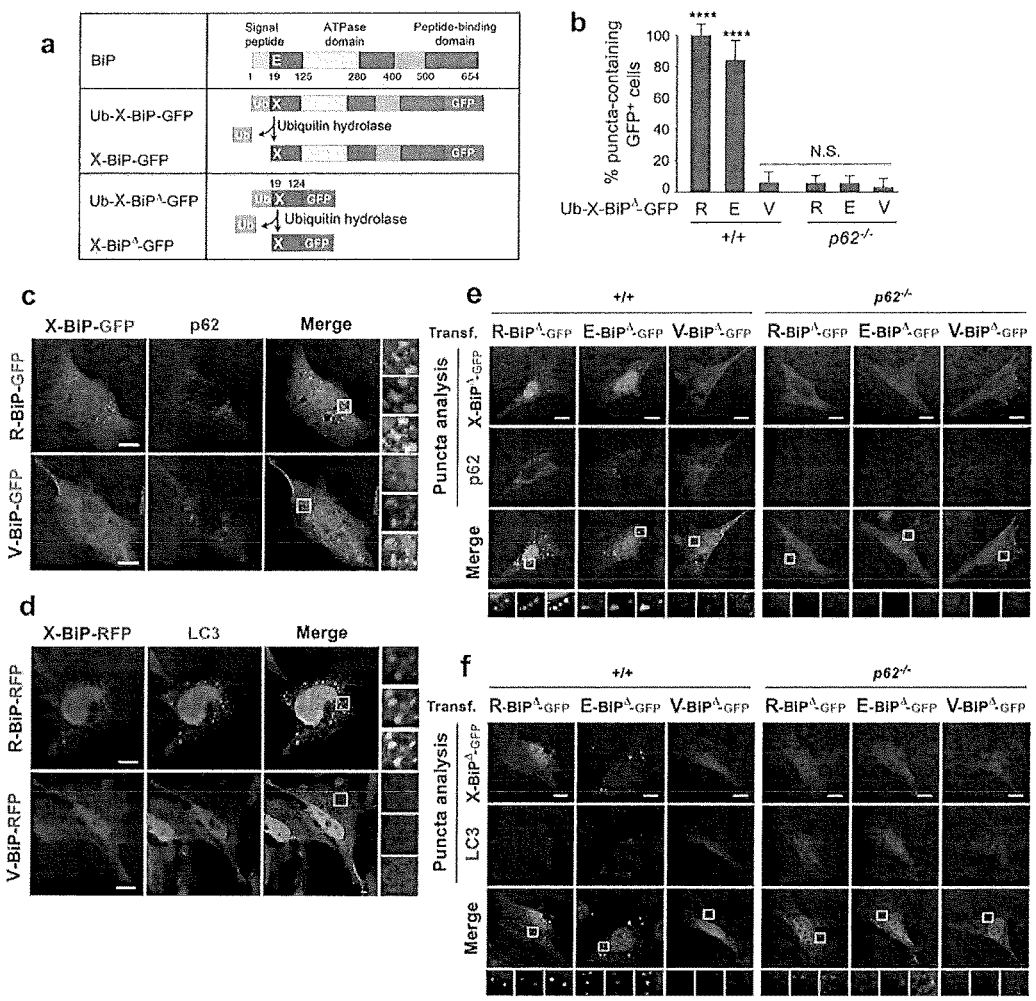

[Fig. 15]
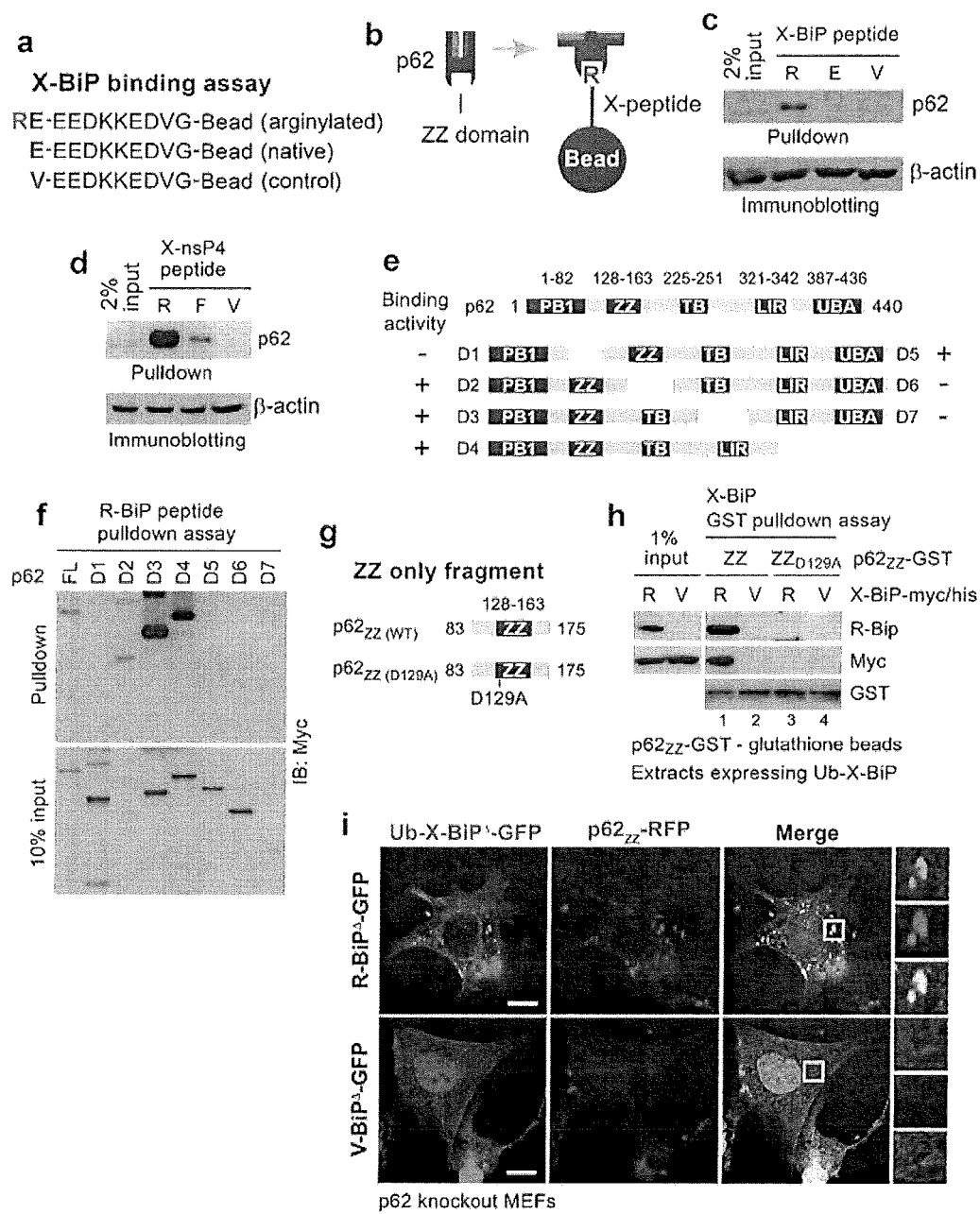

[Fig. 16]
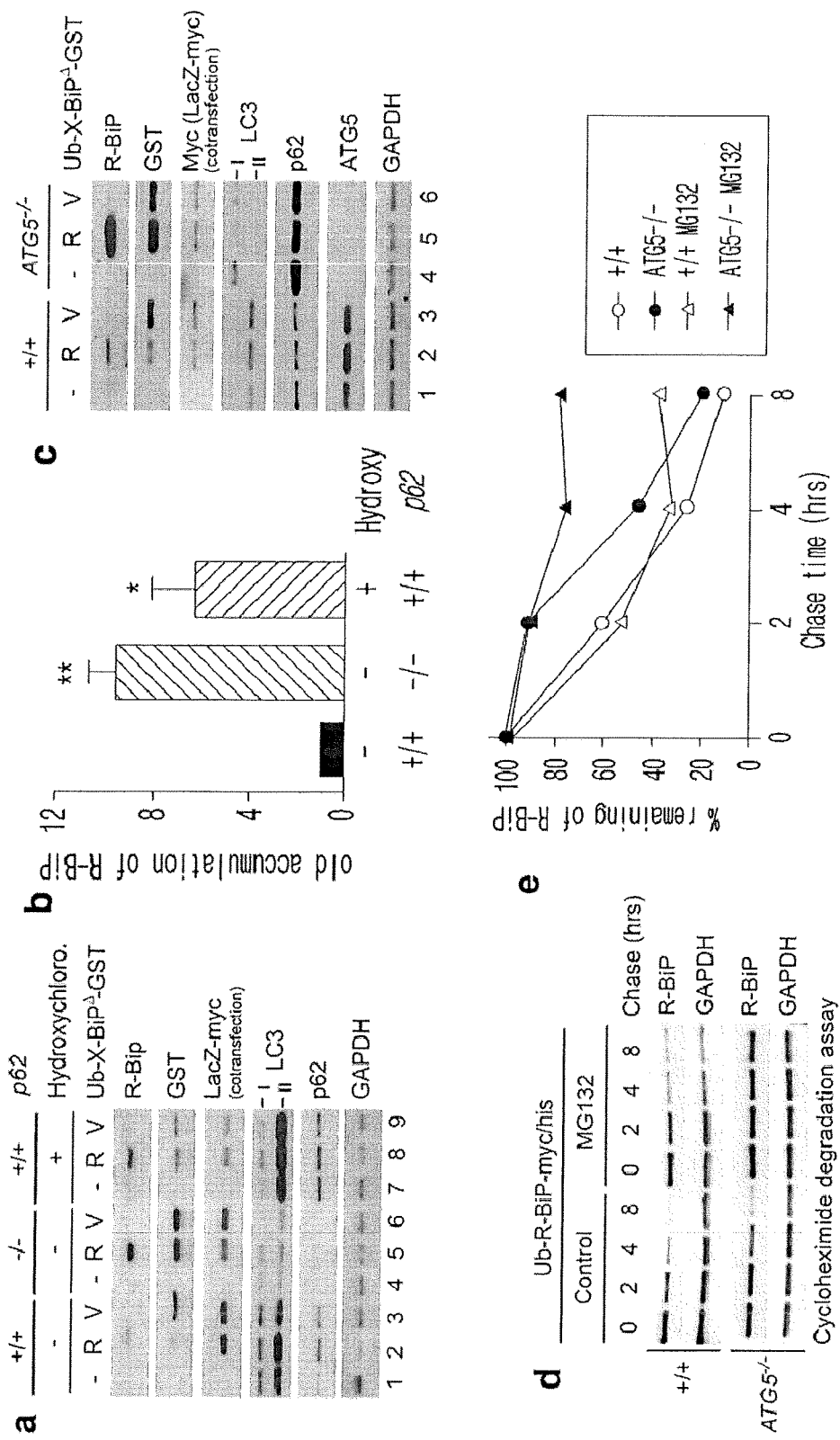

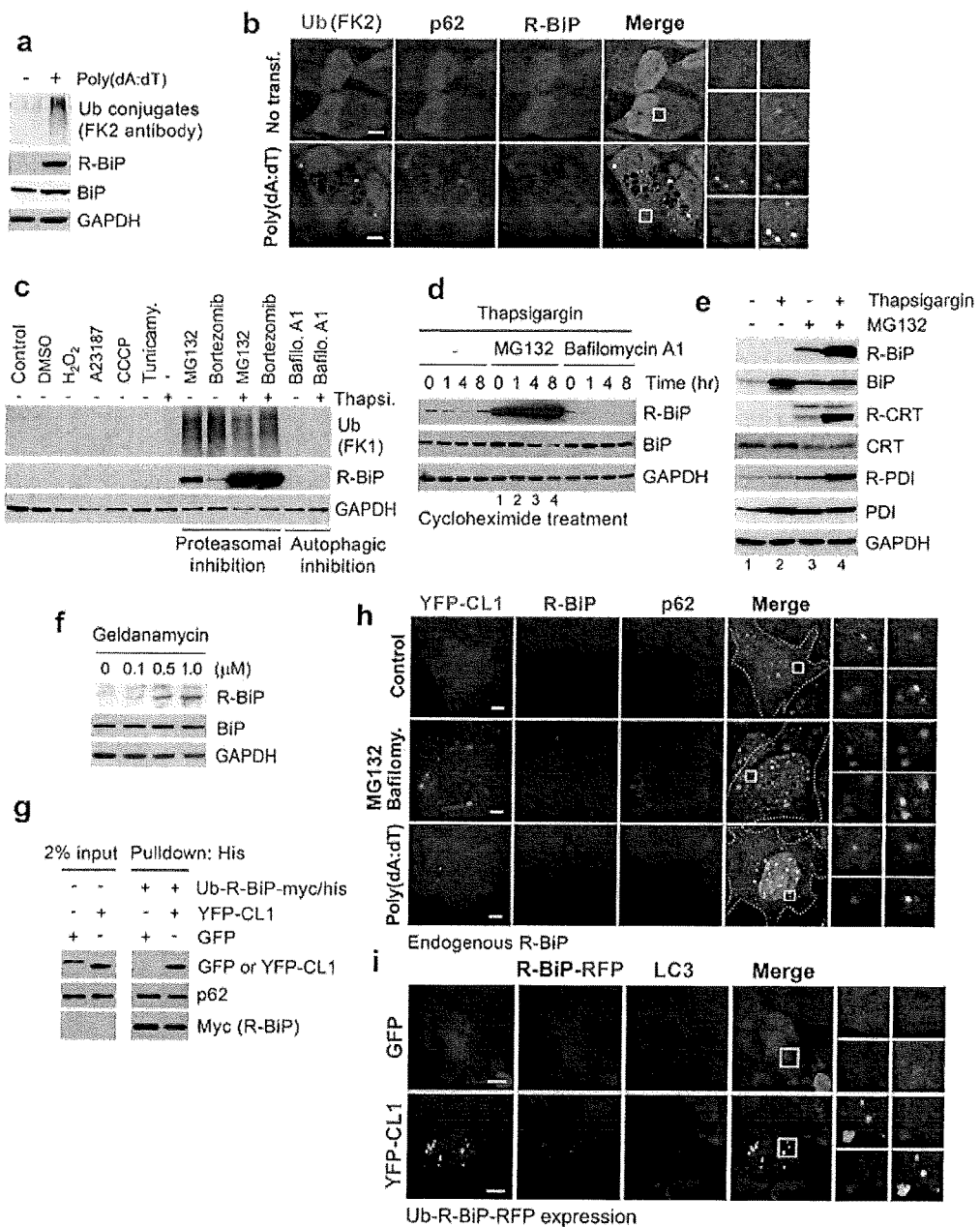
[Fig. 17]

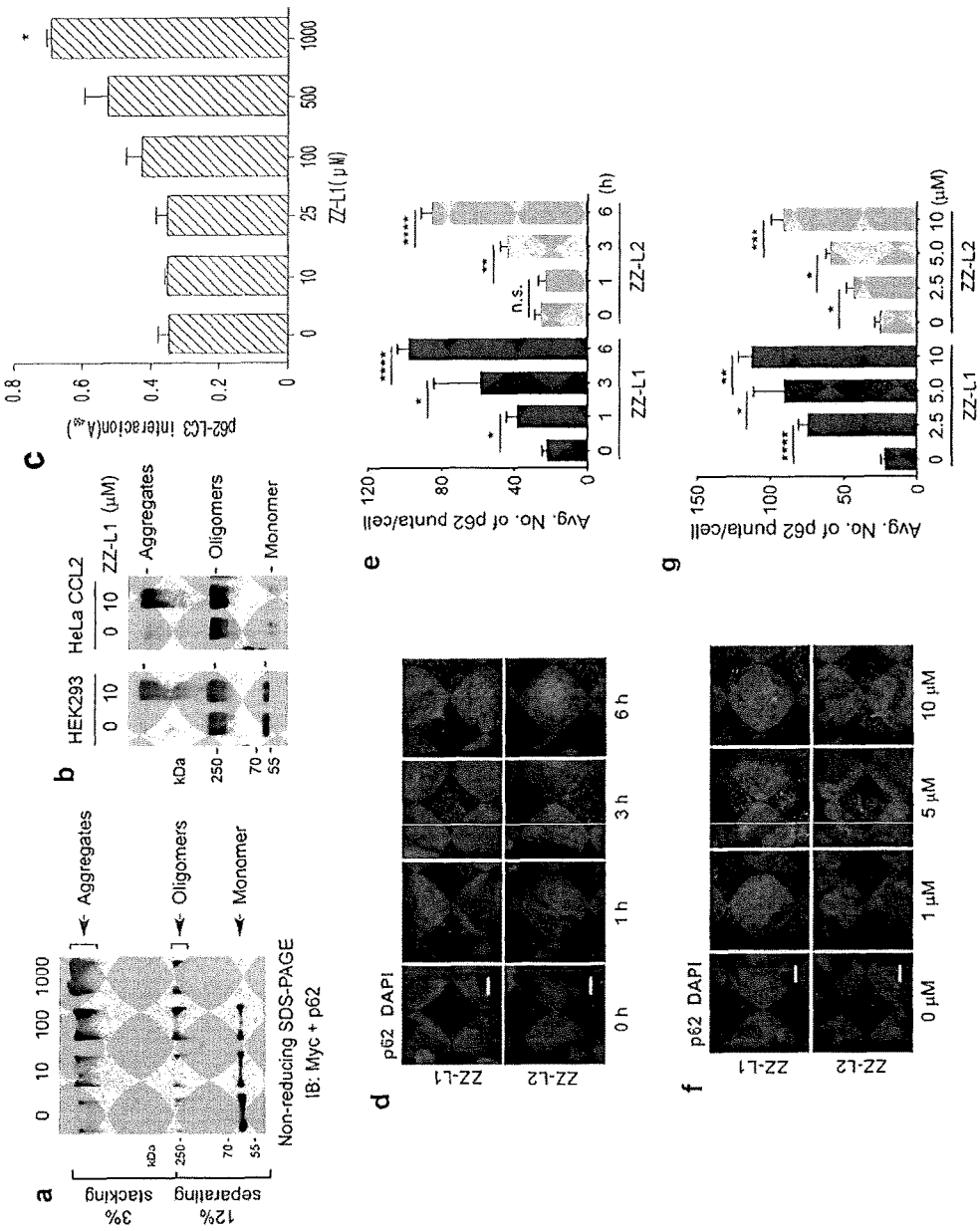
[Fig. 18]

[Fig. 19]
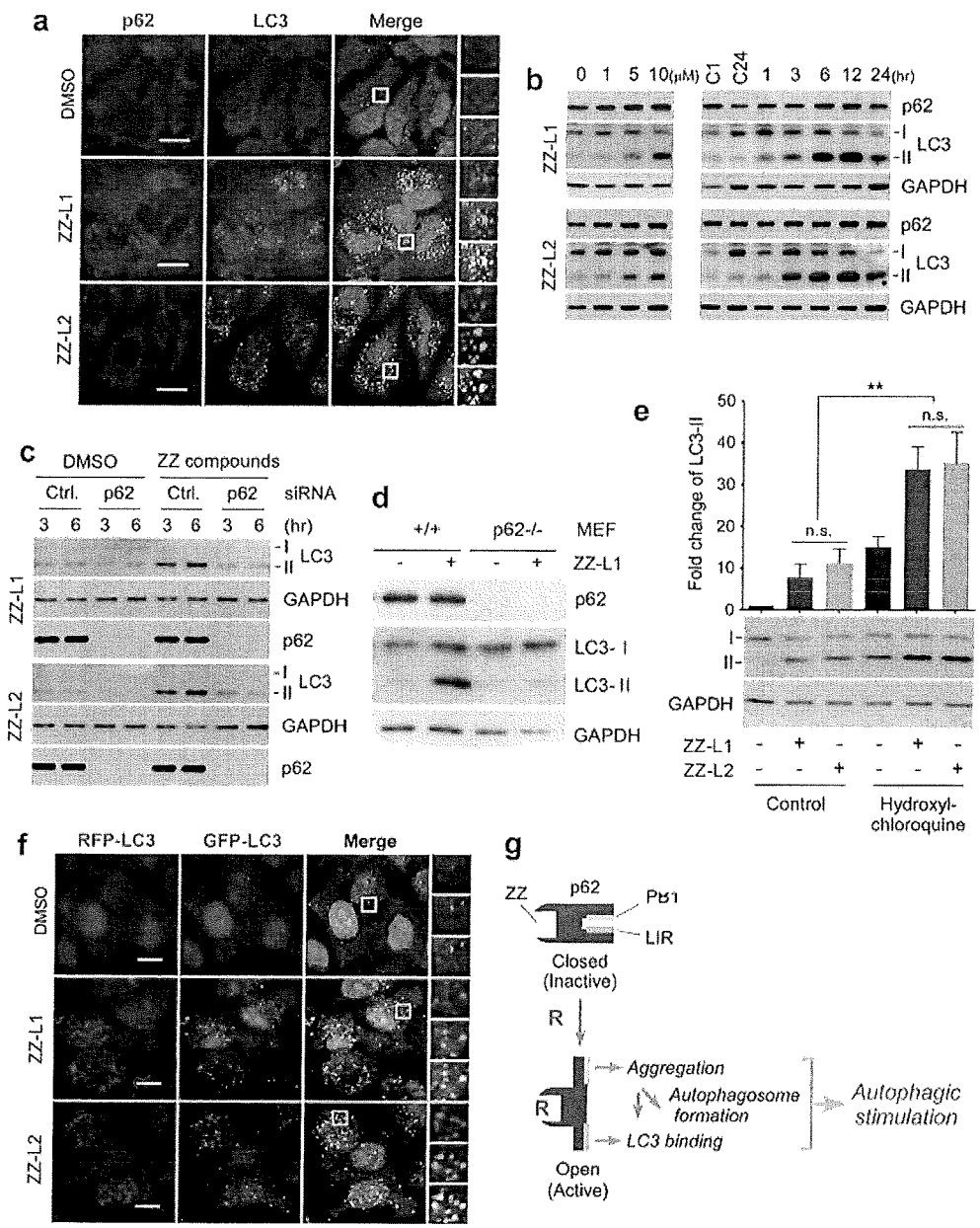

[Fig. 20]
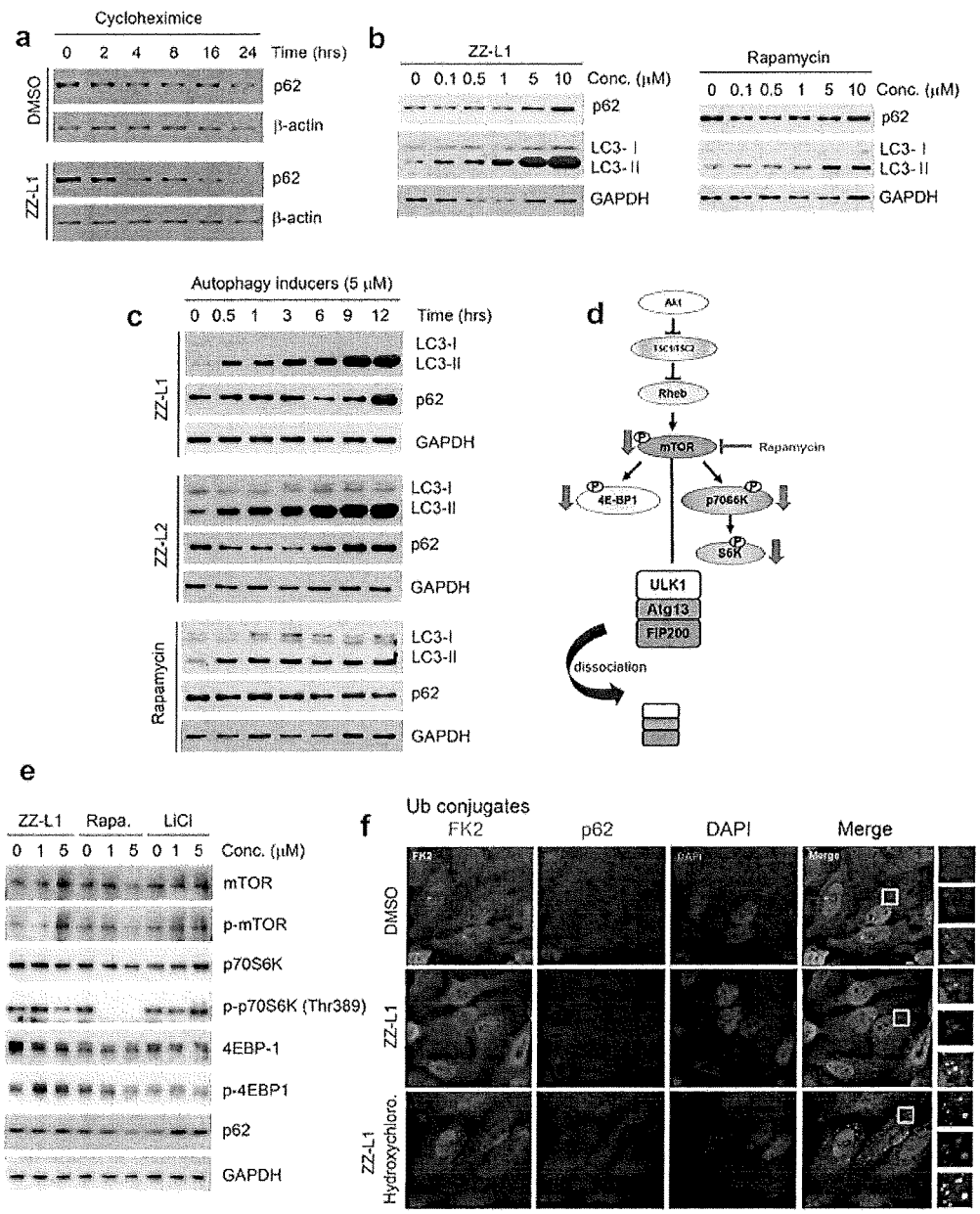

[Fig. 21]
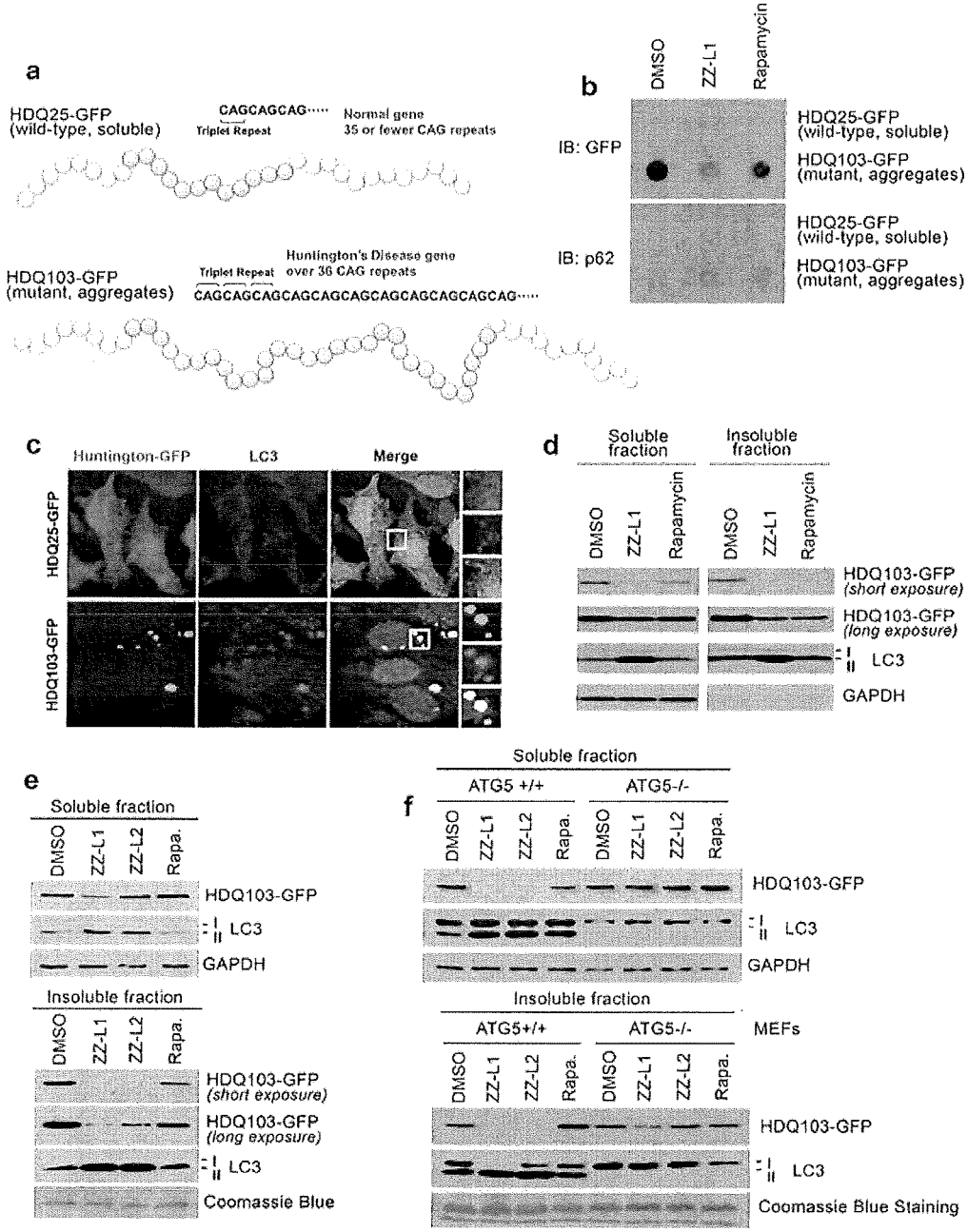

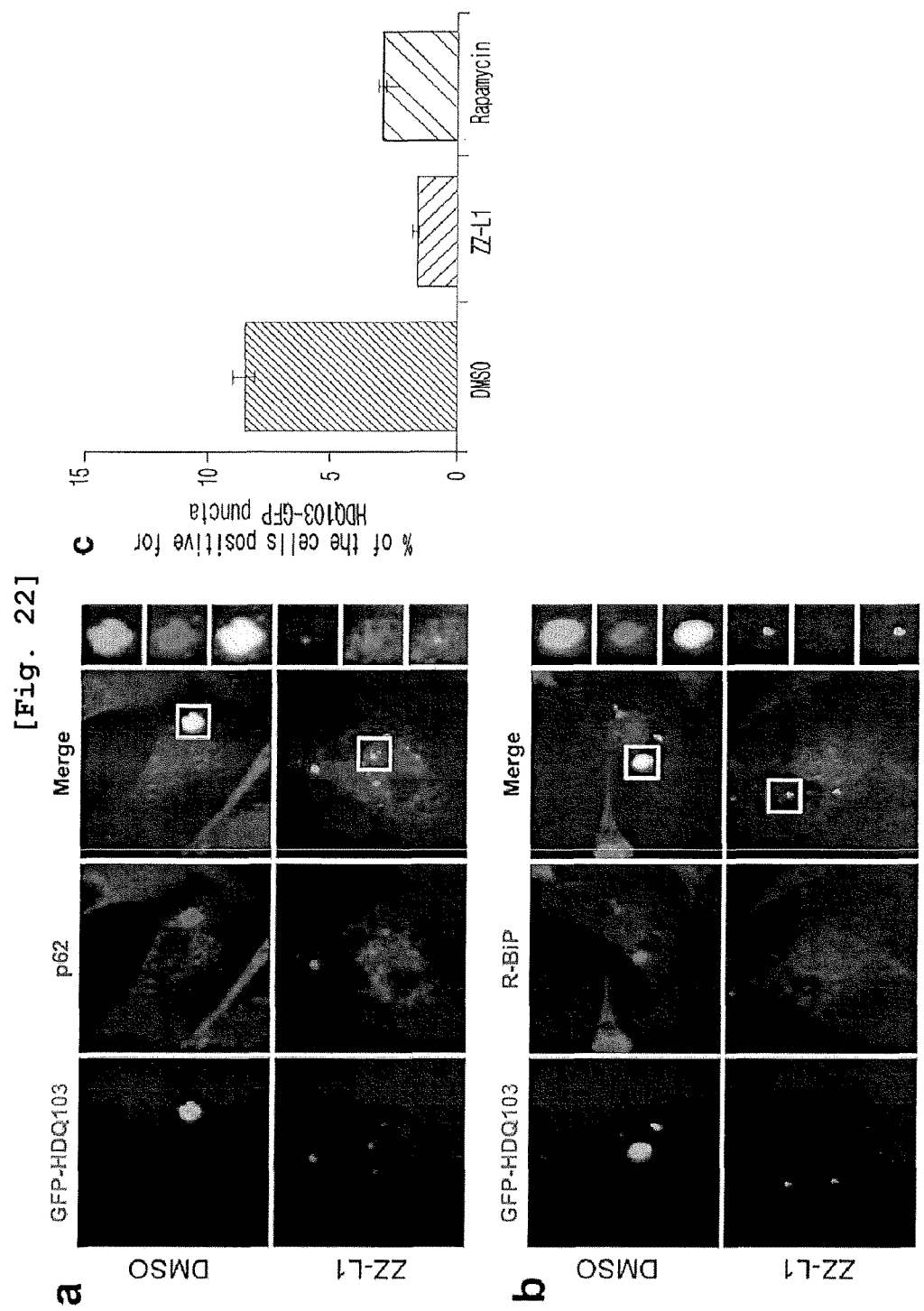

[Fig. 23]

| Chemical Property | p62-ZZ1 | P62-ZZ2 | Rapamycin |
|---|---|---|---|
| Molecular weight(kd) | 363.5 | 421.53 | 914.17 |
| pKa | 14.74 | 13.83 | 10.40 |
| Solubility (Ph7, Temp:25°C) | 3.4 mg/ml | 8.0 mg/ml | 0.25 mg/ml (in ethanol) |
| Boiling Point | 550.5±45°C | 594.6±50°C | 182°C |
| Density | 1.155±0.6 g/cm$^3$ | 1.131±0.6 g/cm$^3$ | 1.15 g/cm$^3$ |
| Polar Surface Area | 50.7 | 60.0 | 195.0 |

[Fig. 24]

| PK parameter | IV(intravenous) | | Oral | |
|---|---|---|---|---|
| | Mean | SD | Mean | SD |
| Dose(mg/kg) | 5 | | 20 | |
| $T_{max}(hr)$ | NA | | 1.1 | 0.7 |
| $T_{1/2}(hr)$ | 3.07 | 1.44 | 3.4 | 0.4 |
| $C_{max}$ | NA | | 312.6 | 37.8 |
| $AUC_{last}$ | 1024.13 | 173.07 | 1419.3 | 805.3 |
| CL(l/hr/kg) | 4.9 | 0.8 | NA | |
| $V_{ss}$(l/kg) | 11.88 | 2.38 | NA | |
| $V_z$(l/kg) | 20.55 | 6.83 | NA | |
| $MRT_{inf}(hr)$ | 2.53 | 0.89 | 4.8 | 0.5 | ns and on the ligand since N-recog-

PREVENTION AND TREATMENT OF NEURODEGENERATIVE DISEASES THROUGH AUTOPHAGY ACTIVITY MEDIATED BY A SYNTHETIC LIGAND OR ARGINYLATED BIP BINDING TO THE P62 ZZ DOMAIN

This patent application is the National Stage of International Application No. PCT/KR2016/007745 filed Jul. 15, 2016, which claims the benefit of priority from Korean Application No. 10-2015-0116015, filed Aug. 18, 2015, each of which are herein incorporated by reference in their entirety.

BACKGROUND OF THE INVENTION

1. Field of the Invention

The present invention relates to a method for the treatment of neurodegenerative disease through the regulation of autophagy activity mediated by a synthetic ligand or arginylated BIP (R-BiP) binding to the P62 ZZ domain.

2. Description of the Related Art

The N-end rule pathway is a proteolytic system where the single N-terminal residue of a protein acts as a degradation signal (FIGS. 1 and 2). The N-end rule degradation signal is exemplified by type I basic residues including Arg, Lys, and His; and type II hydrophobic residues including Phe, Leu, Trp, Tyr, and Ile (FIG. 2). These N-terminal residues bind to specific N-recognins (FIG. 3). The present inventors first discovered or cloned previously known N-recognins, namely UBR1, UBR2, UBR4, and UBR5, and found that they utilize the UBR box as a substrate recognition domain (Tasaki et al. 2005, FIG. 3). The present inventors also confirmed that the UBR box of N-recognins binds to type-I N-end rule ligands such as N-terminal Arginine (Nt-Arg) to recognize a substrate and to link a ubiquitin chain to the substrate. UBR1 and UBR2 have an N-domain which plays an important role in the binding of type-2 N-end rule ligands (Nt-Trp, Nt-Phe, Nt-Tyr, Nt-Leu, and Nt-Ile), as confirmed by the present inventors (Sriram et al., 2011). The ubiquitinized substrate produced from the binding between N-recognins and N-end rule ligands is delivered to proteasome where it is degraded. In this process, specific N-terminal residues (Nt-Arg, Nt-His, Nt-Lys, Nt-Trp, Nt-Phe, Nt-Tyr, Nt-Leu, and Nt-Ile) are the essential determinants of binding and are the active components of the ligand since N-recognins provide most of the hydrogen bonds needed to target the N-end rule substrate (FIGS. 3c and 3d) (Sriram and Kwon, 2010).

Neurodegenerative diseases are debilitating conditions that lead to progressive neuronal degeneration and/or death. These diseases are classified according to the main symptoms and the affected brain area, and include Alzheimer's disease (AD), Parkinson's disease (PD), Huntington's disease (HD), prion disease/Creutzfeldt-Jakob Disease, Scleroderma, amyotrophic lateral sclerosis (Lou Gehrig's disease), among others. Most of the known neurodegenerative diseases are caused by the accumulation of pathogenic protein aggregates due to the impairement of proteostasis. Therefore, neurodegenerative diseases belong to a group of protein misfolding disorders most notably including, Huntington's disease caused by the misfolding of the mutant huntingtin protein (Williams et al., 2008; Tsoi et al. 2012), Parkinson's disease caused by the misfolding of the mutant alpha-synuclein protein (Martin et al. 2011), Creutzfeldt-Jakob disease caused by the misfolding of the mutant prion protein (Griffith, 1967), and Lou Gehrig's disease caused by the misfolding of the the mutant SOD1 and TDP-34 proteins (Andersen et al. 2011). All these misfolded proteins can be rapidly converted into aggregates, which are toxic to neurons.

Parkinson's disease (PD) is one of the most representative neurodegenerative diseases and is caused by the loss of dopaminergic neurons. PD symptoms include resting tremor, stiffness, bradykinesia, and postural instability. Medicinal treatment of Parkinson's disease can be divided into symptomatic treatment and neuroprotective treatment. Drugs for the symptomatic treatment include levodopa, dopamine agonists, anticholinergic agents, COMT inhibitors, and amantadine while drugs for the neuroprotective treatment include anti-oxidants and MAO-B inhibitors. Among these, the most effective drug is levodopa which is the immediate precursor of dopamine and is metabolized to dopamine in the brain. Levodopa is not only metabolized by L-dopa decarboxylase but also by catechol-O-methyltransferase (COMT). Therefore, levodopa is co-administered with a COMT inhibitor to inhibit its metabolism and extend its effect and duration in blood. The dopamine replacement therapy using levodopa has been effective in treating patients with Parkinson's disease. However, once the duration of the treatment exceeds 5 to 10 years, most of the patients display side effects such as fluctuations in exercise and motor reactions, autonomic dysfunction, and postural instability; and the positive effects of levodopa treatment are no longer observed.

Tetrabenazine (TBZ) is the most common drug for the treatment of Huntington's disease. The mechanism of action of TBZ is not well known, yet it has been confirmed that TBZ inhibits the vesicular monoamine transporter in pre-synaptic neurons leading to the depletion of monoamines such as dopamine, serotonin, and norepinephrine. TBZ also acts as a weak antagonist against the D2 dopamine receptor in post-synaptic neurons. Other drugs used to treat Parkison's disease include clozapine and amantadine. Clozapine is an atypical neuroleptic agent that effectively reduces movement disorders. Amantadin acts as a NMDA receptor antagonist and is also used as a treatment for Huntington's disease due to the fact that Huntington's disease is caused by the excessive excitement of dopamine and glutamate receptors.

The treatment of Parkinson's and Huntington's disease has many limitations in terms of therapeutic efficacy and persistence since treatment is based on symptomatic and neuroprotective therapies which do not fix the fundamental causes of the diseases. Therefore, alternative treatment methods that would prevent or cure the fundamental causes of the diseases need to be developed.

Misfolded proteins linger in cells and eventually aggregate resulting in the inhibition of proteasome mediated protein degradation and thus limiting cellular functions and cause cell death. Therefore, misfolded proteins need to be promptly removed by the ubiquitin-prtoeasome system (UPS) (FIG. 4). In normal cells, the UPS minimizes cellular damage by misfolded protein. However, in aged neurons, the UPS is slowed so that the misfolded proteins accumulate leading to aggregation. In neurons of patients with degenerative brain diseases such as Huntington's and Parkinson's disease, specific mutant proteins aggregate preventing their degradation degraded by the proteasome since the aggregated proteins are to large to pass through the very narrow inner proteasome. The core technique in this invention is to effectively remove these misfolded protein aggregates causing neurodegenerative diseases by activating p62 induced autophagy.

Autophagy is a major intracellular protein degradation system essential to maintain cell homeostasis and genetic stability by degrading unfolded or damaged proteins and aged or impaired cellular organelles. Macroautophagy (hereafter referred to as autophagy) is responsible for degrading cytotoxic misfolded proteins (FIG. 4) which are recognized and sorted out by a number of selective autophagy receptors. p62/SQSTM1/Sequestosome-1 is a major selective autophagy receptor that binds to ubiquitinated misfolded proteins leading to their co-aggregation and delivery to autophagosomes (FIG. 4). p62-mediated transportation of misfolded proteins to autophagosomes requires p62's ability to oligomerize. Through oligomerization, p62 not only packages its cargo but also deliver the cargo to the autophagosome formation site for autophagic co-degradation. At this time, the unfolded proteins are concentrated together to reduce the volume making them easier to be degraded by autophagy. The PB1 domain mediates the self-oligomerization of p62 through an unknown the mechanism. The unfolded protein-p62 conjugate delivered to the autophagosome can be degraded by lysosomal enzymes when the autophagosome binds to a lysosome (FIG. 4). By this mechanism, autophagy can maintain cell homeostasis by regulating intracellular changes in damaged proteins and cellular organelles. When autophagic function is weakened, the accumulation of the midfolded proteins is increased, resulting in the neurodegenerative disease. A key technique of the present invention is to provide a method to activate intracellular autophagy.

Studies on the efficient activatation of autophagy to treat degenerative brain diseases have been actively pursued. MTOR is an autophagy inhibitor. The activation of autophagy using the mTOR inhibitor rapamycin is the most widely used method. In an AD animal model over-expressing APP, amyloid beta (Ab) and tau were eliminated using rapamycin treatment (Caccamo et al., 2010); in an Ad animal model over-expressing tau, tau was eliminated using rapamycin treatment (Rodriguez-Navarro et al., 2010); and in a PD mouse model, the over-expressed alpha-synuclein protein coagulum was eliminated using rapamycin treatment (Webb et al., 2003). In a HD mouse, the huntingtin coagulum was efficiently eliminated by using CCI-779, a rapamycin-like substance, improving animal cognitive behavior (Ravikumar et al., 2002). However, since mTOR plays a very important role in various intracellular pathways including NF-kB, using mTOR inhibitors as an autophagy activator is limited.

There are other studies using autophagy activators other than mTOR inhibitors to induce autophagy. Specifically, in a HD mouse model, the huntingtin coagulum was successfully eliminated by using Rilmenidine an mTOR independent activator of autophagy (Rose et al., 2010).

In a prion disease mouse model, the over-expressed mutant prion (PrPSc) coagulum was successfully eliminated by using lithium, an inositol monophosphatase inhibitor, to activate autophagy (Heiseke et al., 2009). In addition, the over-expressed alpha-synuclein protein coagulum was eliminated by using lithium in a PD mouse model (Sarkar et al., 2005); and in an amyotrophic lateral sclerosis (ALS) mouse model, the over-expressed mutant SOD1 G93A coagulum was eliminated from the brain using lithium (Feng et al., 2008; Pizzasegola et al., 2009). Trehalose, a plant extract, is known to activate autophagy independent of the mTOR pathway and was used to eliminate mutant huntingtin protein from brain in a HD mouse model (Sarkar et al., 2007). In addition, trehalose was used to improve motor ability and longevity in a PD mouse model (Tanaka et al., 2004), as well as to eliminate the over-expressed A30P and A53T mutant alpha-synuclein coagulums in a diffent PD mouse model (Sarkar et al., 2007). Finsetin, a natural flavone, is known to activate autophagy through TORC1 and AMPK and was used to improve or alleviate the symptoms of degenerative brain disease in an animal model (Maher et al., 2011). However, there is still a limit on using these additional autophagy activator because they have other important roles in the intracellular signal transduction system.

As described above, there is no effective therapeutic agent to treat most degenerative brain diseases such as Huntington's disease that do not have extensive side effects. The mTOR inhibitor, which is the most commonly used compound as an autophagy activator, is inadequate as a therapeutic agent because mTOR plays a wide role in regulating overall gene expression in cells therefore inhibiting mTOR affects many essential biological pathways not just autophagy. The present invention provides a technique to eliminate the misfolded protein coagulum, which is a causative factor of degenerative brain diseases, by activating p62 which plays a crucial role in delivering the misfolded protein coagulum directly to autophagosome for eliminatation. Activating authophagy through p62 does not affect additional biological pathways as does inhibiting mTOR, therefore reducing potential side effects.

The pharmacokinetics and key technologies of the present invention are summarized in FIG. 1. Particularly, malignant misfolded proteins such as mutant huntingtin and alpha-synuclein are coagulated and grow into oligomeric coagulum (①, ②), fibrillar coagulum (③) and eventually inclusion body (④). Young neurons produce a large amount of Nt-Arg through N-terminal arginylation (⑤) of vesicle chaperones such as BiP, and then the arginylated BiP (R-BiP) is translocated into the cytoplasm and binds to the misfolded protein (⑥). As a ligand, the Nt-Arg of R-BiP binds to the p62 ZZ domain (⑦), and the normally inactivated closed form of p62 is changed to an open form, leading to structural activation (⑧). As a result, PB1 and LC3-binding domains are exposed. The PB1 domain facilitates p62 oligomerization (⑨) leading to the aggregation of p62 together with R-BiP and misfolded proteins and their targeting to the autophagosome formation site (⑩). p62 interaction with LC3 on the membrane of growing phagophore results in the integration of p62-R-BiP-cargo into autophagosomes (⑩) and lysosomal proteolysis. Since autophagy proteolysis including steps ⑤-⑪ is very strong in young neurons, cytotoxic protein coagulums (①-⑤) do not accumulate. However in aged neurons, autophagy proteolysis including steps ⑤-⑪ is weakened, and protein coagulums (①-⑤) accumulate leading to cell ctyotoxicity. In this invention, p62 is intentionally activated (⑫, ⑬) using a low mass ligand of p62 ZZ domain to effectively remove huntingtin and alpha-synuclein protein coagulums. Particularly, in step ⑫, the p62 ligated with the ligand accelerates the oligomerization of p62-R-BiP-misfolded proteins (⑨) and the formation of autophagy coagulum (⑩). In step ⑬, the ligand-p62 conjugate acts as an autophagy activator (⑭) to induce the synthesis of LC3 and the conversion of LC3-I into LC3-II in order to accelerate the formation of autophagosomes (⑮).

As a result their research and literature review, the present inventors propose that p62 is a first-in-class target for autophagy activation (FIG. 1, ⑧). No previous studies proposing p62 as a drug target for autophagy activation or the removal of protein coagulum in degenerative brain diseases have been done. Therefore, the present inventors request a patent to develop novel therapeutic agents targeting p62 as a method to treat neurodegenerative disease by activating autophagy.

In the course of developing novel drugs to prevent and treat neurodegenerative diseases by targeting p62 as means to activate autophagy, the present inventors have confirmed that p62 ZZ domain binding ligands can activate autophagy through the mechanism described above resulting in the efficient elimination of mutant huntingtin and alpha-synuclein protein coagulums, confirming a pharmaceutical composition for the treatment or prevention of neurodegenerative diseases, and a method to regulate the same, leading to the completion of the present invention.

SUMMARY OF THE INVENTION

It is an objective of the present invention to provide a pharmaceutical composition for the prevention and treatment of neurodegenerative disease diseases comprising a ligand binding to the p62 ZZ domain as an active ingredient.

It is another objective of the present invention to provide a food supplement for the prevention and improvement of neurodegenerative diseases comprising a ligand binding to p62 ZZ domain as an active ingredient.

It is also an objective of the present invention to provide a method to induce p62 oligomerization and structural activation (1); to activate autophagy (2); and to eliminate misfolded protein coagulum (3), containing the step of treating the ligand binding to p62 ZZ domain to cells.

To achieve the above objectives, the present invention provides a pharmaceutical composition for the prevention and treatment of neurodegenerative diseases comprising a ligand binding to p62 ZZ domain as an active ingredient.

The present invention also provides a food supplement for the prevention and improvement of neurodegenerative disease comprising a ligand binding to p62 ZZ domain as an active ingredient.

In addition, the present invention provides a method to induce p62 oligomerization and structural activation (1); to increase p62-LC3 binding (2); to increase the transportation of p62 to autophagosomes (3); to activate autophagy (4); and to eliminate misfolded protein coagulum (5), containing the step of treating the cells with the ligand that binds to the the p62 ZZ domain.

Advantageous Effect

The present invention relates to a p62 activity regulator, an autophagy activator, and a therapeutic agent for degenerative brain diseases comprising a ligand binding to the p62 ZZ domain as an active ingredient. The ligand binding to the p62 ZZ domain of the present invention includes X-11 peptide (X=Nt-Arg, Nt-Phe, Nt-Tyr, Nt-Trp), Arg-Ala (RA), Trp-Ala (WA), ZZ-L1, and ZZ-L2, and Nt-arginylated BiP (R-Bip). In particular, the active ingredients of X-11 peptide, Arg-Ala, Trp-Ala, and R-BiP include Nt-Arg, Nt-Phe, Nt-Tyr, and Nt-Trp. Therefore, the ligand binding to the p62 ZZ domain can be effectively used as an active ingredient for a composition for the prevention or treatment of neurodegenerative diseases through the regulation of autophagy.

BRIEF DESCRIPTION OF THE DRAWINGS

The application of the preferred embodiments of the present invention is best understood with reference to the accompanying drawings, wherein:

FIG. 1 is a diagram illustrating the drug target and mechanism proposed in the present invention.

FIG. 2 is a schematic diagram illustrating the N-terminal proteolysis pathway. In this pathway, an N-terminal residue such as Nt-Arg acts as a degradation ligand and can be recognized by N-recognins and then bound, resulting in the degradation of the substrate. In the conventional pathway, Nt-Arg induces ubiquitination, by which targeting of the substrate to proteasome is enhanced. In this invention, it was found that Nt-Arg not only binds to p62 activating it, but also activates the autophagic pathway.

Figure 3B:
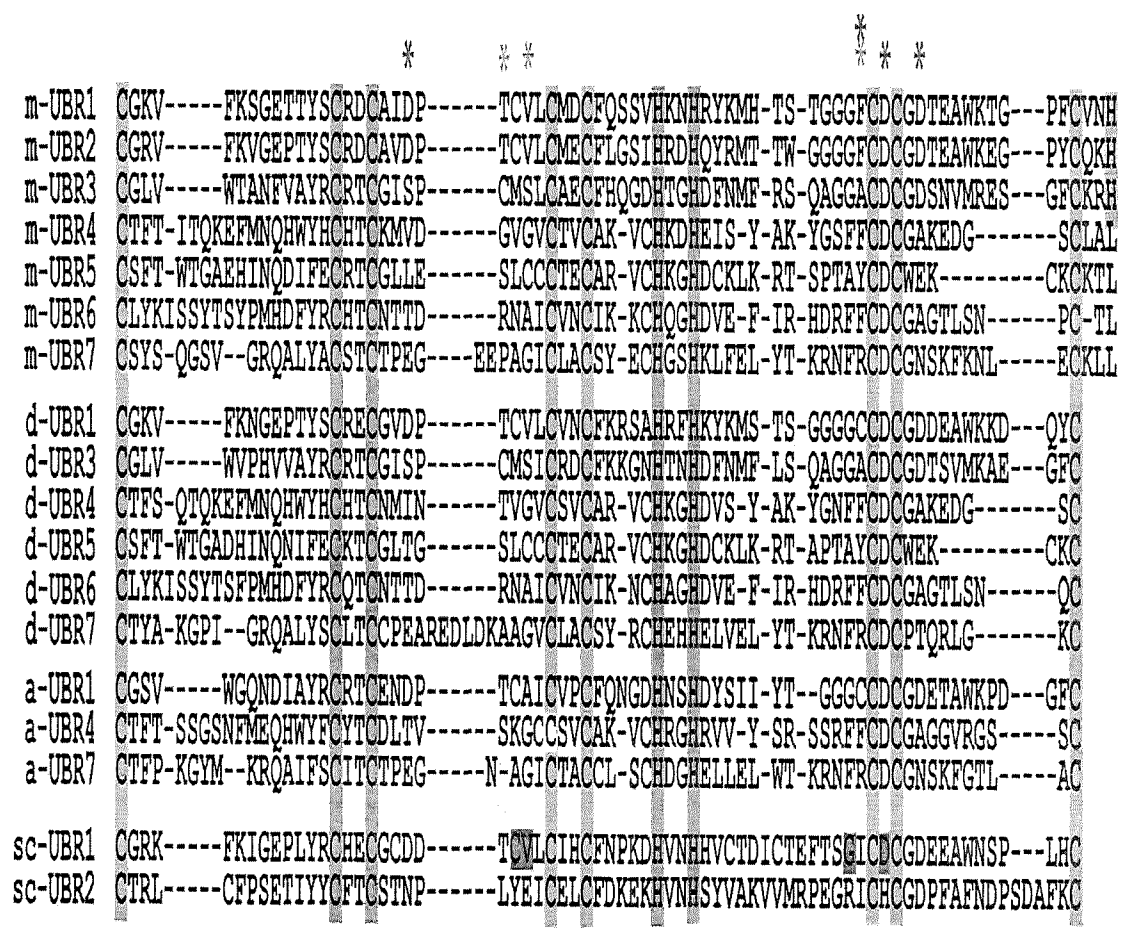

FIG. 3 is a diagram illustrating the structures and sequences of N-recognins in the N-terminal proteolysis pathway (N-end Rule pathway). (a): schematic diagram illustrating the primary structure of the UBR box protein group (UBR1-UBR7). This group has a UBR box that can bind to Nt-Arg, among which UBR1, UBR2, UBR4, and UBR5 have been confirmed to bind to Nt-Arg. (b): diagram comparing UBR box sequences. (c, d): crystal structure of UBR box of UBR1.

FIG. 4 is a schematic diagram illustrating how the ubiquitin-proteasome system (UPS), chaperone-mediated autophagy, and macroautophagy cooperate with each other to remove misfolded proteins.

FIG. 5 is a diagram illustrating the selective binding of p62 to N-ligands such as N-end rule novel N-recognins, Nt-Arg and Nt-Trp. (a): schematic diagram wherein the kinds of proteins that bind to a synthetic peptide loaded with an N-degron in a rat tissue extract were investigated, in order to indentify a novel N-recognin. (b, c): results of silver staining of those proteins obtained by X-peptide pull down performed with rat testis extracts. (d): results of iTRAQ (Isobaric tags for relative and absolute quantitation) performed with those proteins obtained by X-peptide pull down. (e-i): results of immunoblotting performed with those proteins obtained by X-peptide pull down.

FIG. 6 is a diagram illustrating the results of measuring the binding force of p62 to Nt-Arg (Kd, 40 nM) and Nt-Phe (Kd, 3.4 µM) by using Biacore assay.

FIG. 7 is a diagram illustrating that p62 binds to N-end rule ligands through its ZZ domain and also presents the comparison of the primary structures of ZZ and UBR box domains. (a, c, e, g, i): schematic diagrams illustrating various fragments of p62. (b, d, f, h, j): results of X-peptide pull down analysis performed with those p62 fragments. (1): results of the comparison of the primary structures of the p62 ZZ domain and the UBR box.

FIG. 8 is a diagram illustrating that Arg-Ala induces p62 self-oligomerization and increases the binding of p62 to LC3. (a-c): analysis of p62 self-oligomerization. To investigate whether or not the p62 self-oligomerization and coagulum formation could be induced when the N-ligand Arg-Ala is bound to p62 ZZ domain, an in vitro oligomerization assay was performed with HEK293 cell lysate expressing the full length p62 in a non-reducing SDS-PAGE. (d): results of an in vitro p62 oligomerization assay performed by using a p62 ZZ mutant that could not bind to the Arg-11 peptide. (e): To investigate whether or not the p62 PB1 domain was involved in the formation of p62 coagulum, the aggregation ability of the D69A mutant was evaluated. (f-h): ELISA was performed to investigate the effect of Arg-Ala on the binding of p62 to LC3. (i): schematic diagram illustrating the inducement of structural activation of p62 by the binding of Nt-Arg to the p62 ZZ domain.

FIG. 9 is a diagram illustrating the comparison of the primary protein sequences of the endoplasmic reticulum chaperones. These proteins lose their signal peptides when they enter the endoplasmic reticulum after translation. At this time, N-ligands are exposed in the mature protein (indicated as a box). When misfolded proteins accumulate in the cytoplasm, the chaperones move into cytoplasm and are N-terminally arginylated.

FIG. 10 is a diagram illustrating the screening of endoplasmic reticulum proteins obtaining Nt-Arg as an N-ligand through N-terminal arginylation. (a): schematic diagram illustrating N-terminal arginylation. When cells are stressed by the accumulation of misfolded proteins, chaperones move into the cytoplasm, leading to the N-terminal arginylation by ATE1 R-transferase. (b): results of peptide binding assay performed to measure the specificity and binding force of R-BiP antibody. (c): dot blot assay using R-BiP antibody. (d): ATE1 R-transferase isomerase was over-expressed and then R-BiP formation was confirmed by using the R-BiP antibody above. (e): When ATE1 was knocked down using siRNA, it was confirmed that R-BiP formation was reduced.

FIG. 11 is a diagram illustrating that the N-terminal arginylation of BiP, CRT, and PDI was mediated by ATE1. (a): Arginylation was examined by expressing Ub-X-BiP-flag (X=Glu or Val). (b): schematic diagram illustrating the formation of the recombinant protein Ub-X-Bip-myc/his structure. (c): X-BiP arginylation on Nt-G19 was confirmed by using the structure above. (d): It was confirmed that R-BiP was not produced in ATE1 knock-out cells. (e): Using thapsigargin, which causes ER stress, it was confirmed that R-BiP was not produced by ER stress but was the product of the enzyme reaction caused by ATE1 R-transferase. (f): It was confirmed that the R-BiP generated above moved to the cytoplasm in a large volume by using cell fractionation. (g): It was confirmed that the R-BiP in the cytoplasm was not degraded relatively as compared with the non-arginylated BiP in endoplasmic reticulum by using a cycloheximide proteolysis technique. (h): N-terminal arginylation of CRT and PDI induced by ATE1 was investigated. As a result, it was confirmed that R-CRT and R-PDI were produced when ATE1 isoenzyme was over-expressed.

FIG. 12 is a diagram illustrating the R-BiP generation was induced by external DNA in the cytoplasm. (a, b): R-BiP generation was specifically induced when double stranded DNA (dsDNA) was introduced to the cytoplasm. (b, c): R-CRT generation was also induced when dsDNA was introduced in the cytoplasm similarly to R-BiP. (d): The R-BiP generated by dsDNA moved into the cytoplasm, which was confirmed by cell fractionation. (e-g): R-BiP, R-CRT, and P-PDI were generated as part of the innate immune response to invading DNA using poly (dA:dT) mimicking a pathogen (virus or bacteria) containing DNA. (f): Autophagy was also activated along with the process above.

FIG. 13 is a diagram illustrating that R-BiP is transferred to autophagosomes along with p62. (a): R-BiP was transferred to the cytoplasm and accumulated in puncta, which was confirmed by immunohistochemical staining. (b-d): The R-BiP puncta was colocalized with P62 puncta (a, c) and also colocalized with LC3 (b-d). (e): It was confirmed that BiP was transferred to LC3 positive autophagosome in mouse embryo heart. (f-h): When ATE1 or BiP was knocked-down using siRNA, R-BiP did not migrate to autophagosome. When p62 was knocked-down, a similar result was obtained.

FIG. 14 is a diagram illustrating that Nt-Arg is required when R-BiP is transferred to autophagosome. (a): schematic diagram illustrating the generation of X-BiP-GFP according to the over-expression of Ub-X-BiP-GFP recombinant protein (X=Arg, Glu, or Val) in cells. (b): The migration of the recombinant protein to autophagosomes was investigated using immunostaining. (c): R-BiP was transferred to autophagosomes, but Val-BiP (Nt-G19 was substituted with Val, so that it could not be used as a substrate for arginylation) was not transferred to autophagosomes because of the lack of Nt-Arg. (d): Similar results were obtained when the intracellular location of R-BiP was compared with that of LC3 puncta. (e): After overexpressing Ub-X-BiP$^\Delta$ (FIG. 14a), in which most of BiP was eliminated and 19~124 residues were left, the intracellular location of X-BiP$^{\Delta D}$ was examined using immunostaining. (f): Similar results were obtained when the intracellular locations of X-BiP and LC3 were examined using immunostaining.

FIG. 15 is a diagram illustrating that Nt-Arg of R-BiP binds directly to the p62 ZZ domain. (a, b): An X-peptide pull down assay was performed to investigate whether or not Nt-ARg of R-BiP could bind to the p62 ZZ domain. (c, d): The R-BiP peptide pulled down p62 from a cell extract, but E-BiP or V-BiP peptide did not. (e): schematic diagram illustrating the p62 fragments prepared to investigate the binding region of p62 for Nt-Arg of R-BiP. (f): A pull down assay was performed with the p62 fragments and R-BiP peptide. As a result, Nt-Arg of R-BiP was bound to the p62 ZZ domain. (g): Only the p62 ZZ domain was cut out and named as p62-ZZ83-175-GST and p62-ZZ (D129A)83-175. (h): GST pull down assay was performed with the P62 fragments. (i): When p62-ZZ83-175-RFP and ubiquitin-X-Bip19-124-GFP were over-expressed in MEF cells simultaneously, Arg18-Bip19-124 was colocalized with p62-ZZ83-175-RFP showing puncta formation, while Val19-Bip19-124-GFP was not colocalized with p62-ZZ83-175-RFP and did not show puncta formation.

FIG. 16 is a diagram illustrating that R-BiP is decomposed by p62-dependent autophagy action. (a, b): Ub-X-BiP$^\Delta$-GST was constructed, which was over-expressed in +/+ and p62−/− cells, followed by BiP degradation assay. (c) R-BiP of Ub-X-BiP$^\Delta$-GST was not decomposed but accumulated in autophagy deficient ATG5−/− cells. (d, e): A cycloheximide proteolysis quantification assay was performed with Ub-R-BiP-myc/his. As a result, it was confirmed that R-BiP was highly stabilized in cells.

FIG. 17 is a diagram illustrating that R-BiP is generated by ubiquitinized proteins in the cytoplasm and then bound to misfolded proteins in the cytoplasm and delivers them to autophagy. (a): Immunoblotting was performed with HeLa cells treated with poly (dA:dT). As a result, it was confirmed that ubiquitin-bound intracellular proteins were accumulated as R-BiP was generated. (b): Some of ubiquitinized intracellular proteins were transferred to p62 as puncta and R-BiP was colocalized within that structure. (c): Cells were treated with various chemicals, followed by immunoblotting to investigate R-BiP formation. As a result, it was confirmed that R-BiP formation was induced by the proteasome inhibitor. (d, e): When cells were treated with the proteasome inhibitor and thapsigargin causing stress in the endoplasmic reticulum simultaneously, the production of R-BiP, R-CRT, and R-PDI was strongly induced. (f): Cells were treated with geldenamycin, the Hsp90 inhibitor, to accelerate the generation of misfolded proteins in cells. As a result, it was confirmed that the production of R-BiP was induced. (g): YFP-CL1 which is the unfolded model substrate was over-expressed, resulting in the direct conjugation with R-BiP. (h, i): Immunofluorescence staining was performed to confirm that YFP-CL1 was transferred to autophagy vacuole and R-BiP and p62 were colocalized in that structure.

FIG. 18 is a diagram illustrating that the small compounds ZZ-L1 and ZZ-L2 increase p62 oligomerization and binding to LC3. (a, b): The cell extracts over-expressing p62 were treated with ZZ-L1, followed by in vitro oligomerization assay to measure P62 coagulum. (c): It was investigated whether or not ZZ-L1 could induce the activation of P62 in the same manner as Arg-Alg. As a result, it was confirmed that the binding of p62 to LC3 was increased by ZZ-L1 dose-dependently (0, 10, 25, 100, 500, and 1000 μM). (d-f): Immunofluorescence confocal microscopy was performed to investigate whether or not ZZ-L1 and ZZ-L2 could induce p62 puncta formation.

FIG. 19 is a diagram illustrating that ZZ-L1 and ZZ-L2 are autophagy activators. (a): It was confirmed by immunofluorescence staining that ZZ ligands could accelerate the formation of not only p62 autophagic puncta but also LC3 autophagic puncta in HeLa cells, indicating that the ZZ ligand can function as an autophagy activator. (b): Western blotting was performed to investigate the effect of ZZ-L1 and ZZ-L2 on autophagy. (c): The increase of LC3 and the formation of LC3-II were induced by the ZZ compounds ZZ-L1 and ZZ-L2 transfected si-control. However, that effect was suppressed by knocking p62 down. (d): In a similar experiment using +/+ and p62−/− cells, it was confirmed that ZZ-1 (5 mM) was not functioning as an autophagy activator in p62−/− cells. (e): ZZ ligand treated cells were treated with hydroxychloroquine (HCQ), an autophagy inhibitor, followed by immunoblotting to quantify LC3. (f): HeLa cells were stably transfected with RFP-GFP-LC3 which was prepared by combining acid-sensitive GFP and acid-insensitive RFP, followed by autophagy dynamic analysis by the same manner described above. (g): schematic diagram illustrating that the p62 activated by ZZ ligands was functioning as an autophagy activator.

FIG. 20 is a diagram illustrating that p62 in combination with a ZZ ligand activates autophagy independent of mTOR. (a): HeLa cells were treated with ZZ-L1, followed by cycloheximide proteolysis assay. As a result, it was confirmed that p62 degradation was accelerated by ZZ-L1. (b, c): HeLa cells were treated with ZZ ligand and rapamycin at different concentrations over the different treatment times in order to compare the effect and mechanism as autophagy activators between them. Then, LC3 generation and LC3-II conversion were compared. (d): schematic diagram illustrating that rapamycin acted as an mTOR (mammalian Target of Rapamycin) inhibitor. When mTOR was inhibited, autophagy key regulators (ULK, Beclin, etc.) were activated, leading to the increase of LC3 synthesis and LC3-II conversion, resulting in the increase of autophagosome production. (e): HeLa cells were treated with ZZ ligands or rapamycin. Then, the phosphorylation of p70S6K regulated by mTOR was investigated. (f): An immunofluorescence assay was performed to investigate whether or not ZZ ligands could increase the migration of ubiquitinized intracellular proteins to autophagy. As a result, it was confirmed that 5 mM ZZ-L1 induced the migration of the ubiquitinized proteins to autophagy vacuole. When hydroxychloroquine, an autophagy inhibitor, was treated thereto, the ubiquitinized proteins were accumulated in autophagic vacuoles.

FIG. 21 is a diagram illustrating that the mutant huntingtin protein coagulum is eliminated by the ZZ ligand. (a): schematic diagram illustrating the wild-type huntingtin (HDQ25-GFP) and the mutant huntingtin (HDQ103-GFP; CAG repeats 103 times). (b): The cells over-expressing huntingtin proteins were treated with 10 mM ZZ-L1 or 1 mM rapamycin, followed by dot blot assay to investigate the residual huntingtin proteins in the cells. (c): HeLa cells over-expressing HDQ103-GFP protein coagulum were treated with 10 mM ZZ ligand, followed by immunofluorescence staining. (d): Cells were divided by the soluble fraction in 0.5% Triton X-100 and the insoluble fraction (including coagulum), followed by immunoblotting. As a result, it was confirmed that the unfolded huntingtin protein was efficiently removed from the ZZ-L1 treated coagulum fraction. (e): HeLa cells were treated with ZZ-L1, ZZ-L2, and rapamycin, followed by immunoblotting. (f): +/+ and ATG5−/− cells were treated with 10 mM ZZ ligand and 1 mM rapamycin, followed by immunoblotting.

FIG. 22 is a diagram illustrating the colocalization of R-BiP and p62 in the inclusion body formed by HDQ103-GFP huntingtin protein coagulum. (a, b, c): HeLa cells over-expressing HDQ103-GFP protein were treated with 10 mM ZZ ligand, followed by immunofluorescence staining.

FIG. 23 is a diagram illustrating the comparison of chemical characteristics of p62-ZZ1, p62-ZZ2, and rapamycin.

FIG. 24 is a diagram illustrating the pharmacokinetic profile of p62-ZZ1 in a mouse.

DESCRIPTION OF THE PREFERRED EMBODIMENTS

Hereinafter, the present invention is described in detail.

The present invention provides a method to activate p62 function by using a ligand binding to p62 ZZ domain as an active ingredient.

The present invention also provides an autophagy activator comprising a ligand binding to p62 ZZ domain as an active ingredient.

The present invention further provides a method to eliminate unfolded protein coagulum by using a ligand binding to p62 ZZ domain as an active ingredient.

In addition, the present invention provides a pharmaceutical composition for the prevention and treatment of neurodegenerative diseases comprising a ligand binding to p62 ZZ domain as an active ingredient.

The said p62 is composed of the amino acid sequence represented by SEQ. ID. NO: 1. The said ZZ domain characteristically contains 128 to 163 residues of the amino acid sequence of the p62 protein represented by SEQ. ID. NO: 1.

The ligand above contains the following peptides. In the ligands represented by SEQ. ID. NO: 2~NO: 9 below, the active ingredient that could bind directly to p62 ZZ domain was N-terminal residue of Nt-Arg (formula 1), Nt-Phe (formula 2), Nt-Trp (formula 3), or Nt-Tyr (formula 4):

```
SEQ. ID. NO: 2:
Arg-Ala;

SEQ. ID. NO: 3:
Phe-Ala;

SEQ. ID. NO: 4:
Trp-Ala;

SEQ. ID. NO: 5:
Tyr-Ala;

SEQ. ID. NO: 6:
Arg-Ile-Phe-Ser-Thr-Ile-Glu-Gly-Arg-Thr-Tyr-
Lys (R-11);
```

-continued

SEQ. ID. NO: 7:
Trp-Ile-Phe-Ser-Thr-Ile-Glu-Gly-Arg-Thr-Tyr-Lys (W-11);

SEQ. ID. NO: 8: The N-terminal Glu 19 of BiP protein is arginylated (R-BiP); and SEQ. ID. NO: 9: arginylated BiP N-terminal peptide (R-BiPD).

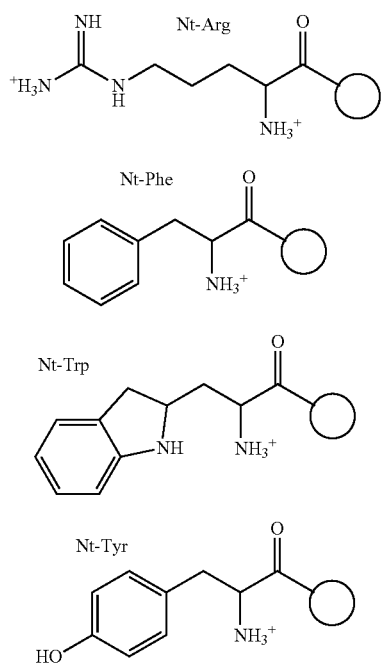

[Formula 1]

[Formula 2]

[Formula 3]

[Formula 4]

The ligand above contains the compound represented by formula 5 (p62-ZZ1; 2-(3,4-bis (benzyloxy)benzylamino) ethanol) or the compound represented by formula 6 (p62-ZZ2; 1-(3,4-bis (benzyloxy)phenoxy)-3-(isopropylamino) propanol) below. In particular, p62-ZZ2 is known as NCI314953.

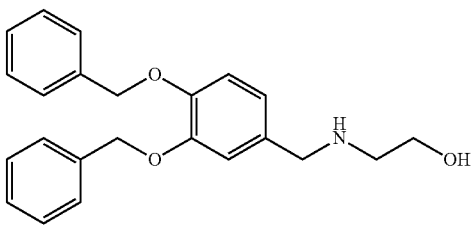

[Formula 5]

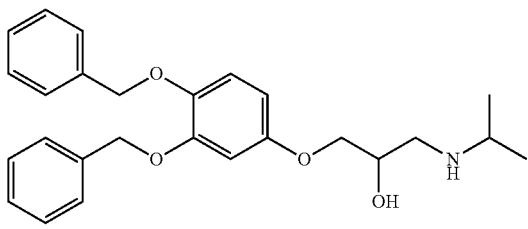

[Formula 6]

In addition, the ligand above binds to the p62 ZZ domain and activates PB1 domain and LIR domain of p62 protein, so that it induces p62 oligomerization and coagulum formation and also increases autophagosome formation by inducing p62 coagulum formation. By the processes explained above, misfolded proteins can be efficiently eliminated (see FIG. 1).

The neurodegenerative diseases herein are selected from the group consisting of Lyme borreliosis, fatal familial insomnia, Creutzfeldt-Jakob Disease (CJD), multiple sclerosis (MS), dementia, Alzheimer's disease, epilepsy, Parkinson's disease, stroke, Huntington's disease, Picks disease, and amyotrophic lateral sclerosis (ALS).

In a preferred embodiment of the present invention, the present inventors identified p62 as an N-recognin that can bind to Nt-Arg, Nt-Phe, Nt-Trp, and Nt-Tyr (see FIG. 5). In particular, p62 was confirmed to have an excellent binding force for Nt-Arg (see FIG. 6). The inventors also confirmed that the p62 ZZ domain was involved in the binding above (see FIG. 7). Arg-Ala, an N-ligand, induced p62 self-oligomerization and coagulum formation (see FIG. 8d) and also increased the binding of p62 to LC3 (see FIG. 8f). N-terminal arginylated BiP (R-BiP), calreticulin (R-CRT), and protein disulfide isomerase (R-PDI) were identified from the endoplasmic reticulum obtaining Nt-Arg through N-terminal arginylation (see FIG. 9). N-terminal arginylation of those proteins were confirmed to be mediated by ATE1 (see FIG. 10). It was also confirmed that external DNA in the cytoplasm could induce R-BiP generation (see FIG. 12), and at this time R-BiP was delivered to autophagosomes together with p62 (see FIG. 13). R-BiP was degraded by autophagic action in a P62-dependent manner and then ubiquitinized (see FIG. 16). The present inventors also identified small compounds (ZZ-L1 and ZZ-L2) structurally similar to Nt-Trp (see FIG. 18). Further, the present inventors confirmed that ZZ-L1 and ZZ-L2 increased intracellular autophagosome formation (see FIG. 19). The ZZ compounds were confirmed to fuse lysosomes and autophagosomes (see FIG. 20) and to remove misfolded proteins including huntingtin coagulum through autophagy activation (see FIGS. 21 and 22).

Therefore, the ligand binding to the p62 ZZ domain of the present invention can be effectively used as an active ingredient for a pharmaceutical composition for the prevention and treatment of neurodegenerative diseases by regulating autophagy using the same since it could induce p62 oligomerization and coagulum formation.

The therapeutic agent or pharmaceutical composition according to the present invention can be formulated into a suitable form together with a commonly used pharmaceutically acceptable carrier. The said "pharmaceutically acceptable" herein indicates a composition that is acceptable physiologically and does not cause any allergic reaction or allergy like reaction such as gastrointestinal disorder and dizziness. The pharmaceutically acceptable carrier is exemplified by water, suitable oil, saline, aqueous glucose and glycols, etc., and can additionally contain stabilizers and preservatives. Suitable stabilizers are exemplified by antioxidants such as sodium hydrogen sulfite, sodium sulfite, and ascorbic acid. Suitable preservatives are exemplified by benzalkonium chloride, methyl- or propyl-paraben, and chlorobutanol. In addition, the composition of the present invention can contain various additives such as suspending agents, solubilizers, stabilizers, isotonizing agents, preservatives, adsorption inhibitors, surfactants, diluents, excipients, pH regulators, pain relivers, buffers, antioxidants, etc. The pharmaceutically acceptable carriers and formulations suitable for the present invention, including those exemplified above, are described in detail in Remingtons's Pharmaceutical Science (the newest edition).

The composition of the present invention can be formulated by the method that can be performed by those in the art by using a pharmaceutically acceptable carrier and/or excipient in the form of unit dose or in multi-dose container. The formulation can be in the form of solution, suspension or emulsion in oil or water-soluble medium, powder, granule, tablet or capsule.

The compound represented by formula 5 or formula 6 of the present invention can be used as the form of a pharmaceutically acceptable salt, in which the salt is preferably acid addition salt formed by pharmaceutically acceptable free acids. The acid addition salt can be obtained from inorganic acids such as hydrochloric acid, nitric acid, phosphoric acid, sulfuric acid, hydrobromic acid, hydroiodic acid, nitrous acid and phosphorous acid, or non-toxic organic acids such as aliphatic mono/dicarboxylate, phenyl-substituted alkanoate, hydroxy alkanoate, alkandioate, aromatic acids and aliphatic/aromatic sulfonic acids. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate and mandelate.

The acid addition salt in this invention can be prepared by the conventional method known to those in the art. For example, the compound of formula 5 or formula 6 is dissolved in water-miscible organic solvent such as acetone, methanol, ethanol, or acetonitrile, to which excessive organic acid or acid aqueous solution of inorganic acid is added to induce precipitation or crystallization. Then, the solvent or the excessive acid is evaporated from the mixture, followed by drying the mixture to give addition salt or suction-filtering the precipitated salt to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The administration method of the pharmaceutical composition of the present invention can be easily selected according to the formulation, and can be administered to mammals such as livestock and human using various routes. For example, it can be formulated in the form of powders, tablets, pills, granules, dragees, hard or soft capsules, liquids, emulsions, suspensions, syrups, elixirs, external preparations, suppositories, and sterilized injection solutions, and can be administered systemically or locally, or orally or parenterally. At this time, parenteral administration may be particularly preferred.

Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

Solid formulations for oral administration are tablets, pills, powders, granules and capsules. These solid formulations are prepared by mixing the compound represented by formula 5 or formula 6 of the present invention with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

The effective dosage of the pharmaceutical composition of the present invention can be determined according to weight, age, gender, health condition, diet, administration frequency, administration method, excretion and severity of disease. In the case of oral administration, the pharmaceutical composition can be administered by 1 ng~10 mg per day for an adult (60 kg), and more preferably by 1 mg-1 g per day. It will be apparent to those in the art that the dosage can be additive or subtracted, as the dosage can vary depending on various conditions, and thus the dosage cannot limit the scope of the present invention by any means.

The administration frequency is once a day or a few times a day within a desired range, and the administration period is not particularly limited.

The present invention also provides a health functional food supplement for the prevention and improvement of neurodegenerative diseases comprising a ligand binding to the p62 ZZ domain as an active ingredient.

The ligand above is selected from the group consisting of Arg-Ala (SEQ. ID. NO: 2), Phe-Ala (SEQ. ID. NO: 3), Trp-Ala (SEQ. ID. NO: 4), Tyr-Ala (SEQ. ID. NO: 5), R-11 (SEQ. ID. NO: 6), W-11 (SEQ. ID. NO: 7), R-BiP (SEQ. ID. NO: 8), and R-BiPD (SEQ. ID. NO: 9). The active ingredient of the ligand above is an N-terminal residue, which is selected from the group consisting of Nt-Arg (formula 1), Nt-Phe (formula 2), Nt-Trp (formula 3), and Nt-Tyr (formula 4).

The ligand above is p62 ZZ1 (formula 5) or p62-ZZ2 (formula 6: NCI314953).

The food type that can contain the compound of the present invention is not limited and almost every food applicable in the production of health food can be included.

The compound of the present invention can be added as it is or as mixed with other food components according to conventional methods. The mixing ratio of active ingredients can be regulated according to the purpose of use (prevention or health enhancement). In general, to produce health food or beverages, the compound of the present invention is added preferably by 0.1~90 weight part. However, if long term administration is required for health and hygiene or regulating health conditions, the content can be lower than the above but higher content can be accepted as well since the compound, has been proved to be very safe.

The composition for health beverages of the present invention can additionally include various flavors or natural carbohydrates, etc, like other beverages in addition to the compound. The natural carbohydrates above can be one of monosaccharides such as glucose and fructose, disaccharides such as maltose and sucrose, polysaccharides such as dextrin and cyclodextrin, and sugar alcohols such as xylytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~10 g in 100 ml of the composition.

In addition to the ingredients mentioned above, the health food composition of the present invention can include, in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The health food composition of the present invention can also include natural fruit juice, fruit beverages and/or fruit flesh addable to vegetable beverages.

All the mentioned ingredients can be added singly or together. The mixing ratio of those ingredients does not matter in fact, but in general, each can be added by 0.1~20 weight part per 100 weight part of the compound of the invention.

Therefore, the ligand binding to the p62 ZZ domain of the present invention can be effectively used as an active ingredient for a health food supplement for the prevention and improvement of neurodegenerative diseases by regulating autophagy using the same since it could induce p62 oligomerization and coagulum formation.

In addition, the present invention provides a method containing the step of treating cells with the ligand binding to the p62 ZZ domain or p62 protein for inducing p62 oligomerization by binding the ligand to p62 ZZ domain; for increasing p62 activity comprising the step of increasing the bond between p62 and LC3; for increasing the transportation of p62 to autophagosome by binding the ligand to the p62 ZZ domain; for inducing the activation of autophagy by binding the ligand to p62 ZZ domain; for delivering the unfolded protein coagulum to autophagosome by binding the ligand to p62 ZZ domain; and for increasing the lysosome-mediated degradation of the misfolded protein coagulum by activating autophagy by using the ligand binding to the p62 ZZ domain.

Therefore, the ligand binding to the p62 ZZ domain of the present invention can be effectively used for the prevention and treatment of neurodegenerative diseases by regulating autophagy using the same since it could induce p62 oligomerization and coagulum formation.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Identification of p62 as a Novel N-Recognin

To identify novel N-recognins binding to N-degron, a peptide was synthesized by attaching an N-degron to the N-terminus. Then, the kinds of proteins that could bind to the synthesized peptide in rat tissue extracts was investigated.

Particularly, the X-peptide pull down assay and mass spectroscopy related iTRAQ (Isobaric tags for relative and absolute quantitation) were performed. As the N-end rule interaction protein, rat testis extract was used and biotin-labeled X-peptide (R11 sequence: RIFSTIEGRTY (type 1)) fixed on streptavin beads, F11 sequence (FIFSTIEGRTY (type 2), and V11 (stabilized control) (VIFSTIEGRTY) were also used (FIGS. 5a and d). The 10-mer linker connected to X-peptide was originated from Sindbis virus polymerase nsP4, the substrate of N-end rule. The mixture was diluted with 5×PBS, followed by culture at 4□ overnight. Proteins pulled down by using each X-peptide were labeled with different fluoresceins by iTRAQ. Based on Mascot score, approximately 200 proteins were identified, which included mammal UBR box E3 family, URB1, UBR2, UBR4, and UBR5 involved in N-end rule pathway (FIGS. 5b and c).

The results were confirmed by immunoblotting after X-peptide pull down assay (FIGS. 5e-i). UBR1 was observed in both R11 and F11 pull down assay. UBR2 was only confirmed in F11 pull down assay. UBR4 and UBR5 were confirmed in R11 assay. As a result of V11 (stabilized control) pull down assay, UBR protein was not precipitated. In addition to UBR E3 ligase, the protein identified by mass spectroscopy in R11 sedimentation sample was sequestosome 1 (p62) protein.

As shown in FIG. 5c, a strong band was observed in the area around 62 kDa in the R11 pull down sample in the silver stained gel, but this band was not observed in the V11 pull down sample, the negative control. According to the result of mass spectroscopy, the band was confirmed to be p62/sqstml (referred as p62 hereinafter) (FIG. 5c). From the results of the experiment above, it was confirmed that p62 was a novel N-recognin.

Example 2: Identification of p62 as an N-Recognin Capable of Binding to Nt-Arg, Nt-Phe, Nt-Trp, and Nt-Tyr The following experiment was performed in order to more clearly identify the p62 protein in Example <1-1>.

Particularly, Western blotting was performed by using the mouse monoclonal p62 antibody (1:500, ab56416, Abcam, Cambridge, UK) produced by the full-length recombinant protein corresponding to amino acids 1~440 of human p62. As a result, as shown in FIG. 5d, in vitro transcribed and translated p62 showed a strong binding affinity specifically to the R11 peptide but a weak binding affinity to the F11 peptide and no significant binding to the V11-peptide (FIG. 5d). The R11 peptide was able to precipitate p62 at the efficiency of at least 40%, based on the concentration used for the experiment herein, while the F11 peptide showed the efficiency of 5%. The results were confirmed by a dipeptide competition assay. The RA peptide (Arg-Ala) competed most effectively with R11 peptide in binding of p62. The next efficient competitor was HA (His-Ala), another type 1 N-end rule peptide (FIGS. 5h and i). Among type 2 peptides, WA (Trp-Ala) was efficient, but FA (Phe-Ala) was not efficient. From the results of the competition analysis with AR, it was confirmed that RA, HA and WA were specific to the N-end rule. The results above indicate that p62 can bind to both type 1 and type 2 N-end rule peptides.

In order to directly determine the binding specificity of p62 to N-terminal residues, the binding of p62 with the peptides having various N-terminal residues was investigated by using X-peptide pull down technique.

As result, as shown in FIG. 5h, it was confirmed that p62 could bind to three types of N-end rule N-terminal residues R11, H11, and K11 (FIG. 5h). It was also confirmed that p62 strongly bound to the R11 peptide, moderately bound to K11, and weakly bound to H11. Endogenous p62 also bound to three of the four N-end rule N-terminal residues, F11, W11 and Y11, but not L11 (FIG. 5h). Arg (R), His (H) and Lys (K) have positive side chains, while Phe (F), Trp (W) and Tyr (Y) have aromatic side chains. From the characteristics of the amino acids that bind to p62, it was confirmed that p62 could be positively charged or preferred aromatic side chains. p62 had no preference for amino acids having hydrophobic side chains such as Val (V), Leu (L) and Gly (G) and amino acids having negatively charged side chains like Asp (D). The results above indicate that p62 selectively binds to Nt-Arg, Nt-Trp, Nt-Phe, and Nt-Tyr.
A Example 3: Evaluation of the Binding Force of p62 to Nt-Arg and Nt-Phe The following experiments were performed to determine the binding constants of p62 to Nt-Arg and Nt-Phe.

Particularly, p62-D3-GST was expressed in *E. coli*, followed by purification with 50% purity. The biotin-labeled X-peptide was fixed on a streptavidin-coated chip using surface plasmon resonance biosensors (Biacore), and the p62-D3-GST protein was then inserted to the fixed peptide.

As a result, as shown in FIG. 6, p62-D3-GST strongly bound to the R11 peptide, weakly bound to F11, and did not bind to V11 (FIG. 6). Kd values of R11 and F11 were 44 nM and 3.4 μM, respectively. In particular, the binding force of p62 to Nt-Arg was about 50 times higher than that of N-recognins containing a URB box (Kd, 3.2 μM). The results indicate that p62 is a novel drug target.

Example 4: Direct Binding of Nt-Arg and Nt-Phe to the p62 ZZ Domain

To investigate the location of p62 where Nt-Arg could bind, a series of p62 deletion mutants (D1~D8) were constructed and their binding to R11 and W11 was confirmed by X-peptide pull down assay by the same manner as described in Example 1.

Particularly, D1~D4 were a series of p62 C-terminal deletion mutants. D5~D8 were a series of p62 N-terminal deletion mutants. Nt-Arg and Nt-Trp bound to D2, D3, D4, and D5 containing the ZZ domain, but did not bind to D1, D6, and D7 which did not contain the ZZ domain (FIGS. 7a-b). To investigate the binding region of p62 with Nt-Arg and Nt-Trp more precisely, a deletion mutant was generated in the p62 D3 C-terminus, whose binding with N-end rule N-terminus was examined by X-peptide pull down assay (FIG. 7c). Among the 9 p62 deletion mutants in total, CD1 CD6 were bound to Nt-Arg and Nt-Trp (FIG. 7d). The mutants from CD7 without two histidine residues, the ZZ domain zinc finger motif structure, did not bind thereto. The minimal ZZ domain of the N-terminus was determined by X-peptide pull down assay (FIG. 7e). In the region starting from the PB1 region of the full length p62 to the middle area of the ZZ domain, 6 N-terminal deletion mutants were constructed. ND-1, ND-2, ND-3, and ND-4 were bound to Nt-Arg, but ND-5 and ND-6 did not bind thereto (FIG. 7f). ND-5 did not contain the cysteine residue (C128) and aspartic acid (D129), the elements of atypical binucleate Zn-finger conserved in the UBR box. The mutant p62 without a ZZ domain could not bind to Nt-Arg (FIGS. 7g-h). The fragment containing only ZZ domain (#83-175) could bind to Nt-Arg but the D129A mutant could not bind thereto (FIGS. 7i-j). The results above indicate that Nt-Arg and Nt-Trp bind to the p62 ZZ domain.

To investigate whether or not the binding of Nt-Arg and Nt-Trp to p62 was due to the N-end rule, 6 point mutants were constructed by substituting D129, D142_145, D147_149, D151_154, H160_163 and E177 of p62 (1-440) with alanine, followed by X-peptide pull down assay. The ZZ domain mutants could not bind to Nt-Arg and Nt-Trp (FIG. 7k). The results above indicate that the ZZ domain and the UBR box bind to Nt-Arg and Nt-Trp via the N-end rule. Cys and His residues act as structural elements, and aspartic acid plays an important role in recognizing N-degrons. As described hereinbefore, the results above indicate that the binding characteristics of the p62 ZZ domain based on N-end rule N-terminus was similar to that of the UBR box, which also indicates that the ZZ domain is similar in structure to the UBR box. When X-peptides binds to p62, N-terminal residues such as Nt-Arg and Nt-Trp are active ingredients of the N-ligand.

Example 5: Structural and Functional Homology of the p62 ZZ Domain with the UBR N-Recognin UBR Box The UBR box is composed of 70 residues which is a substrate recognition domain existing in N-end rule E3 family designated as UBR1~UBR 7. The primary sequence of the p62 ZZ domain was compared with the UBR region sequence of the UBR E3 ligase originated from various organisms by using ClustalW program.

As a result, the p62 ZZ domain was confirmed to be similar in structure to the UBR box (FIG. 7l). The typical C2H2 zinc finger fold of the UBR box was well preserved in the p62 ZZ domain. In addition, an atypical binucleate Zn-finger fold of the UBR box was partially observed in the p62 ZZ domain. The UBR region contained three well preserved aspartic acids (D118, D150 and D153), which were necessary for binding to N-end rule N-terminal residues of the substrate. The p62 ZZ domain also contained three aspartic acid residues including D129, D147, and D149. Only D147 of the ZZ domain was preserved in the UBR box (D118). Those three negatively charged (acidic) aspartic acid residues were proved to be essential for binding to N-end rule N-terminal residues, as in the UBR box. The results above were consistent with the results of the previous pull down assay, which prove that p62 prefers binding to positively charged (basic) side chains. In addition to the C2H2 zinc-finger structure and three aspartic acid residues, three identical (red) residues (Y140, D147 and L150) were observed in the ZZ domain and two identical residues (G173 and W184) and one preserved (red) residue (E177) were observed outside the ZZ domain (FIG. 2b).

Example 6: p62 Self-Oligomerization and Coagulum Formation Induced by the N-ligand Arg-Ala To investigate whether or not the N-ligand Arg-Ala could induce p62 self-oligomerization and coagulum formation by binding to the p62 ZZ domain, an in vitro oligomerization assay was performed with the HEK293 cell lysate expressing full-length p62 and run on a non-reducing SDS-PAGE (FIG. 8).

HEK293 cells were transfected with a DNA plasmid expressing p62-myc/his. 24 hours later, the cells were lysed with lysis buffer (50 mM HEPES, pH 7.4, 0.15 M KCl, 0.1% Nonidet P-40, 10% glycerol, protease inhibitor, and phosphatase inhibitor) and then two cooling-thawing cycles were performed. The cell suspension was cultured in ice for 1 hour, followed by centrifugation at 4°, 13,000×g for 20 minutes. The protein concentration was determined by Bradford assay. For p62 oligomerization experiments, 1 μg of p62 protein was cultured in the presence of 100 μM bestatin at room temperature with or without a dipeptide (dissolved in water at the final of 0.5 or 1 M). The sample was mixed with non-reducing loading buffer containing 4% lithium dodecyl sulfate (LDS), which was heated at 95° for 10 minutes, followed by SDS electrophoresis. Monomers, oligomers, and coagulums of p62 were detected using a mixture of p62 and myc antibodies. Various peptides such as Arg-Ala, Lys-Ala and His-Ala (type 1); Phe-Ala, Trp-Ala and Tyr-Ala (type 2); and Ala-Arg and Ala-Phe (stabilized) were cultured in the lysate and Western blotting was performed using myc/p62 antibody.

As a result, as shown in FIG. 8a, among those peptides, only Arg-Ala containing Nt-Arg could induce specific p62 oligomerization and coagulum formation (FIGS. 8a-ca). This result indicates that the N-ligand Arg-Ala induces p62 self-oligomerization and coagulum formation.

To investigate whether the PB1 domain of p62 was involved in p62 coagulum formation, the aggregation ability of the D69A mutant was evaluated. As a result, the D69A mutant bound to Nt-Arg, but Arg-Ala did not induce the formation of p62 mutant coagulum (FIG. 8e).

Example 7: The ZZ Domain is Essential for p62 Oligomerization Induced by Arg-Ala To investigate whether or not the ZZ domain needed to bind to Arg-Ala in order to induce p62 oligomerization, a p62 oligomerization assay was performed using a p62 ZZ mutant hot able to bind to the Arg-11 peptide.

As a result, as shown in FIG. 8d, wild-type p62 effectively oligomerized/aggregated, whereas the ZZ mutant did not (FIG. 8d). This result indicates that Arg-Ala induces p62 oligomerization by binding to the ZZ domain.

Example 8: Increase Binding Between p62 and LC3 Induced by Arg-Ala

The oligomerization of p62 is initially required for the delivery of p62 to the autophagosome initiation site and subsequently introduced into the membrane of autologous endoplasmic reticulum via the interaction of LC3 and p62 oligomers (Itakura et al., 2011). To confirm the effect of Arg-Ala on the binding of p62 to LC3, an ELISA was performed (FIGS. 8f-h).

p62 KO mouse embryonic fibroblasts were transfected with the full-length p62 and p62 mutants. 24 hours later, the cells were lysed with lysis buffer, followed by centrifugation at 4☐ at 13,000 rpm. The cell lysate (20 μg) was cultured with the GST tagged LC3 recombinant protein (Enzo lifescience, BML-UW1155) fixed on the plate coated with GSH wherein type 1 and type 2 dipeptides were cultured at room temperature for 1.5 hours. The conjugated p62 was cultured with anti-p62 antibody (SC-28359, Santa Cruz) for 1 hour at room temperature. HRP binding secondary antibody was cultured for 45 minutes, followed by detection. The plate was washed with PBS three times. TMB (3,3',5,5'-Tetramethylbenzidine) substrate (Priece, 34021) was added to each well of the plate, which stood at room temperature for 10 minutes in the dark room to induce color change. The TMB stop solution 2N $H_2SO_4$ was added thereto, and then $OD_{450}$ was measured.

As a result, as shown in FIG. 8f, among the various peptides, Arg-Ala was the only one that enhanced the binding of p62 and LC3 (FIG. 8f). p62 ZZ mutants, for example 129A, C142/145A, D147/149A, C151/154A, H160/163A and ZZ del, and PB1 mutants, for example D56A, did not bind to LC3 (FIGS. 8g and h). Therefore, it was confirmed from the results above that Arg-Ala bound to the p62 ZZ domain to induce a conformational change, activating the p62 coagulum via the PB1 domain, and induced p62-LC3 mutual binding via the LIR domain. FIG. 8i is a diagram illustrating the inactivated form and activated form of p62.

Example 9: Identification of Endoplasmic Reticulum Proteins Which Obtain Nt-Arg Through N-Terminal Arginylation Since Nt-Arg, the physiological N-ligand of the p62 ZZ domain, could be produced through N-terminal arginylation by ATE1 R-transferase, N-terminal sequences of endoplasmic reticulum proteins were investigated using bioinformatics.

As a result, Nt-Arg and Nt-Glu were confirmed to act as substrates for arginylation by ATE1 R-transferase based on the N-terminal degradation pathway (N-end rule pathway); and accordingly, the possibility of Nt-Arg to function as a N-ligand was confirmed (FIG. 10a). By using bioinformatics technique, it was confirmed that many endoplasmic reticulum chaperones such as BiP, calreticulin (CRT), protein disulfide isomerase (PDI), GRP94 and ERdJ5 contained Nt-Asp or Nt-Glu, and the amino acid L-Arg could be obtained by ATE1 R-transferase to mediate arginylation (FIG. 9).

Example 10: Construction of N-Terminal Arginylated BiP, CRT and PDI Subpopulation Specific Antibodies To construct antibodies which specifically recognizing N-terminal arginylated BiP (R-BiP), calreticulin (R-CRT), and protein disulfide isomerase (R-PDI), peptides corresponding to the N-terminus of these N-terminal arginylated proteins such as REEEDKKEDVG (R-BiP), REPAVYFKEQ (R-CRT), and RDAPEEEDHVL (R-PDI) were synthesized. These peptides were inoculated in a rabbit to obtain antibody serum. Antibodies were purified by IgG chromatography. The antibody group was passed through chromatography using non-arginylated peptides such as EEEDKKEDVGC, EPAVYFKEQ, and DAPEEEDHVL as ligands in order to eliminate non-specific antibodies. Finally, the arginylation-specific antibodies were purified by passing them through chromatography using the arginylated peptides such as REEEDKKEDVGC (R-BiP), REPAVYFKEQ (R-CRT), and RDAPEEEDHVL (R-PDI) as ligands (FIG. 10b).

Example 11: ATE1 Mediated N-Terminal Arginylation of BiP, CRT, and PDI

ATE1 R-transferase isomerase was over-expressed and then R-BiP formation was investigated by using the R-BiP antibody, (FIG. 10d). When ATE1 was knocked-down by using siRNA, R-BiP formation was reduced (FIG. 10e).

Further, Ub-X-B P flag (X=Glu or Val) was over-expressed to examine arginylation (FIG. 11a). The Ub-X-BiP-flag is converted into Ub and X-BiP-flag by a deubiquitinating enzyme simultaneously with translation. Using the recombinant protein, it was revealed that the Nt-Glu19 of X-BiP was the residue that was arginylated (FIG. 11a).

Another recombinant protein, Ub-X-BiP-myc/his construct, was generated (FIG. 11b). Herein, X contained Arg18, Glu19, or Val19. Since the construct did not contain an ER signal, it stayed in the cytoplasm. Once ubiquitin is eliminated by ubiquitin hydrolases, the N-terminal region was exposed. Using this construct, X-BiP was arginylated at Nt-Glu19 (FIG. 11c). R-BiP was not generated in ATE1 knock-out cells (FIG. 11d). It was confirmed by an experiment using thapsigargin, which causes ER stress, that R-BiP was generated not by ER stress but as the product of an enzyme reaction induced by ATE1 R-transferase (FIG. 11e). The produced R-BiP migrated into the cytoplasm in a large amount, as examined by cell fractionation (FIG. 11f). The migrated R-BiP in the cytoplasm was relatively less degraded, compared with the non-arginylated BiP in endoplasmic reticulum, as examined by the cycloheximide protein degradation technique (FIG. 11g). This was consistent with the experimental results that R-BiP was transferred to autophagy. These results indicate that the N-terminal Nt-G19 of BiP is arginylated by ATE1 when it migrates into cytoplasm.

It was investigated whether or not CRT and PDI also underwent arginylation by ATE1. As a result, it was confirmed that R-CRT and R-PDI were produced when ATE1 isoenzyme was overexpressed (FIG. 11h). These results indicate that many endoplasmic reticulum chaperones and other proteins in addition to BiP, CRT, and PDI, can be modified by N-terminal arginylation mediated by ATE1.

Example 12: R-BiP Production Induced by External DNA in the Cytoplasm

To investigate the cause of R-BiP production, stresses that could cause N-terminal arginylation of endoplasmic reticulum proteins were investigated in various ways.

As result, as shown in FIG. 12, R-BiP generation was specifically induced when double stranded DNA (dsDNA) was introduced into the cytoplasm (FIGS. 12a and b). In addition to R-BiP, R-CRT production was also specifically induced when dsDNA was introduced into the cytoplasm (FIGS. 12b and c). It was observed that the transfer of BiP into the cytoplasm and it subsequent arginalyation into R-BiP was induced by dsDNA in the cytoplasm by using a cell fractionation technique (FIG. 12d). It was also confirmed that R-BiP, R-CRT, and P-PDI were generated as part of the innate immune response to invading DNA using poly (dA:dT) mimicking a pathogen (virus or bacteria) containing DNA (FIGS. 12e-g). Invading DNA also led to autophagy activation (FIGS. 12b and f).

Example 13: Transportation of R-BiP tTogether with p62 to Autophagosomes

Immunostaining was performed to observe the simultaneous transportation of R-BiP and p62 to autophagosome.

As a result, as shown in FIG. 13, it was confirmed that R-BiP in the cytoplasm collected in puncta like cell structures (FIG. 13a). The R-BiP puncta was colocalized with p62 puncta (FIGS. 13a and c) and also colocalized with LC3 (FIGS. 13b-d). It was also confirmed that BiP was transferred to LC3-positive autophagosomes in the mouse embryo heart (FIG. 13e). When ATE1 or BiP was knocked-down by using siRNA, R-BiP was not able to move to autophagosomes (FIGS. 13f-h). When p62 was knocked-out, similar results were observed (FIGS. 13f-h). These results indicate that R-BiP in the cytoplasm is transferred to autophagosome via p62 and finally degraded by lysosomes.

Example 14: Nt-Arg is Required for R-BiP Delivery to Autophagosome

X-BiP-GFP was produced by over-expressing Ub-X-BiP-GFP recombinant protein (X=Arg, Glu, or Val) in cells (FIG. 14a), followed by immunostaining to investigate the migration thereof. R-BIP was transferred to autophagosomes (FIG. 14c). Where as, Val-BiP (Nt-G19 was replaced with Val so that it could not be used as a substrate for arginylation) was not transferred to autophagosome because of the lack of Nt-Arg (FIG. 14c). Comparing with LC3 puncta, the intracellular location of R-BiP was consistent with that of LC3 (FIG. 14d). Because another region of the BiP protein could affect autophagy targeting, Ub-X-BiP$^\Delta$ (FIG. 14a) wherein most regions of BiP protein were eliminated and only the residue sequence ranging from 19 to 124 was left was over-expressed. Then, immunostaining was performed to investigate the intracellular location of X-BiP$^\square$ (FIG. 14e). As a result, it was confirmed that. R-BiP$^\square$ formed puncta in p62+/+ cells and moved to autophagosomes (FIG. 14e). E-BiP$^\square$ which could be arginylated in p62+/+ cells, so that it moved to autophagosomes normally but did not move to autophagosomes in p62−/− cells (FIG. 14e). V-BiP$^\square$ did not move to autophagosomes in neither p62+/+ nor p62−/− cells (FIG. 14e). The intracellular location of X-BiP and LC3 was investigated by immunostaining. The results were consistent with the above (FIG. 14f). These results therefore confirmed that when BiP or other endoplasmic reticulum proteins are transferred to the cytoplasm, they are arginylated (after binding to misfolded proteins or other substrates), the Nt-Arg generated by post-translational modification worked as a N-ligand to bind the p62 ZZ domain.

Example 15: Direct Binding of R-BiP Nt-Arg to the p62 ZZ Domain

An X-peptide pull down assay was performed to investigate whether or not R-BiP Nt-Arg could bind to the p62 ZZ domain (FIGS. 15a and b).

As a result, as shown in FIG. 15, R-BiP peptide pulled down p62 in cell extracts, however E-BiP or V-BiP peptide did not (FIGS. 15c and d). To investigate where Nt-Arg binds to p62, p62 deletion mutants were made (FIG. 15e). A pull down assay was performed with these p62 mutants and R-BiP peptide. As a result, R-BiP Nt-Arg could bind only to the p62 ZZ domain (FIG. 15f).

To confirm the binding between R-BiP and the p62 ZZ domain, the p62 ZZ domain only mutants named p62-ZZ83-175-GST and p62-ZZ (D129A)83-175, followed by GST pull down assay (FIG. 15g). ZZ83-175 could pull down Arg18-Bip19-654 but did not pull down Val19-Bip19-654. The ZZ mutant ZZ (D129A)83-175 could not pull down either Arg-BiP18-654 or Val-BiP19-654. Therefore, it was confirmed that a functional p62 ZZ domain was required for the N-end rule-dependent interaction of arginylated Bip and p62 (FIG. 15h).

When p62-ZZ83-175-RFP and ubiquitin-X-Bip19-124-GFP were coexpressed in MEF cells, Arg18-Bip19-124 was colocalized with p62-ZZ83-175-RFP showing puncta formation, while Val19-Bip19-124-GFP was not colocalized with p62-ZZ83-175-RFP and had no puncta formation (FIG. 15i).

Example 16: P62 Dependent Degradation of R-BiP by Autophagy

To confirm whether or not R-BiP was decomposed by autophagy through p62, Ub-X-BiP$^\Delta$-GST was constructed and then over-expressed in p62+/+ and p62-/- cells (FIG. 16a).

As a result, as shown in FIG. 16, R-BiP was degraded easily in p62+/+ cells, compared with V-BiP, while it was not degraded and instead accumulated in p62 -/- cells (FIGS. 16a and b). In the meantime, V-BiP was not degraded but accumulated in both p62+/+ and p62-/- cells (FIGS. 16a and b). R-BiP was not degraded but accumulated when hydroxychloroquine (autophagy inhibitor) was used (FIGS. 16a and b). R-BiP was not degraded but accumulated in autophagy deficient ATG5-/- cells (FIG. 16c). A cycloheximide proteolysis quantification assay was performed with Ub-R-BiP-myc/his. As a result, it was confirmed that R-BiP was remarkably stable in ATG5-/- cells (FIGS. 16d and e). The results above indicate that R-BiP was, delivered to lysosome by p62 and then degraded therein.

Example 17: Inducement of R-BiP by Ubiquitinized Protein in Cytoplasm

To investigate the type of stresses that induce R-BiP, cells were treated with various chemicals, followed by immunoblotting to examine the formation of R-BiP.

As a result, the formation of R-BiP was commonly induced by proteasome inhibitors (FIG. 17c). When the formation, of R-BiP was induced, it was accumulated together with ubiquitin conjugated intracellular proteins (FIG. 17c). This phenomenon was also observed when the cells were treated with poly (dA:dT) (FIG. 17c). Some of those ubiquitinized intracellular proteins formed puncta and were delivered to p62 bodies (a construct in which p62-derived proteins are temporarily existed as a form of coagulum before they are transferred to autophagosome). Herein, R-BiP and p62 were colocalized (FIG. 17b). These results above indicate that the misfolded proteins accumulated in cytoplasm were ubiquitinated and delivered to autophagosomes. In addition, proteasome inhibitors and poly (dA:dT) induced endoplasmic reticulum chaperones to migrate to the cytoplasm where N-terminal arginylation of these chaperones occur. R-BiP in the cytoplasm was transferred to p62 bodies together with the ubiquitinized proteins.

Example 18: R-BiP Binds to Misfolded Proteins in Cytoplasm to Deliver them to Autophagy Cells were treated with geldenamycin (Hsp90 inhibitor) to promote the formation of intracellular misfolded proteins.

As a result, it was confirmed that R-BiP formation was induced (FIG. 17f). When YFP-CL1, the model substrate which was self-folding and denatured, was over-expressed, it directly bound to R-BiP (FIG. 17g). Immunofluorescence staining was performed to confirm that YFP-LC1 was delivered to autophagic vacuoles, wherein R-BiP and p62 were colocalized (FIGS. 17h and i). These results indicate that R-BiP was bound to the misfolded proteins accumulated in cytoplasm and transferred to autophagosomes together with p62.

As shown in FIG. 1, when misfolded proteins and the coagulum thereof were accumulated in cytoplasm, they sent a signal to endoplasmic reticulum and then various chaperones such as BiP, CRT, and PDI migrate to the cytoplasm where they experience N-terminal arginylation by ATE1 to produce an Nt-Arg ligand. These chaperones bind to the p62 ZZ domain through their Nt-Arg ligand while also binding to misfolded proteins. Upon the binding of Nt-Arg ligand to the ZZ domain, p62 changes from a closed structure to an open structure. Accordingly, the PB1 domain of p62 (mediates oligomerization) was exposed, and p62 self-oligomerized to form the p62 body along with R-BiP, the misfolded protein. The LC3 binding domain of p62 was also exposed to accelerate the binding with LC3 extruded on autophagosome membranes. As a result, the misfolded protein-R-BiP-p62 was delivered to autophagosome in the form of a coagulum complex and thereafter it was degraded by lysosomal proteolysis.

Experimental Example 1: Increase of p62 Oligomerization and LC3 Binding by the Low Molecular Weight Compound p62-ZZ1

As an effort to identify more p62 ZZ domain ligands, in addition to Arg-Ala, studies had been made and confirmed that the small compounds 2-((3,4-bis (benzyloxy)benzyl) amino)ethan-1-ol hydrochloride (named ZZ-L1; formula 5) and 1-(3,4-bis (benzyloxy)phenoxy)-3-(isopropylamino)-2-propanol (named ZZ-L2; formula 6) having the structural similarity to Nt-Trp, an N-end rule ligand, promoted p62 activity, in particular oligomerization and autophagy activity. ZZ-L2 is the material known as NCI314953. These low molecular weight compounds have structural similarity to Phe-Ala or Trp-Ala rather than Arg-Ala and therefore bind to the type-2 binding subdomain of the ZZ domain.

It was investigated whether or not the p62 oligomerization and activity could be increased when these low molecular compounds bind to p62 ZZ domain like Arg-Ala.

An in vitro oligomerization assay was performed to measure the dose-dependent p62 aggregation (0, 10, 100, and 1,000 μM).

As a result, as shown in FIG. 18, like Arg-Ala, ZZ-L1 induced p62 aggregation dose-dependently (FIGS. 18a and b). It was also investigated whether or not ZZ-L1 could activate p62 by the same manner as used for the experiment to investigate p62/LC3 binding using Arg-Ala. As a result, ZZ-L1 could increase the binding of p62 with LC3 dose-dependently (0, 10, 25, 100, 500, and 1000 μM) (FIG. 18c). Therefore, it was confirmed that ZZ-L1 could induce the structural activation of p62 with the similar pattern to that of Arg-Ala by binding to the p62 ZZ domain.

Also, in order to investigate ZZ-L1 and ZZ-L2 mediated p62 puncta formation, immunofluorescence confocal microscopy was performed (FIGS. 18d-g). Particularly, HeLa cells layered on a cover slip were treated with XIE ZZ compound at different concentrations (0, 1, 2.5, 5, and 10 μM) for 12 hours (FIGS. 18f and g) or with 10 μM XIE ZZ compound for different treatment times (0, 1, 3, 6, and 12 h) (FIG. 18e). As a result, ZZ-L1 and ZZ-L2 could induce p62 puncta formation for 12 hours dose-dependently (0, 1, 5, and 10 μM) or at the concentration of 10 μM time-dependently (1, 3, 6, and 12 h) (FIGS. 18d-g).

Experimental Example 2: Increase of Intracellular Autophagosome Formation by ZZ-L1 and ZZ-L2

Western blotting was performed to investigate the effect of ZZ-L1 and ZZ-L2 on autophagy.

As a result, ZZ-L1 and ZZ-L2 increased LC3 dose-dependently (0, 1, 5, and 10 μM) and time-dependently (1, 3, 6, and 12 h), and also increased the conversion of LC3-1 (inactive form) into LC3-II (active form) (FIG. 19b). It was also confirmed that the ZZ ligands promoted not only the formation of p62 autophagy puncta but also the formation of LC3 autophagy puncta in HeLa cells by using immunofluorescence staining (FIG. 19a). These results indicate that these ZZ ligands function as autophagy activators.

It was also investigated whether or not the increase of LC3 protein and the formation of LC3-II induced by these compounds were attributed to p62. HeLa cells on a 6-well plate ($1 \times 10^6$/well) were treated with 40 nM p62 siRNA by using RNAi Max reagent (Invitrogen) in order to induce p62 knock-down. At this time, siRNA control group was also treated thereto. DMSO or 5 mM ZZ compound was cultured for 3 or 6 hours.

As a result, it was confirmed that the increase of LC3 and the formation of LC3-II were induced by the ZZ compounds ZZ-L1 and ZZ-L2. However, this effect was completely suppressed by p62 knock-down (FIG. 19c). In another experiment using p62+/+ and p62−/− cells, ZZ-L1 (5 mM) could not function as an autophagy activator in p62−/− cells (FIG. 19d). The results above indicate that the ZZ compound, like Arg-Ala, binds to the p62 ZZ domain so that p62 aggregation mediated by the p62 PB1 domain and further autophagosome formation was increased.

Experimental Example 3: Increase of Autophagy Flux by the ZZ Ligand

The increase of LC3 synthesis and the formation of LC3-II induced by the treatment of ZZ ligand could result from either the activation of autophagy flux upstream of autophagsome formation (synthesis and translation of key factors) or downstream (fusion of autophagosome and lysosome or degradation process in lysosome). To investigate whether or not the autophagy flux was normal in cells treated with the ZZ ligand, the cells were also treated with an autophagy inhibitor. Then, immunoblotting was performed to measure the level of LC3. An autophagy flux assay was performed by using $NH_4Cl$ (Sigma, A9434), bafilomycin A1 (Sigma, B1793), and hydroxychloroquine (HCQ) (Sigma, H0915) acting as inhibitors of lysosomal degradation (FIG. 19e). The cells were treated with XIE ZZ compound for 3 hours, to which an autophagosome inhibitor was treated, followed by culture for 3 more hours. Western blotting was performed with the cell lysate. The strength of the LC3-II band was measured using imageJ. The increase of LC3-II formation was normalized to GAPDH and then calculated.

As a result, the inhibition of autophagy by hydroxychloroquine (HCQ) even after the treatment of XIE ZZ compound increased the autophagy dynamics including the accumulation of LC3-II at least twice as high (FIG. 19e). The results above indicate that ZZ ligand increased the synthesis of key factors of autophagy like LC3 and accordingly increased the formation of autophagosome, and the generated autophagosomes normally bound to lysosomes and thereby degraded substrates delivered therein (p62, R-BiP, unfolded proteins, etc.) (FIG. 19g).

Experimental Example 4: Fusion of Autophagosome Induced by the ZZ Ligands with Lysosome To investigate whether or not the autophagosome induced by the ZZ ligands was delivered to lysosome, autophagy dynamic assay was performed in the same manner as used for the experiment using the HeLa cells transfected stably with RFP-GFP-LC3 wherein acid sensitive GFP and insensitive RFP were combined therein.

As a result, it was confirmed that ZZ-L1 and ZZ-L2 accelerated the formation of RFP+GFP+ autophagosome (neutral pH), and at the same time, it was also confirmed that GFP+ signal disappeared from some of RFP+ puncta (FIG. 19f). That was because acid-sensitive GFP fluorescence disappeared in the acid environment when RFP+GFP+ autophagosome was fused with lysosome to form autolysosome (acidic pH). The results above indicate that the autophagosome formed by ZZ ligands was successfully delivered to lysosome and degraded therein (FIG. 19g).

The concentration of intracellular p62 was directly measured, which is another method to investigate the autophagy flux induced by ZZ ligands. HeLa cells were treated with ZZ-L1, followed by cycloheximide proteolysis assay. As a result, it was confirmed that p62 degradation was induced by ZZ-L1 (FIG. 20a). These results indicate that the p62 in combination with ZZ ligands acts as an autophagy activator.

Experimental Example 5: Autophagy Activation by p62 in Combination with ZZ Ligand Independent of mTOR The most representative autophagy activator known so far is rapamycin. Rapamycin is a mTOR (mammalian Target Of Rapamycin) inhibitor [ref]. When mTOR is inhibited by rapamycin, the autophagy related key factors such as ULK and Beclin are activated, by which the synthesis of LC3 and the conversion of LC3-II are induced, resulting in the increase of autophagosome production (FIG. 20d). Due to the effect of rapamycin as an autophagy activator, its value as a treating agent is high. However, it is still limited in use as a treating agent because of side-effects such as broad biological effects through mTOR.

Therefore, it is urgently required to develop a novel autophagy activator that does not go through mTOR.

To compare the effect and mechanism of ZZ ligands and rapamycin as autophagy activators, HeLa cells were treated with them at different concentrations and for different times. Then, LC3 generation and LC3-II conversion were investigated.

As a result, it was confirmed that ZZ ligands had a similar or better efficacy than rapamycin (FIGS. 20b and c).

To investigate whether or not ZZ ligands could activate autophagy through mTOR, HeLa cells were treated with ZZ ligands or rapamycin, followed by the investigation of p70S6K phosphorylation regulated by mTOR (FIG. 20d). As expected, the p70S6K phosphorylation was inhibited by rapamycin by suppressing mTOR, but ZZ ligands did not inhibit the phosphorylation of 70S6K (FIG. 20e). The results indicate that ZZ ligands could activate autophagy without passing through mTOR unlike the conventional rapamycin. Therefore, ZZ ligands were confirmed to be novel autophagy activators.

Experimental Example 6: Transportation of the Proteins Targeted by Intracellular Ubiquitin to Autophagy by ZZ Ligands Intracellular misfolded proteins are primarily targeted for ubiquitination and then degraded by the proteasome. Under conditions where misfolded proteins coagulate (ex: mutant huntingtin protein), the proteasome activity is reduced, or the misfolded protein cannot enter the proteasome, so the misfolded proteins are collected by autophagy and then degraded by lysosomes. Based on the results that ZZ ligands increase autophagy flux, it was investigated by immunofluorescence staining whether or not ZZ ligands could increase the transportation of ubiquitinated intracellular proteins to autophagy.

As a result, it was confirmed that 5 mM ZZ-L1 induced the movement of the ubiquitinated proteins to autophagic vacuoles (FIG. 20f). When hydroxychloroquine, an autophagy inhibitor, was treated thereto, the ubiquitinated proteins accumulated in autophagic vacuoles (FIG. 20f). These results indicate that ZZ ligands promote the accumulation of the intracellular misfolded proteins in autophagy.

Experimental Example 7: Elimination of Mutant Huntingtin Protein Coagulum by ZZ Ligands Huntingtin protein observed in Huntington's disease is not only easily misfolded due to the excessive repeats of CAG codon (at least 36 repeats) but also converted quickly into coagulum (aggregates), suggesting that the protein is not decomposed by the ubiquitin-proteasome system (FIG. 21a). Even though a technique to eliminate such mutant protein by inducing autophagy activation using rapamycin was developed, rapamycin is not suitable as a treatment agent because rapamycin affects various biological pathways through mTOR. Considering that ZZ ligands activate autophagy without passing through mTOR, it was investigated whether or not ZZ ligands could eliminate huntingtin protein coagulum.

Wild-type huntingtin (HDQ25-GFP) and the mutant huntingtin (HDQ103-GFP; CAG repeats 103 times) were expressed in HeLa cells, followed by observation with immunofluorescence staining. As a result, HDQ25-GFP was distributed all over the cells, while HDQ103-GFP was gathered as protein coagulum (FIG. 21c). The cells over-expressing the huntingtin proteins were treated with 10 mM ZZ-L1 or 1 mM rapamycin, followed by dot blot assay to investigate the intracellular huntingtin protein. As a result, ZZ-1 eliminated the mutant huntingtin protein coagulum more efficiently (FIG. 21b). A similar experiment was set, wherein cells were divided into a soluble fraction that could be dissolved in 0.5% Triton X-100 and an insoluble fraction (including coagulum), followed by immune blotting. As a result, the huntingtin protein was more efficiently eliminated from the coagulum fraction treated with ZZ-L1 (FIG. 21d). When rapamycin was treated thereto, the similar result was obtained (FIG. 21d). HeLa cells were treated with ZZ-L1, ZZ-L2, and rapamycin and the results were compared with the results above (FIG. 21e). As a result, the results were consistent with the above.

To investigate whether or not the elimination of the huntingtin coagulum was attributed to the autophagy activation induced by ZZ ligands, ATG5+/+ and ATG5-/- cells (autophagosome was not formed in the absence of ATG5) were treated with 10 mM ZZ ligand and mM rapamycin, followed by immunoblotting. In ATG5+/+ cells, the huntingtin coagulum was efficiently eliminated by the ZZ ligand, while in ATG5-/- cells, such effect was not observed (FIG. 21f). The results above indicate that ZZ ligands can eliminate the huntingtin protein coagulum by inducing autophagic activation.

To investigate the mechanism of ZZ ligands to eliminate the huntingtin coagulum, HeLa cells over-expressing HDQ103-GFP protein coagulum were treated with 10 mM ZZ ligand, followed by immunofluorescence staining. In the cells not-treated with ZZ-L1, HDQ103-GFP formed an inclusion body. In this structure, p62 was colocalized with R-BiP (FIGS. 22a and b). In the cells treated with ZZ-L1, the huntingtin inclusion body was either reduced or removed efficiently (FIGS. 22a-c). From the above results, it was confirmed that the ZZ ligand activated autophagy to efficiently eliminate the misfolded protein coagulum.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method of decreasing huntingtin protein coagulum comprising contacting a cell with the compound represented by the formula 6

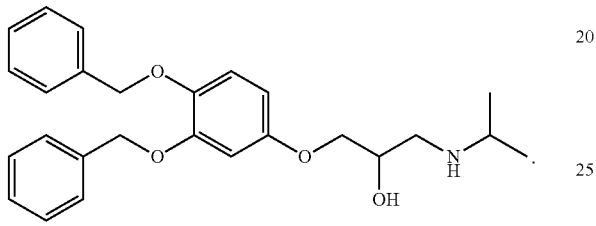

2. The method of claim 1 wherein huntingtin protein coagulum is decreased by autophagy activation.

* * * * *

SEQUENCE LISTING

<160> NUMBER OF SEQ ID NOS: 9

<210> SEQ ID NO 1
<211> LENGTH: 440
<212> TYPE: PRT
<213> ORGANISM: Homo sapiens

<400> SEQUENCE: 1

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Ala Gly Pro Gly Pro Cys Glu Arg Leu Leu
        35                  40                  45

Ser Arg Val Ala Ala Leu Phe Pro Ala Leu Arg Pro Gly Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg

```
                      85                  90                  95
Ile Tyr Ile Lys Glu Lys Glu Cys Arg Arg Asp His Arg Pro Pro
            100                 105                 110
Cys Ala Gln Glu Ala Pro Arg Asn Met Val His Pro Asn Val Ile Cys
            115                 120                 125
Asp Gly Cys Asn Gly Pro Val Val Gly Thr Arg Tyr Lys Cys Ser Val
130                 135                 140
Cys Pro Asp Tyr Asp Leu Cys Ser Val Cys Glu Gly Lys Gly Leu His
145                 150                 155                 160
Arg Gly His Thr Lys Leu Ala Phe Pro Ser Pro Phe Gly His Leu Ser
                165                 170                 175
Glu Gly Phe Ser His Ser Arg Trp Leu Arg Lys Val Lys His Gly His
                180                 185                 190
Phe Gly Trp Pro Gly Trp Glu Met Gly Pro Pro Gly Asn Trp Ser Pro
                195                 200                 205
Arg Pro Pro Arg Ala Gly Glu Ala Arg Pro Gly Pro Thr Ala Glu Ser
210                 215                 220
Ala Ser Gly Pro Ser Glu Asp Pro Ser Val Asn Phe Leu Lys Asn Val
225                 230                 235                 240
Gly Glu Ser Val Ala Ala Leu Ser Pro Leu Gly Ile Glu Val Asp
                245                 250                 255
Ile Asp Val Glu His Gly Gly Lys Arg Ser Arg Leu Thr Pro Val Ser
                260                 265                 270
Pro Glu Ser Ser Ser Thr Glu Glu Lys Ser Ser Ser Gln Pro Ser Ser
                275                 280                 285
Cys Cys Ser Asp Pro Ser Lys Pro Gly Gly Asn Val Glu Gly Ala Thr
            290                 295                 300
Gln Ser Leu Ala Glu Gln Met Arg Lys Ile Ala Leu Ser Glu Gly
305                 310                 315                 320
Arg Pro Glu Glu Gln Met Glu Ser Asp Asn Cys Ser Gly Gly Asp Asp
                325                 330                 335
Asp Trp Thr His Leu Ser Ser Lys Glu Val Asp Pro Ser Thr Gly Glu
                340                 345                 350
Leu Gln Ser Leu Gln Met Pro Glu Ser Glu Gly Pro Ser Ser Leu Asp
            355                 360                 365
Pro Ser Gln Glu Gly Pro Thr Gly Leu Lys Glu Ala Ala Leu Tyr Pro
            370                 375                 380
His Leu Pro Pro Glu Ala Asp Pro Arg Leu Ile Glu Ser Leu Ser Gln
385                 390                 395                 400
Met Leu Ser Met Gly Phe Ser Asp Glu Gly Gly Trp Leu Thr Arg Leu
                405                 410                 415
Leu Gln Thr Lys Asn Tyr Asp Ile Gly Ala Ala Leu Asp Thr Ile Gln
                420                 425                 430
Tyr Ser Lys His Pro Pro Leu
            435                 440

<210> SEQ ID NO 2
<211> LENGTH: 2
<212> TYPE: PRT
<213> ORGANISM: Artificial
<220> FEATURE:
<223> OTHER INFORMATION: Arg Ala peptide

<400> SEQUENCE: 2

Arg Ala
```

```
<210> SEQ ID NO 3
<211> LENGTH: 2
<212> TYPE: PRT
<213> ORGANISM: Artificial
<220> FEATURE:
<223> OTHER INFORMATION: Phe Ala peptide

<400> SEQUENCE: 3

Phe Ala
1

<210> SEQ ID NO 4
<211> LENGTH: 2
<212> TYPE: PRT
<213> ORGANISM: Artificial
<220> FEATURE:
<223> OTHER INFORMATION: Trp Ala peptide

<400> SEQUENCE: 4

Trp Ala
1

<210> SEQ ID NO 5
<211> LENGTH: 2
<212> TYPE: PRT
<213> ORGANISM: Artificial
<220> FEATURE:
<223> OTHER INFORMATION: Tyr Ala peptide

<400> SEQUENCE: 5

Tyr Ala
1

<210> SEQ ID NO 6
<211> LENGTH: 12
<212> TYPE: PRT
<213> ORGANISM: Artificial
<220> FEATURE:
<223> OTHER INFORMATION: R-11 peptide

<400> SEQUENCE: 6

Arg Ile Phe Ser Thr Ile Glu Gly Arg Thr Tyr Lys
1               5                   10

<210> SEQ ID NO 7
<211> LENGTH: 12
<212> TYPE: PRT
<213> ORGANISM: Artificial
<220> FEATURE:
<223> OTHER INFORMATION: W-11 peptide

<400> SEQUENCE: 7

Trp Ile Phe Ser Thr Ile Glu Gly Arg Thr Tyr Lys
1               5                   10

<210> SEQ ID NO 8
<211> LENGTH: 636
<212> TYPE: PRT
<213> ORGANISM: Artificial
<220> FEATURE:
<223> OTHER INFORMATION: R-Bip peptide

<400> SEQUENCE: 8

Glu Glu Glu Asp Lys Lys Glu Asp Val Gly Thr Val Val Gly Ile Asp
1               5                   10                  15
```

```
Leu Gly Thr Thr Tyr Ser Cys Val Gly Val Phe Lys Asn Gly Arg Val
            20                  25                  30
Glu Ile Ile Ala Asn Asp Gln Gly Asn Arg Ile Thr Pro Ser Tyr Val
                35                  40                  45
Ala Phe Thr Pro Glu Gly Glu Arg Leu Ile Gly Asp Ala Ala Lys Asn
    50                  55                  60
Gln Leu Thr Ser Asn Pro Glu Asn Thr Val Phe Asp Ala Lys Arg Leu
65                  70                  75                  80
Ile Gly Arg Thr Trp Asn Asp Pro Ser Val Gln Gln Asp Ile Lys Phe
                85                  90                  95
Leu Pro Phe Lys Val Val Glu Lys Lys Thr Lys Pro Tyr Ile Gln Val
            100                 105                 110
Asp Ile Gly Gly Gly Gln Thr Lys Thr Phe Ala Pro Glu Glu Ile Ser
            115                 120                 125
Ala Met Val Leu Thr Lys Met Lys Glu Thr Ala Glu Ala Tyr Leu Gly
    130                 135                 140
Lys Lys Val Thr His Ala Val Val Thr Val Pro Ala Tyr Phe Asn Asp
145                 150                 155                 160
Ala Gln Arg Gln Ala Thr Lys Asp Ala Gly Thr Ile Ala Gly Leu Asn
                165                 170                 175
Val Met Arg Ile Ile Asn Glu Pro Thr Ala Ala Ala Ile Ala Tyr Gly
            180                 185                 190
Leu Asp Lys Arg Glu Gly Glu Lys Asn Ile Leu Val Phe Asp Leu Gly
            195                 200                 205
Gly Gly Thr Phe Asp Val Ser Leu Leu Thr Ile Asp Asn Gly Val Phe
            210                 215                 220
Glu Val Val Ala Thr Asn Gly Asp Thr His Leu Gly Gly Glu Asp Phe
225                 230                 235                 240
Asp Gln Arg Val Met Glu His Phe Ile Lys Leu Tyr Lys Lys Lys Thr
                245                 250                 255
Gly Lys Asp Val Arg Lys Asp Asn Arg Ala Val Gln Lys Leu Arg Arg
            260                 265                 270
Glu Val Glu Lys Ala Lys Arg Ala Leu Ser Ser Gln His Gln Ala Arg
            275                 280                 285
Ile Glu Ile Glu Ser Phe Tyr Glu Gly Glu Asp Phe Ser Glu Thr Leu
    290                 295                 300
Thr Arg Ala Lys Phe Glu Glu Leu Asn Met Asp Leu Phe Arg Ser Thr
305                 310                 315                 320
Met Lys Pro Val Gln Lys Val Leu Glu Asp Ser Asp Leu Lys Lys Ser
                325                 330                 335
Asp Ile Asp Glu Ile Val Leu Val Gly Gly Ser Thr Arg Ile Pro Lys
            340                 345                 350
Ile Gln Gln Leu Val Lys Glu Phe Phe Asn Gly Lys Glu Pro Ser Arg
            355                 360                 365
Gly Ile Asn Pro Asp Glu Ala Val Ala Tyr Gly Ala Ala Val Gln Ala
            370                 375                 380
Gly Val Leu Ser Gly Asp Gln Asp Thr Gly Asp Leu Val Leu Leu Asp
385                 390                 395                 400
Val Cys Pro Leu Thr Leu Gly Ile Glu Thr Val Gly Gly Val Met Thr
                405                 410                 415
Lys Leu Ile Pro Arg Asn Thr Val Val Pro Thr Lys Lys Ser Gln Ile
            420                 425                 430
```

```
Phe Ser Thr Ala Ser Asp Asn Gln Pro Thr Val Thr Ile Lys Val Tyr
            435                 440                 445

Glu Gly Glu Arg Pro Leu Thr Lys Asp Asn His Leu Leu Gly Thr Phe
        450                 455                 460

Asp Leu Thr Gly Ile Pro Pro Ala Pro Arg Gly Val Pro Gln Ile Glu
465                 470                 475                 480

Val Thr Phe Glu Ile Asp Val Asn Gly Ile Leu Arg Val Thr Ala Glu
                485                 490                 495

Asp Lys Gly Thr Gly Asn Lys Asn Lys Ile Thr Ile Thr Asn Asp Gln
            500                 505                 510

Asn Arg Leu Thr Pro Glu Glu Ile Glu Arg Met Val Asn Asp Ala Glu
        515                 520                 525

Lys Phe Ala Glu Glu Asp Lys Lys Leu Lys Glu Arg Ile Asp Thr Arg
530                 535                 540

Asn Glu Leu Glu Ser Tyr Ala Tyr Ser Leu Lys Asn Gln Ile Gly Asp
545                 550                 555                 560

Lys Glu Lys Leu Gly Gly Lys Leu Ser Ser Glu Asp Lys Glu Thr Met
                565                 570                 575

Glu Lys Ala Val Glu Glu Lys Ile Glu Trp Leu Glu Ser His Gln Asp
            580                 585                 590

Ala Asp Ile Glu Asp Phe Lys Ala Lys Lys Glu Leu Glu Glu Ile
        595                 600                 605

Val Gln Pro Ile Ile Ser Lys Leu Tyr Gly Ser Ala Gly Pro Pro Pro
                610                 615                 620

Thr Gly Glu Glu Asp Thr Ala Glu Lys Asp Glu Leu
625                 630                 635

<210> SEQ ID NO 9
<211> LENGTH: 637
<212> TYPE: PRT
<213> ORGANISM: Artificial
<220> FEATURE:
<223> OTHER INFORMATION: R-BipD peptide

<400> SEQUENCE: 9

Arg Glu Glu Glu Asp Lys Lys Glu Asp Val Gly Thr Val Val Gly Ile
1               5                   10                  15

Asp Leu Gly Thr Thr Tyr Ser Cys Val Gly Val Phe Lys Asn Gly Arg
                20                  25                  30

Val Glu Ile Ile Ala Asn Asp Gln Gly Asn Arg Ile Thr Pro Ser Tyr
            35                  40                  45

Val Ala Phe Thr Pro Glu Gly Glu Arg Leu Ile Gly Asp Ala Ala Lys
        50                  55                  60

Asn Gln Leu Thr Ser Asn Pro Glu Asn Thr Val Phe Asp Ala Lys Arg
65                  70                  75                  80

Leu Ile Gly Arg Thr Trp Asn Asp Pro Ser Val Gln Gln Asp Ile Lys
                85                  90                  95

Phe Leu Pro Phe Lys Val Val Glu Lys Lys Thr Lys Pro Tyr Ile Gln
            100                 105                 110

Val Asp Ile Gly Gly Gly Gln Thr Lys Thr Phe Ala Pro Glu Glu Ile
        115                 120                 125

Ser Ala Met Val Leu Thr Lys Met Lys Glu Thr Ala Glu Ala Tyr Leu
130                 135                 140

Gly Lys Lys Val Thr His Ala Val Val Thr Val Pro Ala Tyr Phe Asn
145                 150                 155                 160
```

```
Asp Ala Gln Arg Gln Ala Thr Lys Asp Ala Gly Thr Ile Ala Gly Leu
            165                 170                 175
Asn Val Met Arg Ile Ile Asn Glu Pro Thr Ala Ala Ile Ala Tyr
        180                 185                 190
Gly Leu Asp Lys Arg Glu Gly Lys Asn Ile Leu Val Phe Asp Leu
        195                 200                 205
Gly Gly Gly Thr Phe Asp Val Ser Leu Leu Thr Ile Asp Asn Gly Val
        210                 215                 220
Phe Glu Val Val Ala Thr Asn Gly Asp Thr His Leu Gly Gly Glu Asp
225                 230                 235                 240
Phe Asp Gln Arg Val Met Glu His Phe Ile Lys Leu Tyr Lys Lys Lys
                245                 250                 255
Thr Gly Lys Asp Val Arg Lys Asp Asn Arg Ala Val Gln Lys Leu Arg
            260                 265                 270
Arg Glu Val Glu Lys Ala Lys Arg Ala Leu Ser Ser Gln His Gln Ala
        275                 280                 285
Arg Ile Glu Ile Glu Ser Phe Tyr Glu Gly Gly Asp Phe Ser Glu Thr
    290                 295                 300
Leu Thr Arg Ala Lys Phe Glu Glu Leu Asn Met Asp Leu Phe Arg Ser
305                 310                 315                 320
Thr Met Lys Pro Val Gln Lys Val Leu Glu Asp Ser Asp Leu Lys Lys
                325                 330                 335
Ser Asp Ile Asp Glu Ile Val Leu Val Gly Gly Ser Thr Arg Ile Pro
            340                 345                 350
Lys Ile Gln Gln Leu Val Lys Glu Phe Phe Asn Gly Lys Glu Pro Ser
        355                 360                 365
Arg Gly Ile Asn Pro Asp Glu Ala Val Ala Tyr Gly Ala Ala Val Gln
    370                 375                 380
Ala Gly Val Leu Ser Gly Asp Gln Asp Thr Gly Asp Leu Val Leu Leu
385                 390                 395                 400
Asp Val Cys Pro Leu Thr Leu Gly Ile Glu Thr Val Gly Gly Val Met
                405                 410                 415
Thr Lys Leu Ile Pro Arg Asn Thr Val Val Pro Thr Lys Lys Ser Gln
            420                 425                 430
Ile Phe Ser Thr Ala Ser Asp Asn Gln Pro Thr Val Thr Ile Lys Val
        435                 440                 445
Tyr Glu Gly Glu Arg Pro Leu Thr Lys Asp Asn His Leu Leu Gly Thr
    450                 455                 460
Phe Asp Leu Thr Gly Ile Pro Pro Ala Pro Arg Gly Val Pro Gln Ile
465                 470                 475                 480
Glu Val Thr Phe Glu Ile Asp Val Asn Gly Ile Leu Arg Val Thr Ala
                485                 490                 495
Glu Asp Lys Gly Thr Gly Asn Lys Asn Lys Ile Thr Ile Thr Asn Asp
            500                 505                 510
Gln Asn Arg Leu Thr Pro Glu Glu Ile Glu Arg Met Val Asn Asp Ala
        515                 520                 525
Glu Lys Phe Ala Glu Glu Asp Lys Lys Leu Lys Glu Arg Ile Asp Thr
    530                 535                 540
Arg Asn Glu Leu Glu Ser Tyr Ala Tyr Ser Leu Lys Asn Gln Ile Gly
545                 550                 555                 560
Asp Lys Glu Lys Leu Gly Gly Lys Leu Ser Ser Glu Asp Lys Glu Thr
                565                 570                 575
Met Glu Lys Ala Val Glu Glu Lys Ile Glu Trp Leu Glu Ser His Gln
```

```
                580                 585                 590
Asp Ala Asp Ile Glu Asp Phe Lys Ala Lys Lys Lys Glu Leu Glu Glu
        595                 600                 605

Ile Val Gln Pro Ile Ile Ser Lys Leu Tyr Gly Ser Ala Gly Pro Pro
        610                 615                 620

Pro Thr Gly Glu Glu Asp Thr Ala Glu Lys Asp Glu Leu
625                 630                 635
```